US012751944B2

(12) United States Patent
Page et al.

(10) Patent No.: US 12,751,944 B2
(45) Date of Patent: Oct. 6, 2026

(54) METHODS AND COMPOSITIONS FOR TREATING FUNGAL INFECTIONS

(71) Applicant: Neoculi Pty Ltd, Burwood (AU)

(72) Inventors: Stephen Page, Newtown (AU); Adam McCluskey, Charlestown (AU); Martine Keenan, Murdoch (AU); Andrew Stevens, Farrer (AU); Sanjay Garg, Myrtle Bank (AU)

(73) Assignee: Neoculi Pty Ltd, Burwood (AU)

( * ) Notice: Subject to any disclaimer, the term of this patent is extended or adjusted under 35 U.S.C. 154(b) by 631 days.

(21) Appl. No.: 17/996,655

(22) PCT Filed: Apr. 23, 2021

(86) PCT No.: PCT/AU2021/050367

§ 371 (c)(1),
(2) Date: Oct. 20, 2022

(87) PCT Pub. No.: WO2021/212181

PCT Pub. Date: Oct. 28, 2021

(65) Prior Publication Data

US 2023/0310388 A1 Oct. 5, 2023

(30) Foreign Application Priority Data

Apr. 24, 2020 (AU) ................................ 2020901286

(51) Int. Cl.

| | |
|---|---|
| ***A61K 31/433*** | (2006.01) |
| ***A61K 31/245*** | (2006.01) |
| ***A61K 31/4164*** | (2006.01) |
| ***A61K 31/428*** | (2006.01) |
| ***A61K 31/4709*** | (2006.01) |
| ***A61K 31/498*** | (2006.01) |
| ***A61P 31/10*** | (2006.01) |

(52) U.S. Cl.

CPC .......... *A61K 31/433* (2013.01); *A61K 31/245* (2013.01); *A61K 31/4164* (2013.01); *A61K 31/428* (2013.01); *A61K 31/4709* (2013.01); *A61K 31/498* (2013.01); *A61P 31/10* (2018.01)

(58) Field of Classification Search

CPC .............. A61K 31/4164; A61K 31/245; A61K 31/433; A61P 31/10

See application file for complete search history.

(56) References Cited

U.S. PATENT DOCUMENTS 11,723,362 B2 * 8/2023 Hart-Cooper ............. A01P 1/00
504/337

FOREIGN PATENT DOCUMENTS

| | | | |
|---|---|---|---|
| CN | 110251497 | A | 9/2019 |
| WO | WO 2014/176634 | A1 | 11/2014 |
| WO | WO 2016/033635 | A1 | 3/2016 |

OTHER PUBLICATIONS

Abraham et al., Robenidine Analogues as Gram-Positive Antibacterial Agents. Journal of Medicinal Chemistry, Jan. 2016, 59(5), pp. 2126-2138.

Almeida F, et al. The Still Underestimated Problem of Fungal Diseases Worldwide. Front Microbiol. Feb. 12, 2019;10:214.

Bhander, et al., Antifungal Drug Resistance—Concerns for Veterinarians. Veterinary World, May 2009. 2(5): 204-207.

Bourély C, et al. Antimicrobial resistance patterns of bacteria isolated from dogs with otitis. Epidemiol Infect. Jan. 2019;147:e121. 10 pages.

Chan WY, et al. In vitro antimicrobial activity of monensin against common clinical isolates associated with canine otitis externa. Comp Immunol Microbiol Infect Dis. Apr. 2018;57:34-38.

Chan WY, et al. In vitro antimicrobial activity of seven adjuvants against common pathogens associated with canine otitis externa. Vet Dermatol. Apr. 2019;30(2):133-e38. 5 pages.

Digby SS, et al. Darier Disease Complicated by Terbinafine-resistant Trichophyton rubrum: A Case Report. Acta Derm Venereol. Jan. 4, 2017;97(1):139-140.

Ebert A, et al. Alarming India-wide phenomenon of antifungal resistance in dermatophytes: A multicentre study. Mycoses, Jul. 2020, vol. 63, Issue7, 717-728.

Einchenberg, et al. Susceptibility of Malassezia pachydermatis to azole antifungal agents evaluated by a new broth microdilution method. Acta Scientiae Veterinariae. Jun. 2018, 31(2):75-80.

Finnegan S, Percival SL. EDTA: An Antimicrobial and Antibiofilm Agent for Use in Wound Care. Adv Wound Care (New Rochelle). Jul. 1, 2015;4(7):415-421.

(Continued)

*Primary Examiner* — Marcos L Sznaidman

(74) *Attorney, Agent, or Firm* — Howson & Howson LLP; Colleen M. Schaller

(57) ABSTRACT

Provided herein are methods of treating or preventing a fungal colonisation or infection in a subject. The method includes administering a therapeutically effective amount of a compound, or a therapeutically acceptable salt thereof, to the subject, wherein the fungal colonisation or infection is caused by a fungal agent. In certain embodiments, the compound is a compound of Formula I, or a stereoisomer, tautomer, pharmaceutically acceptable salt, or prodrug thereof:

Formula I

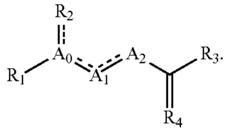

26 Claims, 11 Drawing Sheets

(56) References Cited

OTHER PUBLICATIONS

Hamoud R, et al. Synergistic antibacterial activity of the combination of the alkaloid sanguinarine with EDTA and the antibiotic streptomycin against multidrug resistant bacteria. J Pharm Pharmacol. Feb. 2015;67(2):264-73.

Hiruma J,et al. Terbinafine-resistant strain of Trichophyton interdigitale strain isolated from a tinea pedis patient. J Dermatol. Apr. 2019;46(4):351-353.

Kano R, et al. High multi-azole-resistant Malassezia pachydermatis clinical isolates from canine Malassezia dermatitis. Med Mycol. Feb. 1, 2020;58(2):197-200.

Khazandi M, et al. In vitro Antimicrobial Activity of Robenidine, Ethylenediaminetetraacetic Acid and Polymyxin B Nonapeptide Against Important Human and Veterinary Pathogens. Front Microbiol. Apr. 25, 2019;10:837.

Korbelik, et al., Characterization of the otic bacterial microbiota in dogs with otitis externa compared to healthy individuals. Veterinary Dermatology, Jun. 2019, vol. 30, Issue 3. 10 pages.

Litster A, et al. Prevalence of bacterial species in cats with clinical signs of lower urinary tract disease: recognition of *Staphylococcus felis* as a possible feline urinary tract pathogen. Vet Microbiol. Mar. 31, 2007;121(1-2):182-8.

Monod M, et al. Trichophyton rubrum Azole Resistance Mediated by a New ABC Transporter, TruMDR3. Antimicrob Agents Chemother. Oct. 22, 2019;63(11):e00863-19. 19 pages.

Monod M. Antifungal resistance in dermatophytes: Emerging problem and challenge for the medical community. J Mycol Med. Dec. 2019;29(4):283-284.

Nenoff P, et al. The current Indian epidemic of superficial dermatophytosis due to Trichophyton mentagrophytes—A molecular study. Mycoses. Apr. 2019;62(4):336-356.

Nuttall T, Bensignor E. A pilot study to develop an objective clinical score for canine otitis externa. Vet Dermatol. Dec. 2014;25(6):530-7, e91-2. 10 pages.

Ogunniyi AD, et al. Evaluation of robenidine analog NCL 195 as a novel broad-spectrum antibacterial agent. PLoS One. Sep. 5, 2017;12(9):e0183457. 23 pages.

Osborne CS, et al. Amino acid substitution in Trichophyton rubrum squalene epoxidase associated with resistance to terbinafine. Antimicrob Agents Chemother. Jul. 2005;49(7):2840-4.

Osborne CS, et al. Biological, biochemical, and molecular characterization of a new clinical Trichophyton rubrum isolate resistant to terbinafine. Antimicrob Agents Chemother. Jun. 2006;50(6):2234-6.

Perfect JR. Is there an emerging need for new antifungals?, Expert Opin Emerg Drugs. Jun. 2016;21(2):129-31.

Saunte DML, et al. Emerging Terbinafine Resistance in Trichophyton: Clinical Characteristics, Squalene Epoxidase Gene Mutations, and a Reliable EUCAST Method for Detection. Antimicrob Agents Chemother. Sep. 23, 2019;63(10):e01126-19. 9 pages.

Schøsler L, et al. Recurrent terbinafine resistant Trichophyton rubrum infection in a child with congenital ichthyosis. Pediatr Dermatol. Mar. 2018;35(2):259-260.

Sim JXF, et al. Antimicrobial effects of cinnamon essential oil and cinnamaldehyde combined with EDTA against canine otitis externa pathogens. J Appl Microbiol. Jul. 2019;127(1):99-108.

Von Silva-Tarouca MSE, et al. Determination of minimum inhibitory concentrations for silver sulfadiazine and other topical antimicrobial agents against strains of Pseudomonas aeruginosa isolated from canine otitis externa. Vet Dermatol. Apr. 2019;30(2):145-e42. 8 pages.

Yamada T, et al. Terbinafine Resistance of Trichophyton Clinical Isolates Caused by Specific Point Mutations in the Squalene Epoxidase Gene. Antimicrob Agents Chemother. Jun. 27, 2017;61(7):e00115-17. 13 pages.

International Search Report and Written Opinion in Internation Patent Application No. PCT/AU2021/050367, mailed Jul. 7, 2021.

* cited by examiner

FIGURE 1

| NCL COMPOUND CODE | COMPOUND NAME | COMPOUND STRUCTURE |
|---|---|---|
| NCL276 | (*E*)-*N'*-((*E*)-benzo[c][1,2,5]thiadiazol-4-ylmethylene)-2-(benzo[c][1,2,5]thiadiazol-4-ylmethylene)hydrazine-1-carboximidhydrazide hydrochloride | 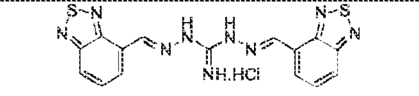 |
| NCL277 | (*E*)-*N'*-((*E*)-benzo[c][1,2,5]thiadiazol-5-ylmethylene)-2-(benzo[c][1,2,5]thiadiazol-5-ylmethylene)hydrazine-1-carboximidhydrazide hydrochloride | 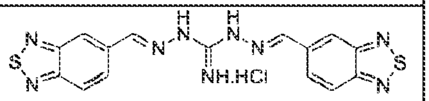 |
| NCL278 | (*E*)-2-(quinoxalin-2-ylmethylene)hydrazine-1-carboximidamide hydrochloride | 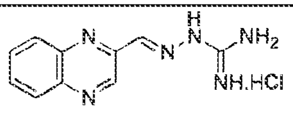 |
| NCL279 | (*E*)-2-(benzo[d]thiazol-2-ylmethylene)hydrazine-1-carboximidamide hydrochloride | 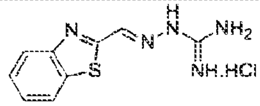 |
| NCL280 | (*E*)-2-(benzo[c][1,2,5]thiadiazol-5-ylmethylene)hydrazine-1-carboximidamide hydrochloride | 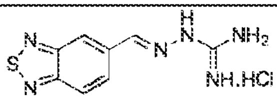 |
| NCL281 | (*E*)-2-(benzo[c][1,2,5]thiadiazol-4-ylmethylene)hydrazine-1-carboximidamide hydrochloride | 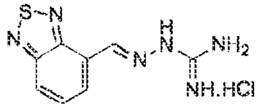 |
| NCL282 | (*E*)-*N'*-((*E*)-quinolin-6-ylmethylene)-2-(quinolin-6-ylmethylene)hydrazine-1-carboximidhydrazide hydrochloride | 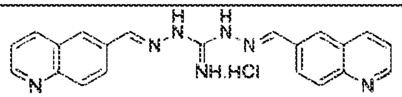 |
| NCL283 | (*E*)-2-((4-methyl-1*H*-imidazol-5-yl)methylene)hydrazine-1-carboximidamide hydrochloride | 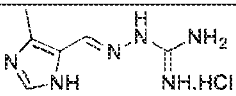 |

FIGURE 2

| NCL | Name | Group - G/GM/P/O |
|---|---|---|
| NCL812 | 2,2'-bis[(4-chlorophenyl)methylene]carbonimidic dihydrazide hydrochloride | G |
| NCL001 | 2,2'-bis[(4-chlorophenyl)methylene] carbonic dihydrazide | O |
| NCL002 | 2,2'-bis[(2-chlorophenyl)methylene] carbonic dihydrazide | O |
| NCL003 | 2,2'-bis[(4-fluorophenyl)methylene] carbonic dihydrazide | O |
| NCL004 | 2,2'-bis[(3-fluorophenyl)methylene] carbonic dihydrazide | O |
| NCL005 | 2,2'-bis[(2-fluorophenyl)methylene] carbonic dihydrazide | O |
| NCL006 | 2,2'-bis[(4-methoxyphenyl)methylene] carbonic dihydrazide | O |
| NCL007 | 2,2'-bis[(4-cyanophenyl)methylene] carbonic dihydrazide | O |
| NCL008 | 2,2'-bis[(2-cyanophenyl)methylene] carbonic dihydrazide | O |
| NCL009 | 2,2'-bis[(3-cyanophenyl)methylene] carbonic dihydrazide | O |
| NCL010 | 2,2'-bis[(3-methoxyphenyl)methylene] carbonic dihydrazide | O |
| NCL011 | 2,2'-bis{[3-(trifluoromethyl)phenyl]methylene} carbonic dihydrazide | O |
| NCL012 | 2,2'-bis{[4-(trifluoromethyl)phenyl]methylene} carbonic dihydrazide | O |
| NCL013 | 2,2'-bis{[2-(trifluoromethyl)phenyl]methylene} carbonic dihydrazide | O |
| NCL014 | 2-[(4-chlorophenyl)methylene] hydrazinecarboxamide | O |
| NCL015 | 2-[(2-chlorophenyl)methylene] hydrazine carboximidamide hydrochloride | GM |
| NCL016 | 2-[(2-fluorophenyl)methylene] hydrazine carboximidamide hydrochloride | GM |
| NCL017 | 2-[(3-fluorophenyl)methylene] hydrazine carboximidamide hydrochloride | GM |
| NCL018 | 2,2'-bis[(2-methylphenyl)methylene] carbonic dihydrazide | O |
| NCL019 | 2,2'-bis[(3-methylphenyl)methylene] carbonic dihydrazide | O |
| NCL020 | 2,2'-bis[(2-chlorophenyl)methylene] carbonimidic dihydrazide hydrochloride | G |
| NCL021 | 2,2'-bis[(4-fluorophenyl)methylene] carbonimidic dihydrazide hydrochloride | G |
| NCL022 | 2,2'-bis[(2-fluorophenyl)methylene] carbonimidic dihydrazide hydrochloride | G |
| NCL023 | 2,2'-bis[(3-fluorophenyl)methylene] carbonimidic dihydrazide hydrochloride | G |
| NCL024 | 2,2'-bis[(4-cyanophenyl)methylene] carbonimidic dihydrazide hydrochloride | G |
| NCL025 | 2,2'-bis[(2-cyanophenyl)methylene] carbonimidic dihydrazide hydrochloride | G |
| NCL026 | 2,2'-bis[(3-cyanophenyl)methylene] carbonimidic dihydrazide hydrochloride | G |
| NCL027 | 2,2'-bis[(4-methoxyphenyl)methylene] carbonimidic dihydrazide hydrochloride | G |
| NCL028 | 2,2'-bis[(2-methoxyphenyl)methylene] carbonimidic dihydrazide hydrochloride | G |
| NCL029 | 2,2'-bis[(3-methoxyphenyl)methylene] carbonimidic dihydrazide hydrochloride | G |
| NCL030 | 2-[(4-chlorophenyl)methylene] hydrazine carboximidamide hydrochloride | GM |
| NCL031 | 2-[(4-cyanophenyl)methylene] hydrazine carboximidamide hydrochloride | GM |
| NCL032 | 2-[(2-cyanophenyl)methylene] hydrazine carboximidamide hydrochloride | GM |
| NCL033 | 2-[(3-cyanophenyl)methylene] hydrazine carboximidamide hydrochloride | GM |
| NCL034 | 2-[(2-methoxyphenyl)methylene] hydrazine carboximidamide hydrochloride | GM |
| NCL035 | 2,2'-bis{[4-(trifluoromethyl)phenyl]methylene} carbonimidic dihydrazide hydrochloride | G |

FIGURE 2 CONTINUED

| | | |
|---|---|---|
| NCL036 | 2,2'-bis{[2-(trifluoromethyl)phenyl]methylene} carbonimidic dihydrazide hydrochloride | G |
| NCL037 | 2,2'-bis{[3-(trifluoromethyl)phenyl]methylene} carbonimidic dihydrazide hydrochloride | G |
| NCL038 | 2,2'-bis[(4-methylphenyl)methylene] carbonimidic dihydrazide hydrochloride | G |
| NCL039 | 2,2'-bis[(2-methylphenyl)methylene] carbonimidic dihydrazide hydrochloride | G |
| NCL040 | 2,2'-bis[(3-methylphenyl)methylene] carbonimidic dihydrazide hydrochloride | G |
| NCL041 | 2-{[4-(trifluoromethyl)phenyl]methylene} hydrazine carboximidamide hydrochloride | GM |
| NCL042 | 2-{[2-(trifluoromethyl)phenyl]methylene} hydrazine carboximidamide hydrochloride | GM |
| NCL043 | 2-{[3-(trifluoromethyl)phenyl]methylene} hydrazine carboximidamide hydrochloride | GM |
| NCL044 | 2-[(4-methylphenyl)methylene] hydrazine carboximidamide hydrochloride | GM |
| NCL045 | 2-[(2-methylphenyl)methylene] hydrazine carboximidamide hydrochloride | GM |
| NCL046 | 2-[(3-methylphenyl)methylene] hydrazine carboximidamide hydrochloride | GM |
| NCL047 | 2-[(2-chlorophenyl)methylene] hydrazinecarboxamide | O |
| NCL048 | 2-[(2-fluorophenyl)methylene] hydrazinecarboxamide | O |
| NCL049 | 2-[(4-cyanophenyl)methylene] hydrazinecarboxamide | O |
| NCL050 | 2-[(2-cyanophenyl)methylene] hydrazinecarboxamide | O |
| NCL051 | 2-[(3-cyanophenyl)methylene] hydrazinecarboxamide | O |
| NCL052 | 2-[(3-chlorophenyl)methylene] hydrazine carboximidamide hydrochloride | GM |
| NCL053 | 2-[(4-fluorophenyl)methylene] hydrazine carboximidamide hydrochloride | G |
| NCL054 | 2,2'-bis[(3-chlorophenyl)methylene] carbonimidic dihydrazide hydrochloride | G |
| NCL055 | 2-[(3-chlorophenyl)methylene] hydrazinecarboxamide | O |
| NCL056 | 2-[(4-fluorophenyl)methylene] hydrazinecarboxamide | O |
| NCL057 | 2-[(3-fluorophenyl)methylene] hydrazinecarboxamide | O |
| NCL058 | 2-[(4-methoxyphenyl)methylene] hydrazinecarboxamide | O |
| NCL059 | 2-[(3-methoxyphenyl)methylene] hydrazinecarboxamide | O |
| NCL060 | 2-{[(2-trifluoromethyl)phenyl]methylene} hydrazinecarboxamide | O |
| NCL061 | 2,2'-bis{1-[4-(trifluoromethyl)phenyl]ethylidene} carbonimidic dihydrazide hydrochloride | G |
| NCL062 | 2,2'-bis{1-[4-chlorophenyl]ethylidene} carbonimidic dihydrazide hydrochloride | G |
| NCL063 | 2,2'-bis{[4-(trifluoromethyl)phenyl]methylene} carbonothioicdihydrazide | O |
| NCL064 | 2,2'-bis[(2-cyanophenyl)methylene] carbonothioicdihydrazide | O |
| NCL065 | 2,2'-bis[(3-cyanophenyl)methylene] carbonothioicdihydrazide | O |
| NCL066 | 2,2'-bis[(3-fluorophenyl)methylene] carbonothioicdihydrazide | O |
| NCL067 | 2-{[(3-trifluoromethyl)phenyl]methylene} hydrazinecarboxamide | O |

FIGURE 2 CONTINUED

| | | |
|---|---|---|
| NCL068 | 2-[1-(4-chlorophenyl)ethylidene]-2'-{1-[4-(trifluoromethyl)phenyl]methylene} carbonimidic dihydrazide hydrochloride | G |
| NCL069 | 2-[1-(4-chlorophenyl)ethylidene] carbonimidic dihydrazide hydrochloride | GM |
| NCL070 | 2,2'-bis[(3-chlorophenyl)methylene] carbonothioicdihydrazide | O |
| NCL071 | 2-[(2-methoxyphenyl)methylene] hydrazinecarbothioamide | O |
| NCL072 | 2-[(4-chlorophenyl)methylene] carbonimidic dihydrazide hydrochloride | GM |
| NCL073 | 2-{[1-(4-trifluoromethyl)phenyl]ethylidene} carbonimidic dihydrazide hydrochloride | GM |
| NCL074 | 2-[(2,4-dichlorophenyl)methylene]-2'-[(4-chlorophenyl)methylene] carbonimidic dihydrazide hydrochloride | G |
| NCL075 | 2-{1-[4-(trifluoromethyl)phenyl]ethylidene}-2'-{[4-(trifluoromethyl)phenyl]methylene} carbonimidic dihydrazide hydrochloride | G |
| NCL076 | 2-[(4-chlorophenyl)methylene]-2'-[(4-methylphenyl)methylene] carbonimidic dihydrazide hydrochloride | G |
| NCL077 | 2-[(4-chlorophenyl)methylene]-2'-{[4-(trifluoromethyl)phenyl]methylene} carbonimidic dihydrazide hydrochloride | G |
| NCL078 | 2-{[2-fluoro-4-(trifluoromethyl)phenyl]methylene}-2'-[(4-chlorophenyl)methylene] carbonimidic dihydrazide hydrochloride | G |
| NCL079 | 2-[(4-chlorophenyl)methylene]-2'-[(4-fluorophenyl)methylene] carbonimidic dihydrazide hydrochloride | G |
| NCL080 | 2-{1-[4-(trifluoromethyl)phenyl]ethylidene}-2'-[(4-chlorophenyl)methylene] carbonimidic dihydrazide hydrochloride | G |
| NCL081 | 2-[1-(4-chlorophenyl)ethylidene]-2'-[(4-chlorophenyl)methylene] carbonimidic dihydrazide hydrochloride | G |
| NCL082 | 2-[(2-chlorophenyl)methylene]-2'-[(4-chlorophenyl)methylene] carbonimidic dihydrazide hydrochloride | G |
| NCL083 | 2-[(3-chlorophenyl)methylene]-2'-[(4-chlorophenyl)methylene] carbonimidic dihydrazide hydrochloride | G |
| NCL084 | 2-[(2-fluoro-4-chlorophenyl)methylene]-2'-[(4-chlorophenyl)methylene] carbonimidic dihydrazide hydrochloride | G |
| NCL085 | 2-[(2-cyanophenyl)methylene]-2'-[(4-chlorophenyl)methylene] carbonimidic dihydrazide hydrochloride | G |
| NCL086 | 2-[(3-cyanophenyl)methylene]-2'-[(4-chlorophenyl)methylene] carbonimidic dihydrazide hydrochloride | G |
| NCL087 | 2-[(4-chlorophenyl)methylene]-2'-[(4-cyanophenyl)methylene] carbonimidic dihydrazide hydrochloride | G |
| NCL088 | 2-[(2-fluorophenyl)methylene]-2'-[(4-chlorophenyl)methylene] carbonimidic dihydrazide hydrochloride | G |
| NCL089 | 2-[1-(4-chlorophenyl)ethylidene]-2'-{1-[4-(trifluoromethyl)phenyl]ethylidene} carbonimidic dihydrazide hydrochloride | G |
| NCL090 | N-benzoyl-1-benzoyl-2-[(2-chlorophenyl)methylene] hydrazine carboximidamide hydrochloride | O |
| NCL091 | N-(4-chlorophenyl)-3-[4-(trifluoromethyl)phenyl]-1H-1,2,4-triazol-5-amine | O |
| NCL092 | N-(4-chlorobenzyl)-3-(4-chlorophenyl)-1H-1,2,4-triazol-5-amine | O |
| NCL093 | 2,2'-bis(2-naphthalenylmethylene)carbonimidic dihydrazide hydrochloride | G |
| NCL094 | 2,2'-bis(cyclohexylmethylene)carbonimidic dihydrazide hydrochloride | G |
| NCL095 | 2,2'-bis(3-furanylmethylene)carbonimidic dihydrazide hydrochloride | G |

FIGURE 2 CONTINUED

| | | |
|---|---|---|
| NCL096 | 2,2'-bis(3-phenyl-2-propenylidene)carbonimidic dihydrazide hydrochloride | G |
| NCL097 | 2,2'-bis[(3,4,5-trihydroxyphenyl)methylene] carbonimidic dihydrazide hydrochloride | G |
| NCL098 | 2,2'-bis[(3-carboxyphenyl)methylene] carbonimidic dihydrazide hydrochloride | G |
| NCL099 | 2,2'-bis{[4-(1,1-dimethylethyl)phenyl]methylene} carbonimidic dihydrazide hydrochloride | G |
| NCL100 | 2,2'-bis(phenylmethylene)carbonimidic dihydrazide hydrochloride | G |
| NCL101 | 2,2'-bis[(2,3-dihydroxyphenyl)methylene] carbonimidic dihydrazide hydrochloride | G |
| NCL102 | 2,2'-bis[(2-nitrophenyl)methylene] carbonimidic dihydrazide hydrochloride | G |
| NCL103 | 2,2'-bis[(2,4-dihydroxyphenyl)methylene] carbonimidic dihydrazide hydrochloride | G |
| NCL104 | 2,2'-bis[(2,4,5-trihydroxyphenyl)methylene] carbonimidic dihydrazide hydrochloride | G |
| NCL105 | 2,2'-bis[(2,3,4-trihydroxyphenyl)methylene] carbonimidic dihydrazide hydrochloride | G |
| NCL106 | 2,2'-bis[(4,5-dihydroxy-3-methoxyphenyl)methylene] carbonimidic dihydrazide hydrochloride | G |
| NCL107 | 2,2'-bis[(2-hydroxyphenyl)methylene] carbonimidic dihydrazide hydrochloride | G |
| NCL108 | 2,2'-bis[(3-hydroxyphenyl)methylene] carbonimidic dihydrazide hydrochloride | G |
| NCL109 | 2,2'-bis[(3-nitrophenyl)methylene] carbonimidic dihydrazide hydrochloride | G |
| NCL110 | 2,2'-bis[(4-nitrophenyl)methylene] carbonimidic dihydrazide hydrochloride | G |
| NCL111 | 2,2'-bis[(3,4-dihydroxyphenyl)methylene] carbonimidic dihydrazide hydrochloride | G |
| NCL112 | 2,2'-bis([1,1'-biphenyl]-4-ylmethylene)carbonimidic dihydrazide hydrochloride | G |
| NCL113 | 2,2'-bis{4-(dimethylamino)phenyl]methylene} carbonimidic dihydrazide hydrochloride | G |
| NCL114 | 2,2'-bis[(3,5-dichlorophenyl)methylene] carbonimidic dihydrazide hydrochloride | G |
| NCL115 | 2,2'-bis[(3,4-dimethoxyphenyl)methylene] carbonimidic dihydrazide hydrochloride | G |
| NCL116 | 2,2'-bis([1,1'-biphenyl]-2-ylmethylene)carbonimidic dihydrazide hydrochloride | G |
| NCL117 | 2,2'-bis[(4-hydroxy-3-methoxyphenyl)methylene] carbonimidic dihydrazide hydrochloride | G |
| NCL118 | 2,2'-bis[(2,5-fluorophenyl)methylene] carbonimidic dihydrazide hydrochloride | G |
| NCL119 | 2,2'-bis[(4-acetamidophenyl)methylene] carbonimidic dihydrazide hydrochloride | G |
| NCL120 | 2,2'-bis{[4-(1-methylethyl)phenyl]methylene} carbonimidic dihydrazide hydrochloride | G |
| NCL121 | 2,2'-bis[(4-propylphenyl)methylene] carbonimidic dihydrazide hydrochloride | G |
| NCL122 | 2,2'-bis[(4-hydroxy-3-nitrophenyl)methylene] carbonimidic dihydrazide hydrochloride | G |

FIGURE 2 CONTINUED

| | | |
|---|---|---|
| NCL123 | 2,2'-bis[(3,4-difluorophenyl)methylene] carbonimidic dihydrazide hydrochloride | G |
| NCL124 | 2,2'-bis[(2-hydroxy-1-naphthalenyl)methylene] carbonimidic dihydrazide hydrochloride | G |
| NCL125 | 2,2'-bis[(3-hydroxy-4-methoxyphenyl)methylene] carbonimidic dihydrazide hydrochloride | G |
| NCL126 | 2,2'-bis[(3-ethynylphenyl)methylene] carbonimidic dihydrazide hydrochloride | G |
| NCL127 | 2,2'-bis[(2,4-dichlorophenyl)methylene] carbonimidic dihydrazide hydrochloride | G |
| NCL128 | 2,2'-bis[(2,3,4,5,6-pentafluorophenyl)methylene] carbonimidic dihydrazide hydrochloride | G |
| NCL129 | 2,2'-bis[(2-bromophenyl)methylene] carbonimidic dihydrazide hydrochloride | G |
| NCL130 | 2,2'-bis[(3-bromo-4,5-dimethoxyphenyl)methylene] carbonimidic dihydrazide hydrochloride | G |
| NCL131 | 2,2'-bis[(3-bromophenyl)methylene] carbonimidic dihydrazide hydrochloride | G |
| NCL132 | 2,2'-bis[(4-chloro-6-fluoro-2H-1-benzopyran-3-yl)methylene] carbonimidic dihydrazide hydrochloride | G |
| NCL133 | 2,2'-bis[(4-bromo-2-furanyl)methylene] carbonimidic dihydrazide hydrochloride | G |
| NCL134 | 2,2'-bis[(4-bromophenyl)methylene] carbonimidic dihydrazide hydrochloride | G |
| NCL135 | 2,2'-bis[(2-bromo-4,5-dimethoxyphenyl)methylene] carbonimidic dihydrazide hydrochloride | G |
| NCL136 | 2,2'-bis[(4-butylphenyl)methylene] carbonimidic dihydrazide hydrochloride | G |
| NCL137 | 2,2'-bis[(2,6-dichlorophenyl)methylene] carbonimidic dihydrazide hydrochloride | G |
| NCL138 | 2,2'-bis(2,3-diphenyl-2-propenylidene)carbonimidic dihydrazide hydrochloride | G |
| NCL139 | 2,2'-bis(3-quinolinylmethylene)carbonimidic dihydrazide hydrochloride | G |
| NCL140 | 2,2'-bis{[4-(methylsulfanyl)phenyl]methylene} carbonimidic dihydrazide hydrochloride | G |
| NCL141 | 2,2'-bis[(5-chlorobenzo[b]thien-3-yl)methylene] carbonimidic dihydrazide hydrochloride | G |
| NCL142 | 1,3-bis(benzylamino)guanidinehydrochloride | G |
| NCL143 | 2,2'-bis[1-phenylethylidene] carbonimidic dihydrazide hydrochloride | G |
| NCL144 | 2,2'-bis[(5-bromo-2-furanyl)methylene] carbonimidic dihydrazide hydrochloride | G |
| NCL145 | 2,2'-bis[(5-chloro-2-furanyl)methylene] carbonimidic dihydrazide hydrochloride | G |
| NCL146 | 2,2'-bis(1H-indol-5-ylmethylene)carbonimidic dihydrazide hydrochloride | G |
| NCL147 | 2,2'-bis(2-quinoxalinylmethylene)carbonimidic dihydrazide hydrochloride | G |
| NCL148 | 2,2'-bis{[4-(carboxypropenyl)phenyl]methylene} carbonimidic dihydrazide hydrochloride | G |
| NCL149 | 2,2'-Bis(4-pyridinylmethylene)Carbonimidic dihydrazide hydrochloride | G |
| NCL150 | 2,2'-bis[3-(4-methoxylphenyl)-2-propenylidene] carbonimidic dihydrazide hydrochloride | G |
| NCL151 | 2,2'-bis[(4-hydroxyphenyl)methylene] carbonimidic dihydrazide | G |

FIGURE 2 CONTINUED

| | | |
|---|---|---|
| | hydrochloride | |
| NCL152 | 2,2'-bis[(2-hydroxy-3-methylphenyl)methylene] carbonimidic dihydrazide hydrochloride | G |
| NCL153 | 2,2'-bis[1-(4-chlorophenyl)propylidene] carbonimidic dihydrazide hydrochloride | G |
| NCL154 | 2,2'-bis[1-(4-chlorophenyl)pentylidene] carbonimidic dihydrazide hydrochloride | G |
| NCL155 | 2,2'-bis[1-(4-bromophenyl)ethylidene] carbonimidic dihydrazide hydrochloride | G |
| NCL156 | 2,2'-bis[1-(4-chlorophenyl)butylidene] carbonimidic dihydrazide hydrochloride | G |
| NCL157 | 2,2'-bis[(2-amino-4-chlorophenyl)methylene] carbonimidic dihydrazide hydrochloride | G |
| NCL158 | 2,2'-bis[1-(2-hydroxy-4-chlorophenyl)propylidene] carbonimidic dihydrazide hydrochloride | G |
| NCL159 | 2,2'-bis[(2-hydroxy-4-chlorophenyl)(cyclopentyl)methylene] carbonimidic dihydrazide hydrochloride | G |
| NCL160 | 2,2'-bis{[4-(trifluoromethoxy)phenyl]methylene} carbonimidic dihydrazide hydrochloride | G |
| NCL161 | 2,2'-bis[1-(4-piperazinylphenyl)ethylidene] carbonimidic dihydrazide hydrochloride | G |
| NCL162 | ethyl(E)-N'-((E)-1-(4-chlorophenyl)ethylidene) carbamohydrazonate | O |
| NCL163 | 2,2'-bis(2-Oxo-1,2-dihydro-3H-indol-3-ylidene) carbonimidic dihydrazide hydrochloride | G |
| NCL164 | 2,2'-bis[1-(2-amino-4-chlorophenyl)ethylidene] carbonimidic dihydrazide hydrochloride | G |
| NCL165 | 2,2'-bis(1-phenyl-2-aminoethylidene) carbonimidic dihydrazide trihydrochloride | G |
| NCL166 | 2,2'-bis{[4-(trifluoromethylsulfanyl)phenyl]methylene} carbonimidic dihydrazide hydrochloride | G |
| NCL167 | 2,2'-bis(phenylcarboxymethylene) carbonimidic dihydrazide hydrochloride | G |
| NCL168 | 2,2'-bis{[2-(1-hydroxyethylamino)-4-chlorophenyl]methylene} carbonimidic dihydrazide hydrochloride | G |
| NCL169 | 2,2'-bis[(2-amino-4-chlorophenyl)methylene] carbonimidic dihydrazide | G |
| NCL170 | 2,2'-bis[(2-acetamido-4-chlorophenyl)methylene] carbonimidic dihydrazide | G |
| NCL171 | 2,2'-bis{[4-(dimethylamino)-2-hydroxyphenyl]methylene} carbonimidic dihydrazide | G |
| NCL172 | 2,2'-Bis[1-(2-pyridinyl)ethylidene] carbonimidic dihydrazide hydrochloride | G |
| NCL173 | 2,2'-bis[1-(4-chloro-2-hydroxyphenyl)ethylidene] carbonimidic dihydrazide hydrochloride | G |
| NCL174 | 2,2'-bis(4-chloro-2-hydroxyphenylmethylene) carbonimidic dihydrazide hydrochloride | G |
| NCL175 | 2,2'-Bis(4-chloropyridin-3-ylmethylene) carbonimidic dihydrazide hydrochloride | G |
| NCL176 | 2,2'-Bis(2-aminopyridin-3-ylmethylene) carbonimidic dihydrazide hydrochloride | G |
| NCL177 | 2,2'-bis[1-(4-chlorophenyl)-2-hydroxyethylidene] carbonimidic dihydrazide hydrochloride | G |

FIGURE 2 CONTINUED

| | | |
|---|---|---|
| NCL178 | 4,6-bis(2-((E)-1-(4-chlorophenyl)ethylidene)hydrazinyl) pyrimidine | P |
| NCL179 | 4,6-bis(2-((E)-4-chlorobenzylidene)hydrazinyl) pyrimidin-2-amine | P |
| NCL180 | (2Z,2'Z)-2,2'-(pyrimidine-4,6-diylbis(hydrazin-2-yl-1-ylidene))bis(2-(4-chlorophenyl)ethan-1-ol) | P |
| NCL181 | 4,6-bis(2-((E)-4-chlorobenzylidene)hydrazinyl) pyrimidine | P |
| NCL182 | 6-chloro-$N^4$-(1-phenylethyl) pyrimidine-2,4-diamine | P |
| NCL183 | $N^4$,$N^6$-bis(1-phenylethyl) pyrimidine-4,6-diamine | P |
| NCL184 | $N^4$,$N^6$-bis(1-phenylethyl) pyrimidine-2,4,6-triamine | P |
| NCL185 | 4,6-bis(2-((E)-1-(4-chlorophenyl)ethylidene)hydrazinyl) pyrimidine hydrochloride | P |
| NCL186 | $N^2$,$N^5$-bis(1-(4-chlorophenyl)ethyl) pyrazine-2,5-diamine | O |
| NCL187 | 4,6-bis(2-((E)-4-chlorobenzylidene)hydrazinyl) pyrimidine hydrochloride | P |
| NCL188 | (E)-2-(1-(4-chlorophenyl)pentylidene) hydrazine-1-carboximidamide hydrochloride | GM |
| NCL189 | (2Z,2'Z)-2,2'-(pyrimidine-4,6-diylbis(hydrazin-2-yl-1-ylidene))bis(2-(4-chlorophenyl)ethan-1-ol) hydrochloride | P |
| NCL190 | (Z)-2-(1-(4-chlorophenyl)-2-hydrazinylethylidene)hydrazine-1-carboximidamide hydrochloride | GM |
| NCL191 | (E)-2-(1-(4-chlorophenyl)ethylidene)hydrazine-1-carboximidamide hydrochloride | GM |
| NCL192 | (Z)-2-(2-carbamimidoylhydrazono)-2-phenylaceticacid hydrochloride | GM |
| NCL193 | 4,6-bis(2-((E)-4-bromobenzylidene)hydrazinyl) pyrimidin-2-amine | P |
| NCL194 | N',N'''-(2-aminopyrimidine-4,6-diyl)di(benzohydrazide) | P |
| NCL195 | 4,6-bis(2-((E)-4-methylbenzylidene)hydrazinyl) pyrimidin-2-amine | P |
| NCL196 | 4,4'-((1E,1'E)-((2-aminopyrimidine-4,6-diyl)bis(hydrazin-2-yl-1-ylidene))bis(methanylylidene)) diphenol | P |
| NCL197 | 3,3'-((1E,1'E)-((2-aminopyrimidine-4,6-diyl)bis(hydrazin-2-yl-1-ylidene))bis(methanylylidene)) diphenol | P |
| NCL198 | 4,6-bis(2-((E)-4-(tert-butyl)benzylidene)hydrazinyl) pyrimidin-2-amine dihydrochloride | P |
| NCL199 | 4,6-bis(2-((E)-benzylidene)hydrazinyl) pyrimidin-2-amine | P |
| NCL200 | 4,6-bis(2-((E)-4-(tert-butyl)benzylidene)hydrazinyl) pyrimidin-2-amine | P |
| NCL201 | 4,4'-((1E,1'E)-((2-aminopyrimidine-4,6-diyl)bis(hydrazin-2-yl-1-ylidene))bis(methanylylidene))bis(N,N-dimethylaniline) | P |
| NCL202 | 2,2'-((1E,1'E)-((2-aminopyrimidine-4,6-diyl)bis(hydrazin-2-yl-1-ylidene))bis(methanylylidene)) diphenol | P |
| NCL203 | 4,6-bis(2-((E)-cyclohexylmethylene)hydrazinyl) pyrimidin-2-amine dihydrochloride | P |
| NCL204 | 4,6-bis(2-((E)-1-(4-chlorophenyl)ethylidene)hydrazinyl) pyrimidin-2-amine | P |
| NCL205 | 4,6-bis(2-((E)-2-chlorobenzylidene)hydrazinyl) pyrimidin-2-amine | P |
| NCL206 | 4,6-bis(2-((E)-4-methylbenzylidene)hydrazinyl)-1,3,5-triazin-2-amine | P |
| NCL207 | 2,2'-((1E,1'E)-((6-amino-1,3,5-triazine-2,4-diyl)bis(hydrazin-2-yl-1-ylidene))bis(methanylylidene)) diphenol | P |
| NCL208 | 4,6-bis(2-((E)-1-(4-chlorophenyl)ethylidene)hydrazinyl)-1,3,5-triazin-2-amine | P |
| NCL209 | 3,3'-((1E,1'E)-((6-amino-1,3,5-triazine-2,4-diyl)bis(hydrazin-2-yl-1- | P |

FIGURE 2 CONTINUED

| | | |
|---|---|---|
| | ylidene))bis(methanylylidene)) diphenol | |
| NCL210 | 4,6-bis(2-((E)-4-(trifluoromethyl)benzylidene)hydrazinyl)-1,3,5-triazin-2-amine | P |
| NCL211 | 4,4'-((1E,1'E)-((6-amino-1,3,5-triazine-2,4-diyl)bis(hydrazin-2-yl-1-ylidene))bis(methanylylidene)) diphenol | P |
| NCL212 | 4,6-bis(2-((E)-4-bromobenzylidene)hydrazinyl)-1,3,5-triazin-2-amine | P |
| NCL213 | 4,6-bis(2-((E)-cyclohexylmethylene)hydrazinyl)-1,3,5-triazin-2-amine | P |
| NCL214 | 4,6-bis(2-((E)-benzylidene)hydrazinyl)-1,3,5-triazin-2-amine | P |
| NCL215 | (E)-N'-((E)-1-(4-chloro-2-fluorophenyl)ethylidene)-2-(1-(4-chloro-2-fluorophenyl)ethylidene)hydrazine-1-carboximidhydrazide hydrochloride | G |
| NCL216 | N',2-bis((E)-4-chloro-2-fluorobenzylidene)hydrazine-1-carboximidhydrazide hydrochloride | G |
| NCL217 | N',2-bis((E)-1-(p-tolyl)ethylidene)hydrazine-1-carboximidhydrazide hydrochloride | G |
| NCL218 | 4-((E)-(2-(2-amino-6-(2-((E)-4-((diethoxyphosphoryl)oxy)benzylidene)hydrazinyl)pyrimidin-4-yl)hydrazono)methyl) phenyldiethyl phosphate | P |
| NCL219 | (E)-N'-((E)-1-(4-(tert-butyl)phenyl)ethylidene)-2-(1-(4-(tert-butyl)phenyl)ethylidene)hydrazine-1-carboximidhydrazide hydrochloride | G |
| NCL220 | 4,6-bis(2-((E)-4-fluorobenzylidene)hydrazinyl) pyrimidin-2-amine | P |
| NCL221 | 4,6-bis(2-((E)-4-(trifluoromethyl)benzylidene)hydrazinyl) pyrimidin-2-amine | P |
| NCL222 | 4,6-bis(2-((E)-3,4-difluorobenzylidene)hydrazinyl) pyrimidin-2-amine | P |
| NCL223 | N,N'-(((1E,1'E)-((2-aminopyrimidine-4,6-diyl)bis(hydrazin-2-yl-1-ylidene))bis(methanylylidene))bis(4,1-phenylene)) diacetamide | P |
| NCL224 | ethyl2-((E)-4-chlorobenzylidene)-1-((E)-N'-((E)-4-chlorobenzylidene)carbamohydrazonoyl)hydrazine-1-carboxylate | G |
| NCL225 | isobutyl2-((E)-4-chlorobenzylidene)-1-((E)-N'-((E)-4-chlorobenzylidene)carbamohydrazonoyl) hydrazine-1-carboxylate | G |
| NCL226 | 2-((E)-4-chlorobenzylidene)-1-((E)-N'-((E)-4-chlorobenzylidene)carbamohydrazonoyl)-N-ethylhydrazine-1-carboxamide | G |
| NCL227 | N-benzyl-2-((E)-4-chlorobenzylidene)-1-((E)-N'-((E)-4-chlorobenzylidene)carbamohydrazonoyl) hydrazine-1-carboxamide | G |
| NCL228 | 2-((E)-4-chlorobenzylidene)-1-((E)-N'-((E)-4-chlorobenzylidene)carbamohydrazonoyl)-N-hexylhydrazine-1-carboxamide | G |
| NCL229 | 2-((E)-4-chlorobenzylidene)-1-((E)-N'-((E)-4-chlorobenzylidene)carbamohydrazonoyl)-N-(furan-2-ylmethyl)hydrazine-1-carboxamide | G |
| NCL230 | 4,6-bis(2-((E)-4-methoxybenzylidene)hydrazinyl) pyrimidin-2-amine | P |
| NCL231 | (E)-2-(1-(4-(tert-butyl)phenyl)ethylideneamino) guanidine | GM |
| NCL232 | (E)-2-(4-(tert-butyl)benzylideneamino) guanidine | GM |
| NCL233 | (E)-2-(1-(4-chlorophenyl)butylidene)hydrazine-1-carboximidamide hydrochloride | GM |
| NCL234 | (E)-2-(1-(4-chlorophenyl)propylidene)hydrazine-1-carboximidamide | GM |
| NCL235 | (E)-2-(4-chloro-2-fluorobenzylidene)hydrazine-1-carboximidamide | GM |
| NCL236 | (E)-2-(1-(4-chloro-2-fluorophenyl)ethylidene)hydrazine-1-carboximidamide | GM |
| NCL237 | (E)-2-(1-(4-chloro-2-hydroxyphenyl)-2-cyclohexylethylideneamino) guanidine | GM |

FIGURE 2 CONTINUED

| | | |
|---|---|---|
| NCL238 | 4,6-bis(2-((E)-(6-chloropyridin-3-yl)methylene)hydrazinyl) pyrimidin-2-amine | P |
| NCL239 | 4,6-bis(2-((E)-pyridin-3-ylmethylene)hydrazinyl) pyrimidin-2-amine | P |
| NCL240 | 4,6-bis(2-((E)-pyridin-2-ylmethylene)hydrazinyl) pyrimidin-2-amine | P |
| NCL241 | 4,6-bis(2-((E)-pyridin-4-ylmethylene)hydrazinyl) pyrimidin-2-amine | P |
| NCL242 | 4,6-bis(2-((E)-2,5-dihydroxybenzylidene)hydrazinyl) pyrimidin-2-aminium 2-formyl-4-hydroxyphenolate | P |
| NCL243 | 4,6-bis(2-((E)-3,4-dihydroxybenzylidene)hydrazinyl) pyrimidin-2-amine | P |
| NCL244 | 4,6-bis(2-((E)-2,3-dihydroxybenzylidene)hydrazinyl) pyrimidin-2-aminium 2-formyl-6-hydroxyphenolate | P |
| NCL245 | 4,6-bis(2-((E)-naphthalen-1-ylmethylene)hydrazinyl) pyrimidin-2-amine | P |
| NCL246 | 4,6-bis(2-((1E,2E)-3-phenylallylidene)hydrazinyl) pyrimidin-2-amine | P |
| NCL247 | 4,6-bis(2-((E)-3,4,5-trihydroxybenzylidene)hydrazinyl) pyrimidin-2-amine | P |
| NCL248 | (E)-2-(naphthalen-1-ylmethylideneamino) guanidine | GM |
| NCL249 | (E)-2-((E)-3-phenylallylideneamino) guanidine | GM |
| NCL250 | (1E,1'E)-N,N'-(ethane-1,2-diyl)bis(1-(4-chlorophenyl)methanimine) | O |
| NCL251 | (1E,1'E)-N,N'-(butane-1,4-diyl)bis(1-(4-chlorophenyl)methanimine) | O |
| NCL252 | (1E,1'E)-N,N'-(propane-1,3-diyl)bis(1-(4-chlorophenyl)methanimine) | O |
| NCL253 | (E)-2-(4-(dimethylamino)benzylideneamino) guanidine | GM |
| NCL254 | (E)-2-(1-(4-chlorophenyl)hexylidene)hydrazine-1-carboximidamide hydrochloride | GM |
| NCL255 | 4,6-bis(2-((E)-[1,1'-biphenyl]-4-ylmethylene)hydrazinyl)pyrimidin-2-amine | P |
| NCL256 | 4,6-bis(2-((E)-2,4-dihydroxybenzylidene)hydrazinyl)pyrimidin-2-amine | P |
| NCL257 | (E)-2-((2-hydroxynaphthalen-1-yl)methylene)hydrazine-1-carboximidamide hydrochloride | GM |
| NCL258 | N1,N4-bis(4-chlorobenzyl)butane-1,4-diamine | O |
| NCL259 | (E)-2-(1-(4-chlorophenyl)-2-cyclohexylethylidene)hydrazine-1-carboximidamide hydrochloride | GM |
| NCL260 | N1,N2-bis(4-chlorobenzyl)ethane-1,2-diamine | O |
| NCL261 | (E)-2-(naphthalen-2-ylmethylene)hydrazine-1-carboximidamide hydrochloride | GM |
| NCL262 | 4,6-bis(2-((E)-3-phenylpropylidene)hydrazinyl)pyrimidin-2-amine | P |
| NCL263 | (E)-2-(2-fluoro-4-(trifluoromethyl)benzylidene)hydrazine-1-carboximidamide hydrochloride | GM |
| NCL264 | 4,6-bis(2-((E)-naphthalen-2-ylmethylene)hydrazinyl)pyrimidin-2-amine | P |
| NCL265 | (E)-2-(1-(4-chlorophenyl)-octylideneamino) guanidine | GM |
| NCL266 | (E)-2-(1-(4-chlorophenyl)-3-cyclopentylpropylideneamino) guanidine | GM |
| NCL267 | (E)-N'-(1-(1H-indol-3-yl)ethylidene)hydrazinecarboximidhydrazide | GM |
| NCL268 | (E)-N'-((E)-1-(1H-indol-3-yl)ethylidene)-2-(1-(1H-indol-3-yl)ethylidene)hydrazine-1-carboximidhydrazide | G |
| NCL269 | (*Z*)-2-(1-(1*H*-indol-3-yl)ethylidene) hydrazine carboximidamide | GM |
| NCL270 | 2,2'-Bis(1-(1H-indol-3-yl)ethylidine) hydrazide carboximidamide | G |
| NCL271 | 2,2'-Bis(1-(4-chlorophenyl)hexylidene) hydrazide carboximidamide | G |
| NCL272 | 2,2'-Bis(1-(4-chlorophenyl)octylidene) hydrazide carboximidamide | G |
| NCL273 | 2,2'-Bis(1-(4-chlorophenyl)-3-cyclopentylpropylidene) hydrazide | G |

FIGURE 2 CONTINUED

| | | |
|---|---|---|
| | carboximidamide | |
| NLC274 | 2,2'-Bis((1*H*-indol-3-yl)methylene) hydrazine carboximidamide | G |
| NCL275 | 2,2'-Bis(1-(4-chlorophenyl)-2-ethoxyethylidene) hydrazide carboximidamide | G |
| NCL276 | (E)-N'-((E)-benzo[c][1,2,5]thiadiazol-4-ylmethylene)-2-(benzo[c][1,2,5]thiadiazol-4-ylmethylene)hydrazine-1-carboximidhydrazide hydrochloride | G |
| NCL277 | (E)-N'-((E)-benzo[c][1,2,5]thiadiazol-5-ylmethylene)-2-(benzo[c][1,2,5]thiadiazol-5-ylmethylene)hydrazine-1-carboximidhydrazide hydrochloride | G |
| NCL278 | (E)-2-(quinoxalin-2-ylmethylene)hydrazine-1-carboximidamide hydrochloride | GM |
| NCL279 | (E)-2-(benzo[d]thiazol-2-ylmethylene)hydrazine-1-carboximidamide hydrochloride | GM |
| NCL280 | (E)-2-(benzo[c][1,2,5]thiadiazol-5-ylmethylene)hydrazine-1-carboximidamide hydrochloride | GM |
| NCL281 | (E)-2-(benzo[c][1,2,5]thiadiazol-4-ylmethylene)hydrazine-1-carboximidamide hydrochloride | GM |
| NCL282 | (E)-N'-((E)-quinolin-6-ylmethylene)-2-(quinolin-6-ylmethylene)hydrazine-1-carboximidhydrazide hydrochloride | G |
| NCL283 | (E)-2-((4-methyl-1H-imidazol-5-yl)methylene)hydrazine-1-carboximidamide hydrochloride | GM |

METHODS AND COMPOSITIONS FOR TREATING FUNGAL INFECTIONS

CROSS-REFERENCE TO RELATED APPLICATIONS

This is a National Stage Entry under 35 U.S.C. 371 of International Patent Application No. PCT/AU2021/050367, filed Apr. 23, 2021, which claims priority to Australian Application No. 2020901286, filed Apr. 24, 2020. These applications are incorporated by reference herein.

TECHNICAL FIELD

This invention relates to methods and compositions for treating and preventing a fungal infection in a subject, methods for preparing a medicament for use in treating and preventing a fungal infection in a subject, and pharmaceutical, veterinary, agricultural and botanical antifungal compositions when used therein.

BACKGROUND ART

"We desperately need new, emerging, effective antifungal agents" (Perfect, J. R. (2016). Is there an emerging need for new antifungals? *Expert Opinion on Emerging Drugs* 21(2): 129-131).

"The development of new antifungal drugs is urgent to improve both human health and agricultural production." (Almeida, F., M. L. Rodrigues and C. Coelho (2019). The Still Underestimated Problem of Fungal Diseases Worldwide. *Frontiers in Microbiology* 10(214)).

The recent rate of emergence of pathogenic fungi that are resistant to the limited number of commonly used antifungal agents is unprecedented. It must not be overlooked that more than 300 million people suffer from serious fungal-related diseases, or that fungi collectively kill in excess of 1.6 million people annually—more than malaria and similar to the tuberculosis death toll. Fungi destroy a third of all food crops each year, sufficient to feed 600 million people. Furthermore, fungal infestation of amphibians has led to the largest disease-caused loss of biodiversity ever recorded, while fungi also cause mass mortality of bats, bees and other animals, and decimate fruit orchards, pine, elm and chestnut forests. To avoid a global collapse in our ability to control fungal infections and to avoid critical failures in medicine and food security, new antifungal discovery is essential.

The Importance of Antifungal Resistance to Human Fungal Infections

Published reports of both actual and attributable mortality to fungal infection in humans estimates that invasive candidiasis has a 30-40% mortality; disseminated cryptococcosis has a 20-30% mortality; and invasive aspergillosis has a similar 20-30% mortality in the presence of azole susceptible infection, but mortality rises dramatically in patients with infection with azole-resistant strains.

New species of multidrug-resistant pathogenic fungi are emerging. *Candida auris*, first described in a patient in Japan in 2009 following isolation from the ear, is responsible for rapidly increasing hospital-acquired invasive infections worldwide. An increasing number of *Candida auris* isolates are resistant to all available clinical antifungals (azoles, polyenes and echinocandins) and present a massive threat to intensive care units where it can survive normal decontamination protocols.

Further to the emergence of *Candida auris*, invasive infection caused by other antifungal-resistant *Candida* spp is increasing alarmingly. Fluconazole resistance among *Candida albicans* isolates is estimated at up to 5%, with the highest rate reported in South Africa. Fluconazole resistance is a much bigger problem among non-*albicans* spp and ranges between 5% and 65%, with the highest rate reported in Denmark. Fluconazole resistance is particularly concerning because it is the only antifungal drug available for treatment of *Candida* infections in many parts of the world. Echinocandin resistance has also been reported, with approximately 6% of *Candida glabrata* isolates in the United States resistant to echinocandins. Multidrug-resistant *Candida* infections have very few remaining treatment options. Among hospitalized patients, candidaemia is the most common form of invasive candidiasis, accounting for 9% of all nosocomial bloodstream infections. Growing evidence suggests that patients who have bloodstream infections with drug-resistant *Candida* spp. are less likely to survive than patients who have candidaemia that can be treated by antifungal medications.

Disseminated *Cryptococcus neoformans* disease causes approximately 1 million cases of cryptococcal meningitis worldwide each year, with more than 600,000 deaths annually. More than 700,000 cases are estimated to occur in sub-Saharan Africa annually.

*Aspergillus* infections cause life-threatening illness in people with weakened immune systems, underlying diseases, or transplant patients. *Aspergillus* is the leading cause of invasive mould infections, with an estimated 200,000 cases worldwide every year. The preferred treatments for these infections are voriconazole and certain other azole drugs. However, in some areas, 12% of *Aspergillus* infections are estimated to be resistant to azole medications. In a large U.S. study, antifungal resistance was identified in up to 7% of *Aspergillus* specimens from patients with stem cell and organ transplants. A multicentre Brazilian study of patients with hematopoietic stem cell transplant and hematologic malignancy reported invasive aspergillosis to be the most common invasive fungal infections, with 6.5% of patients developing the disease.

Therapeutic options for fungal infections are clearly limited—even before considering antifungal resistance. Only three classes of drugs are available to treat systemic *Candida* and *Aspergillus* infections and new antifungals are needed that are broad spectrum and have low toxicity. A recent report from the US Centers for Disease Control and Prevention (Antibiotic resistance threats in the United States, 2019) ranked the most important antimicrobial resistance threats to the human population. Of 21 microbial threats to public health, 3 were listed as due to resistance in fungi; URGENT THREATS *Candida auris*; SERIOUS THREATS Drug-resistant *Candida* (2019 estimate: 34,800 cases & 1,700 deaths; Resistant *Candida* are commonly detected in hospitalized patients. About 7% of bloodstream infections are resistant to antifungals); and WATCH LIST Azole-resistant *Aspergillus fumigatus*.

While invasive fungal infection is the cause of a significant number of human (and animal) deaths, the global burden of fungal infection of the skin and its adnexa, while seldom causing death, is huge. Cutaneous infections are primarily caused by dermatophytes, or fungi with a predilection for the skin. As illustrated in the following table, antifungal resistance among the main dermatophyte species is a widespread and resistance is becoming very common.

TABLE 1

| ANTIFUNGAL CLASS | ANTIFUNGAL AGENT | RESISTANT FUNGAL SPECIES | REFERENCE |
|---|---|---|---|
| Allylamine | Terbinafine | *Trichophyton rubrum* | Digby et al 2017; Osborne et al 2006, 2015; Saunte et al 2019; Schøsler et al 2018; Yamada et al 2017 |
| Allylamine | Terbinafine | *Trichophyton interdigitale* | Hiruma et al 2019; Saunte et al 2019; Yamada et al 2017 |
| Allylamine | Terbinafine | *Trichophyton mentagrophytes* | Ebert et al 2020; Nenoff et al 2019 |
| Azole | Itraconazole | *Trichophyton rubrum* | Monod et al 2019b |
| Azole | Itraconazole | *Trichophyton mentagrophytes* | Ebert et al 2020; Monod 2019b |
| Azole and allylamine | Itraconazole and terbinafine | *Trichophyton mentagrophytes* | Monod 2019a |

The Importance of Antifungal Resistance to Plants in Agriculture and Beyond

The general impact of fungal pathogens on human health goes beyond the ability of fungi to infect humans, since they destroy a third of all food crops annually, causing economical loss and impacting global poverty. Statistics from the 2009-2010 world harvest suggest fungi-induced losses in five of the most important crops globally (rice, wheat, corn, potatoes, and soybean). If those losses were mitigated, these crops would have yielded enough food to feed 8.5% of the seven billion population in 2011. Furthermore, if these five crops were affected by fungal infection simultaneously, approximately 61% of the world's population would not have food.

While fungal infections, particularly those by species of fungi with antifungal resistance, of humans is increasing at a disturbing rate, the world is witnessing the continual emergence of new species of plant-infecting fungi able to survive antifungal treatments, as well as the evolution of antifungal resistance in existing major pathogens of plants. The first case of resistance against the benzimidazole class of fungicide was reported in 1969, and now benzimidazole resistance is known to occur in more than 90 plant pathogens. Azole resistance in a plant pathogen was first reported in 1981. Resistance to the strobilurin class of fungicide was reported in field trials even before commercial introduction. The succinate dehydrogenase inhibitor (SDHI) class of fungicide was introduced in 2007, but by 2017 resistant field isolates were found in 17 pathogen species. Pathogens with resistance to benzimidazoles, azoles, strobilurins, and SDHIs include the major wheat pathogen *Zymoseptoria tritici*, banana black sigatoka pathogen *Mycosphaerella fijiensis*, cereal powdery mildew fungus *Blumeria graminis*, the emerging barley pathogen *Ramularia collo-cygni*, and the apple scab fungus *Venturia inaequalis*. For *Botrytis cinerea*, resistance against 15 different classes of systemic and protectant fungicides has been reported.

Importantly, fungal infections of invertebrate hosts also have a major impact on agriculture. For example, bee broods are susceptible to fungal infections caused by genera of *Ascosphaera* and *Aspergillus*, and agricultural production worldwide is highly dependent on pollination mediated by bees. Fungal infection of bees can precipitate a disaster, with unpreceded impact on agriculture and many other plant species.

It is an object of the present invention to overcome at least one of the failings of the prior art or to provide a commercial alternative.

The discussion of the background art set out above is intended to facilitate an understanding of the present invention only. The discussion is not an acknowledgement or admission that any of the material referred to is or was part of the common general knowledge as at the priority date of the application.

SUMMARY OF INVENTION

According to one aspect of the invention, there is a method of treating or preventing a fungal colonisation or infection in a subject, the method comprising the step of administering a therapeutically effective amount of a compound, or a therapeutically acceptable salt thereof, to the subject, wherein the fungal colonisation or infection is caused by a fungal agent.

Preferably, the compound is a compound of Formula I, or a stereoisomer, tautomer, pharmaceutically acceptable salt, or prodrug thereof:

Formula I

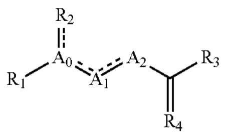

wherein $R_1$ is H, cycloalkyl, Formula II, or Formula III;

Formula II

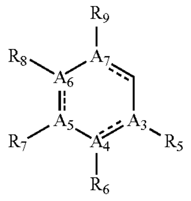

-continued

Formula III

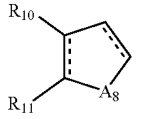

wherein $R_3$ is H, $NH_2$, $NHNH_2$, O—$CH_2$—$CH_3$, NH—C(O)-phenyl, NH-chlorophenyl, NH—$CH_2$-chlorophenyl, NH—N═CH-cycloalkyl, Formula IV, Formula V or Formula VI;

Formula IV

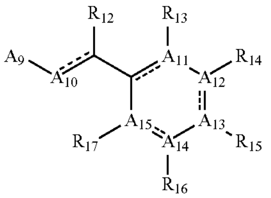

Formula V

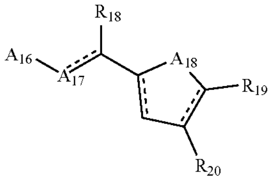

Formula VI

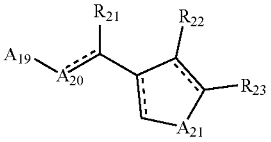

wherein $A_0$ is N, C, CH, or $A_0$ is C and $A_0$ is bonded to $R_4$, via $R_2$, to form a triazole ring;

wherein $A_1$ is N, C, NH, ═CH—CH═N—, ═($C_6H_5$)C—CH═N—, or Formula VII;

Formula VII

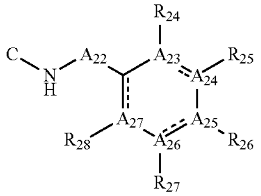

$A_2$ is N, C, NH, N—C(O)-phenyl or Formula VII;

wherein $A_3$, $A_4$, $A_5$, $A_6$, $A_7$, $A_8$, $A_{11}$, $A_{12}$, $A_{13}$, $A_{14}$, $A_{15}$, $A_{16}$, $A_{17}$, $A_{18}$, $A_{19}$, $A_{20}$, $A_{21}$ $A_{23}$, $A_{24}$, $A_{25}$, $A_{26}$ and $A_{27}$ are independently C, O, N, NH, S;

wherein $A_9$ is C, O, N, NH, N—C(O)—O—$CH_2$—$CH_3$, N—C(O)—O—$CH(CH_3)_2$, N—C(O)—NH—$CH_2$—$CH_3$, N—C(O)—NH—$CH_2$-phenyl, N—C(O)—$CH_2$—$CH_2$—$CH_2$—$CH_2$—$CH_2$—$CH_3$, N—C(O)—$CH_2$-furan-2-yl;

wherein $A_{10}$ is C, NH, —N═CH—CH═, —N═CH—C($C_6H_5$)—;

wherein $A_{22}$ is —$CH(CH_3)$—, —N—CH—, —N—C($CH_3$)—, N—C($CH_2OH$)—;

$R_2$ is H, COOH, $CH_2NH_2$, $CH_2OH$, $CH_2NHNH_2$, methyl, ethyl, propyl, butyl, cyclopentyl, or Formula VII and $R_2$ are $R_4$ are bonded together to form a pyrimidine, pyrazine or triazine ring, or $R_2$ and $R_9$ are bonded together to form a pyrrolidinyl oxindole ring;

wherein $R_4$ is N, NH, O, S, or $R_4$ and $A_0$ are bonded, via $R_2$, to form a triazole ring, or $R_4$ is N and $R_4$ and $R_2$ are bonded together to form a pyrimidine ring;

wherein $R_7$ is H, Cl, Br, F, OH, $CH_3$, $OCH_3$, $SCH_3$, CN, CCH, $CF_3$, $OCF_3$, $SCF_3$, $NO_2$, butyl, t-butyl, dimethylamino, phenyl, n-propyl, i-propyl, —NH—C(O)—$CH_3$, —CH═CH—COOH, piperazin-1-yl, or $R_7$ and $R_8$ are bonded together to form a substituted or unsubstituted, saturated or unsaturated aliphatic ring, heterocyclic ring or benzene ring;

wherein $R_6$, $R_8$, $R_{14}$, $R_{16}$, $R_{25}$ and $R_{27}$ are independently H, OH, Cl, F, Br, $CH_3$, CN, $OCH_3$, COOH, $NO_2$, $CF_3$, $R_8$ and $R_7$ bond together to form a substituted or unsubstituted, saturated or unsaturated aliphatic ring, heterocyclic ring, or benzene ring, $R_{14}$ and $R_{15}$ are bonded together to form a substituted or unsubstituted, saturated or unsaturated aliphatic ring, heterocyclic ring or benzene ring, $R_8$ and $R_9$ are bonded together to form a substituted or unsubstituted, saturated or unsaturated aliphatic ring, heterocyclic ring or benzene ring, or $R_{14}$ and $R_{13}$ are bonded together to form a substituted or unsubstituted saturated or unsaturated aliphatic ring, heterocyclic ring or benzene ring;

wherein $R_5$, $R_9$, $R_{17}$, $R_{24}$ and $R_{28}$ are independently H, O, OH, Cl, F, Br, $NH_2$, $CH_3$, $CF_3$, $OCH_3$, CN, $NO_2$, phenyl, —NH—CH(OH)—$CH_3$, —NH—C(O)—$CH_3$, or $R_9$ and $R_8$ are bonded together to form a substituted or unsubstituted, saturated or unsaturated aliphatic ring, heterocyclic ring or benzene ring, or $R_{13}$ and $R_{14}$ are bonded together to form a substituted or unsubstituted saturated or unsaturated aliphatic ring, heterocyclic ring or benzene ring;

wherein $R_{10}$, $R_{11}$, $R_{19}$, $R_{20}$, $R_{22}$ and $R_{23}$ are independently H, Cl, or Br, or $R_{10}$ and $R_{11}$ are bonded together to form a substituted or unsubstituted, saturated or unsaturated aliphatic ring, heterocyclic ring or benzene ring, or $R_{19}$ and $R_{20}$ are bonded together to form a substituted or unsubstituted, saturated or unsaturated aliphatic ring, heterocyclic ring or benzene ring, or $R_{22}$ and $R_{23}$ are bonded together to form a substituted or unsubstituted, saturated or unsaturated aliphatic ring, heterocyclic ring or benzene ring;

wherein $R_{12}$, $R_{18}$ and $R_{21}$ are independently H, COOH, $CH_2NH_2$, $CH_2OH$, methyl, ethyl, propyl, butyl, cyclopentyl, or $R_{12}$ and $R_{13}$ are bonded together to form a pyrrolidinyl oxindole ring;

wherein $R_{15}$ and $R_{26}$ are independently H, Cl, Br, F, OH, $CH_3$, $OCH_3$, $SCH_3$, CN, $CF_3$, $OCF_3$, $SCF_3$, $NO_2$, CCH, n-butyl, t-butyl, dimethylamino, phenyl, n-propyl, i-propyl, —NH—C(O)—$CH_3$, —CH═CH—COOH, piperazin-1-yl, or $R_{15}$ and $R_{14}$ are bonded together to form a substituted or unsubstituted, saturated or unsaturated aliphatic ring, heterocyclic ring or benzene ring; and wherein "----" is a double bond or a single bond.

Preferably, the compound is a compound of Formula I, or a stereoisomer, tautomer, pharmaceutically acceptable salt, or prodrug thereof, wherein $A_0$ is C;

wherein $A_1$ is N; or Formula VII;

wherein $A_2$ is N; or NH;

wherein $A_3$, $A_4$, $A_6$, $A_7$, $A_{11}$, $A_{12}$, $A_{14}$, $A_{15}$, are N; or C;

wherein $A_5$, $A_{13}$, $A_{23}$, $A_{24}$, $A_{25}$, $A_{26}$ and $A_{27}$ are C;

wherein $A_8$ and $A_{21}$ are S;

wherein $A_9$ is NH;

wherein $A_{10}$ is N;

wherein $A_{22}$ is —N—CH—; —N—C($CH_3$)—; or —N—C($CH_2OH$)—;

wherein $R_1$ is H; Formula II; Formula III; cycloalkyl;

wherein $R_2$ is H; methyl; ethyl; $CH_2NHNH_2$; $CH_2OH$; butyl; cyclopentyl; or Formula VII and $R_2$ is bonded to $R_4$, to form a pyrimidine ring;

wherein $R_3$ is $NH_2$; Formula IV; Formula V; Formula VI; $NH_2$, NH—N=CH-cycloalkyl; or O—$CH_2$—$CH_3$;

wherein $R_4$ is NH; O; S; or $R_4$ is N and $R_4$ and $R_2$ are bonded together to form a pyrimidine ring;

wherein $R_7$ is H; F; Cl; $CF_3$; methyl; $R_7$ and $R_8$ are bonded together to form an unsubstituted, benzene ring; OH; t-butyl; phenyl; dimethylamino; i-propyl; n-propyl; CN; CCH; n-butyl; $SCH_3$; $R_7$ and $R_8$ are bonded together to form an unsubstituted, unsaturated heterocyclic ring; $OCH_3$; Br; $OCF_3$; piperazin-1-yl; or $SCF_3$;

wherein $R_6$, $R_8$, $R_{14}$, and $R_{16}$ are independently H; OH; F; $OCH_3$; $CF_3$; methyl; Cl; CN; Br; $R_8$ and $R_7$ are bonded together to form an unsubstituted, benzene ring; $R_8$ and $R_7$ are bonded together to form an unsubstituted, unsaturated heterocyclic ring; $R_{14}$ and $R_{15}$ are bonded together to form an unsubstituted, benzene ring; or $R_{14}$ and $R_{15}$ are bonded together to form an unsubstituted, unsaturated heterocyclic ring;

wherein $R_5$, $R_9$, $R_{13}$, and $R_{17}$ are independently H; OH; $NH_2$; Cl; F; $OCH_3$; OH; —NH—CH(OH)—$CH_3$;

wherein $R_{12}$ is H; methyl; ethyl; $CH_2OH$; or cyclopentyl;

wherein $R_{15}$ is H; F; Cl; $CF_3$; methyl; $R_{15}$ and $R_{14}$ are bonded together to form an unsubstituted, benzene ring; OH; t-butyl; phenyl; dimethylamino; i-propyl; n-propyl; CN; CCH; n-butyl; $SCH_3$; $R_{15}$ and $R_{14}$ are bonded together to form an unsubstituted, unsaturated heterocyclic ring; $OCH_3$; Br; $OCF_3$; piperazin-1-yl; or $SCF_3$;

wherein $R_{24}$ and $R_{28}$ are independently H; OH; or Cl;

wherein $R_{25}$ and $R_{27}$ are independently H; or OH;

wherein $R_{26}$ is H; $CH_3$; Br; Cl; OH; dimethylamino; —O—P(O)$(OEt)_2$; $CF_3$; or F; and wherein "----" is independently a single or a double bond.

Preferably, the compound is selected from the compounds presented in FIG. 1. Preferably, the compound is selected from the compounds presented in FIG. 2, wherein the compound is selected from the group comprising: Group G—Guanidine, Group GM—Guanidine Monomer, Group P—Pyrimidine or Group O—Other.

More preferably, the compound is selected from the group comprising: NCL021; NCL023; NCL027; NCL038; NCL039; NCL040; NCL054; NCL062; NCL097; NCL101; NCL105; NCL107; NCL113; NCL115; NCL121; NCL123; NCL126; NCL129; NCL130; NCL131; NCL132; NCL133; NCL134; NCL135; NCL136; NCL137; NCL138; NCL139; NCL140; NCL141; NCL143; NCL144; NCL145; NCL146; NCL147; NCL148; NCL149; NCL150; NCL151; NCL152; NCL153; NCL154; NCL155; NCL156; NCL160; NCL162; NCL163; NCL166; NCL167; NCL170; NCL171; NCL172; NCL175; NCL177; NCL178; NCL179; NCL180; NCL181; NCL184; NCL185; NCL187; NCL188; NCL189; NCL190; NCL192; NCL193; NCL195; NCL196; NCL197; NCL198; NCL199; NCL201; NCL202; NCL203; NCL204; NCL205; NCL206; NCL207; NCL208; NCL211; NCL212; NCL213; NCL214; NCL215; NCL216; NCL217; NCL218; NCL219; NCL220; NCL221; NCL222; NCL223; NCL224; NCL225; NCL226; NCL227; NCL228; NCL229; NCL230; NCL231; NCL232; NCL233; NCL234; NCL235; NCL236; NCL237; NCL238; NCL239; NCL241; NCL242; NCL243; NCL244; NCL245; NCL246; NCL247; NCL248; NCL249; NCL250; NCL252; NCL253; NCL254; NCL255; NCL256; NCL258; NCL259; NCL260; NCL261; NCL262; NCL263; NCL264; NCL265; NCL266; NCL267; NCL268; NCL269; NCL270; NCL271; NCL272; NCL273; NCL274; NCL275; NCL276; NCL277; NCL278; NCL279; NCL280; NCL281; NCL282; NCL283; and NCL812.

Even more preferably, the compound is selected from the group comprising: NCL021; NCL097; NCL139; NCL282; NCL812; NCL123; NCL134; NCL140; NCL150; NCL160; NCL195; NCL228; NCL271; NCL038; NCL105; NCL107; NCL171; NCL247; NCL265; NCL274; NCL039; NCL054; NCL113; NCL121; NCL126; NCL146; NCL217; NCL266; NCL268; NCL023; NCL027; NCL040; NCL254; NCL259; NCL101; NCL243; NCL062; NCL115; NCL219; and NCL220.

Even more preferably, the compound is selected from the group comprising: NCL021; NCL038; NCL097; NCL105; NCL107; NCL123; NCL126; NCL134; NCL139; NCL140; NCL150; NCL160; NCL171; NCL195; NCL217; NCL228; NCL247; NCL265; NCL266; NCL268; NCL271; NCL274; NCL282; and NCL812.

Even more preferably, the compound is selected from the group comprising: NCL021; NCL097; NCL123; NCL134; NCL139; NCL140; NCL150; NCL160; NCL195; NCL228; NCL271; NCL282; and NCL812.

Even more preferably, the compound is selected from the group comprising: NCL097; NCL123; NCL139; NCL140; NCL150; NCL195; NCL228; NCL271; NCL282; and NCL812.

Preferably the compound is not NCL279.

Preferably, the compound has antifungal activity and antibacterial activity.

In one alternative, the compound has antifungal activity and no observed antibacterial activity.

The present invention further provides a method of treating or preventing a fungal colonisation or infection in a subject, the method comprising the step of administering a therapeutically effective amount of the compound robenidine (NCL812) or a therapeutically acceptable salt thereof and EDTA or a therapeutically acceptable salt thereof, to the subject, wherein the fungal colonisation or infection is caused by a fungal agent. In one preferred embodiment, the compound is administered to the subject together with a combination of EDTA or a therapeutically effective salt thereof and tetracaine or a therapeutically effective salt thereof.

Preferably, the fungal agent is a pathogen of terrestrial animals (including humans), fish, insects or plants.

Preferably, the fungal agent is selected from the group comprising: *Absidia* spp.; *Acremonium* spp.; *Actinomucor* spp.; *Albugo candida; Alternaria alternata; Alternaria brassicae; Alternaria brassicicola; Alternaria helianthi; Alternaria solani; Alternaria* spp.; *Apophysomyces elegans; Armillaria* spp.; *Ascochyta pisi; Ascosphaera apis; Aspergillus* spp.; *Aspergillus alabamensis; Aspergillus algerae; Aspergillus alliaceus* (teleomorph *Petromyces alliaceus*); *Aspergillus avenaceus; Aspergillus caesiellus; Aspergillus calidoustus; Aspergillus candidus; Aspergillus carneus; Aspergillus clavatus; Aspergillus connori; Aspergillus flavipes; Aspergillus flavus; Aspergillus fumigatus; Aspergillus glaucus; Aspergillus granulosus; Aspergillus insuetus; Aspergillus keveii; Aspergillus lentulus; Aspergillus nidulans* (*Emericella nidulans*); *Aspergillus niger, Aspergillus novofumigatus; Aspergillus ochraceus; Aspergillus pseudodeflectus; Aspergillus puniceus; Aspergillus quadrilineatus; Aspergillus restrictus; Aspergillus sydowii; Aspergillus tam-*

*arii; Aspergillus tanneri; Aspergillus terreus; Aspergillus thermomutatus* (teleomorph *Neosartorya pseudofischeri*); *Aspergillus tubingensis; Aspergillus udagawae* (*Neosartorya udagawae*); *Aspergillus versicolor; Aspergillus vesicularum; Aspergillus viridinutans; Aspergillus vitus* (teleomorph *Eurotium amstelodami*); *Aspergillus wentii; Austropuccinia psidii* (formerly *Puccinia psidii*, initially identified as *Uredo rangelii*); *Basidiobolus* spp.; *Batrachochytrium dendrobatidis; Batrachochytrium salamandrivorans; Biatriospora* spp.; *Bipolaris* spp.; *Bipolaris maydis; Bipolaris zeicola; Blastomyces dermatitidis; Blastomyces gilchristii; Blastomyces helicus; Blastomyces parvus; Blastomyces percursus; Blastomyces silverae; Blumeria graminis; Blumeriella jaapii; Botryosphaeria obtusa; Botrytis* spp.; *Botrytis allii; Botrytis cinerea; Botrytis elliptica; Botrytis squamosa; Branchiomyces demigrans; Branchiomyces sanguinis; Bremia lactucae; Candida africana; Candida albicans; Candida auris; Candida bracarensis; Candida dubliniensis; Candida duobushaemulonii; Candida famata; Candida glabrata* (formerly classified as *Torulopsis glabrata*); *Candida guilliermondii; Candida haemulonii* var. *vulnera; Candida inconspicua; Candida krusei; Candida lusitaniae; Candida metapsilosis; Candida metapsilosis; Candida nivariensis; Candida orthopsilosis; Candida orthopsilosis; Candida pseudotropicalis; Candida rugosa; Candida tropicalis; Cercospora* spp.; *Cercospora beticola; Cercospora kikuchii; Cercospora sojina; Chrysosporium* spp.; *Cladophialophora* spp.; *Cladophialophora bantiana; Cladophialophora carrionii; Coccidioides immitis; Coccidioides posadasii; Cochliobolus carbonum; Cochliobolus miyabeanus; Colletotrichum* spp. (sexual stage: *Glomerella*); *Colletotrichum acutatum; Colletotrichum gloeosporoides; Conidiobolus* spp.; *Conidiobolus coronatus; Conidiobolus incongruous; Corynespora cassiicola; Cronartium ribicola; Cryptococcus bacillisporus; Cryptococcus decagattii; Cryptococcus deuterogattii; Cryptococcus gattii; Cryptococcus neoformans; Cryptococcus neoformans* var. *grubli* (serotype A); *Cryptococcus neoformans* var. *neoformans; Cryptococcus tetragattii; Cunninghamella bertholletiae; Curvularia* spp.; *Diaporthe helianthi; Diaporthe phaseolorum; Diplocarpon mespili; Drepanopeziza ribis; Dydimella bryoniae; Elsinoe* spp.; *Emergomyces africanus; Emmonsia* spp.; *Emmonsia parva; Epidermophyton* spp.; *Erysiphe cruciferarum; Erysiphe graminis* (*Blumeria graminis*); *Erysiphe heraclei; Erysiphe necator**; *Eutypa lata; Exophiala* spp.; *Exserohilum* spp.; *Falciformispora* spp.; *Fonsecaea* spp.; *Fonsecaea monophora; Fonsecaea nubica; Fonsecaea pedrosoi; Fusarium* spp.; *Fusarium fujikuroi; Fusarium graminearum; Fusarium oxysporum; Fusarium oxysporum; Fusarium solani; Gaeumannomyces graminis; Geomyces* spp.; *Geosmithia* spp.; *Geotrichum* spp.; *Gibberella fujikuori; Gloeodes pomigena; Glomerella cingulata* (anamorph: *Gloeosporium fructigenum*); *Gnomonia erythrostoma; Gnomonia leptostyla; Guignardia bidwellii; Gymnosporangium sabinae; Helminthosporium* spp.; *Helminthosporium solani; Hemileia vastatrix; Histoplasma capsulatum; Hypomyces rosellus* (*Dactylium dendroides*); *Icthyophonus hoferi; Kabatiella zeae; Lacazia loboi; Lagenidium* spp.; *Leptosphaeria biglobosa; Leptosphaeria maculans; Leptothyrium pomi; Leveillula taurica; Lichtheimia* (*Absidia*) *corymbifera; Lomentospora* (formerly *Scedosporium*) *prolificans; Macrophomina* spp.; *Madurella* spp.; *Magnaporthe* spp.; *Magnaporthe oryzae; Magnusiomyces capitatus* (formerly called *Saprochaete capitata* and *Blastoschizomyces capitatus*); *Malassezia* spp. (previously *Pityrosporum* spp.); *Malassezia caprae; Malassezia dermatis; Malassezia equina; Malassezia furfur; Malassezia globosa; Malassezia japonica; Malassezia nana; Malassezia obtusa; Malassezia pachydermatis; Malassezia restricta; Malassezia slooffiae; Malassezia sympodialis; Malassezia yamatoensis; Medicopsis* spp.; *Melampsora* spp.; *Melampsora lini; Metarhizium* spp.; *Microsphaeropsis arundinis; Microsporum* spp.; *Microsporum canis; Microsporum gypseum; Microsporum persicolor; Moniliella* spp.; *Monilinia* spp.; *Monocillium indicum; Monographella nivale; Mucor* spp.; *Mucor circinelloides; Mucor velutinosus; Mycosphaerella* spp.; *Mycosphaerella brassicicola; Mycosphaerella fijiensis; Mycosphaerella graminicola; Mycosphaerella graminicola* (*Zymoseptoria tritici*); *Mycosphaerella musicola; Mycosphaerella nawae; Mycosphaerella pinodes; Mycovellosiella nattrassii; Nannizzia* spp.; *Nectria galligena; Neofabraea malicorticis* (anamorph: *Gloeosporium malicorticis*); *Neofabraea perennans* (anamorph: *Gloeosporium perennans*); *Neofabraea vagabunda* (anamorph: *Gloeosporium album*); *Neotestudina rosatii; Ochroconis* spp.; *Oculimacula* spp.; *Oidium neolycopersici; Paecilomyces* spp. (incl *Paecilomyces farinosis*); *Paracoccidioides americana; Paracoccidioides brasiliensis; Paracoccidioides lutzii; Paracoccidioides restrepiensis; Paracoccidioides venezueliensis; Parastagonospora nodorum* (*Stagonospora*); *Penicillium* spp.; *Penicillium digitatum; Penicillium expansum; Phaeoacremonium* spp.; *Phaeoacremonium aleophilum; Phaeomoniella chlamydospora; Phakopsora* spp.; *Phakopsora pachyrhizi; Phialemonium* spp.; *Phialophora* spp.; *Phialophora verrucose; Phoma* spp.; *Phoma macdonaldii; Phomopsis viticola; Phytophthora cactorum; Phytophthora fragariae; Phytophthora infestans; Phytophthora rubi; Pichia anomala; Plasmopara viticola; Pleurostomophora ochracea; Pneumocystis carinii; Pneumocystis jirovecii; Pneumocystis murina; Podosphaera leucotricha; Podosphaera xanthii; Prototheca wickerhamii; Prototheca zopfii; Pseudallescheria* spp.; *Pseudocercospora* (*Mycosphaerella*) *fijiensis; Pseudocercosporella herpotrichoides; Pseudochaetosphaeroma* spp.; *Pseudogymnoascus destructans* (formerly known as *Geomyces destructans; Pseudomicrodochium* spp.; *Pseudoperonospora cubensis; Pseudopezicula tracheiphila* (*Pseudopeziza*); *Puccinia* spp.; *Puccinia sorghi; Pyrenophora teres; Pyricularia oryzae; Pythium* spp.; *Pythium insidiosum; Ramularia collocygni; Rhinocladiella aquaspersa; Rhinosporidium seeberi; Rhizoctonia* spp.; *Rhizoctonia solani; Rhizomucor* spp.; *Rhizomucor pusifius; Rhizopus* spp.; *Rhizopus arrhizus* (*Rhizopus oryzae*); *Rhizopus microsporus; Rhizopus rhizopodoformis; Rhizopus stolonifer; Rhodotorula* spp.; *Rhynchosporium commune* (*secalis*); *Rhynchosporium secalis; Rhytidhysteron* spp.; *Roussoella* spp.; *Saccharomyces cerevisiae; Saksenaea vasiformis; Saprolegnia* spp.; *Scedosporium apiospermum; Scedosporium aurantiacum; Scedosporium boydii* (formerly *Pseudallescheria boydii*); *Schizophyllum commune; Sclerotinia* spp.; *Scierotinia sclerotiorum; Sclerotium* spp.; *Scolecobasidium* spp.; *Septoria* spp.; *Septoria nodorum; Septoria piricola; Septoria tritici; Sphaerotheca fuliginea; Sphaerulina oryzina; Sporothrix brasiliensis; Sporothrix globose; Sporothrix luriei; Sporothrix mexicana; Sporothrix pafiida; Sporothrix schenckii; Staphylotrichum coccosporum; Stemphyfiium* spp.; *Syncephalastrum racemosum; Talaromyces* (*Penicillium*) *marneffei; Taphrina deformans; Thielaviopsis* spp.; *Tilletia* spp.; *Tranzschelia* spp.; *Trematosphaeria* spp.; *Trichophyton* spp.; *Trichophyton erinacei; Trichosporon* spp.; *Trichosporon asahii; Trichosporon asahii; Trichosporon cutaneum; Trichosporon domesticum; Trichosporon loubieri; Trichosporon pullulans; Ulocladium* spp.; *Uncinula necator; Uro-*

*myces* spp.; *Ustilago* spp.; *Ustilago maydis; Venturia inaequalis; Verticillium* spp.; and *Wangiella* spp.

Preferably, the fungal agent is selected from the group comprising: *Alternaria solani; Armillaria* spp.; *Ascosphaera apis; Aspergillus* spp.; *Aspergillus fumigatus; Blastomyces dermatitidis; Blumeria graminis; Botrytis* spp.; *Branchiomyces demigrans; Branchiomyces sanguinis; Candida albicans; Candida auris; Cercospora* spp.; *Coccidioides immitis; Colletotrichum* spp. (sexual stage: *Glomerella*); *Cryptococcus gattii; Cryptococcus neoformans; Epidermophyton* spp.; *Erysiphe graminis* (*Blumeria graminis*); *Fusarium* spp.; *Fusarium graminearum; Fusarium oxysporum; Gaeumannomyces graminis; Helminthosporium* spp.; *Histoplasma capsulatum; lcthyophonus hoferi; Magnaporthe oryzae; Malassezia* spp. (previously *Pityrosporum* spp.); *Melampsora* spp.; *Microsporum* spp.; *Microsporum canis; Microsporum gypseum; Mycosphaerella* spp.; *Phakopsora* spp.; *Pneumocystis carinii; Pneumocystis jirovecfi; Pseudocercosporella herpotrichoides; Pseudoperonospora cubensis; Puccinia* spp.; *Pyrenophora teres; Pyricularia oryzae; Pythium* spp.; *Rhinosporidium seeberi; Rhizoctonia* spp.; *Rhynchosporium secalis; Saprolegnia* spp.; *Sclerotinia* spp.; *Septoria* spp.; *Sphaerotheca fuliginea; Sporothrix schenckii; Thielaviopsis* spp.; *Tilletia* spp.; *Trichophyton* spp.; *Trichophyton erinacei; Uncinula necator; Ustilago* spp.; *Venturia inaequalis*; and *Verticillium* spp.

Preferably, the fungal agent is selected from the group comprising: *Ascosphaera apis; Aspergillus* spp.; *Aspergillus fumigatus; Blumeria graminis; Botrytis* spp.; *Branchiomyces demigrans; Branchiomyces sanguinis; Candida albicans; Candida auris; Colletotrichum* spp. (sexual stage: *Glomerella*); *Cryptococcus gattii; Cryptococcus neoformans; Epidermophyton* spp.; *Fusarium* spp.; *Fusarium graminearum; Fusarium oxysporum; Histoplasma capsulatum; Icthyophonus hoferi; Magnaporthe oryzae; Malassezia* spp. (previously *Pityrosporum* spp.); *Melampsora* spp.; *Microsporum* spp.; *Mycosphaerella* spp.; *Phakopsora* spp.; *Pneumocystis jirovecfi; Puccinia* spp.; *Rhizoctonia* spp.; *Saprolegnia* spp.; *Sporothrix schenckii; Trichophyton* spp.; and *Ustilago* spp.

Preferably, the subject is selected from the group comprising: human, canine, feline, bovine, ovine, caprine, porcine, equine, chiropteran, avian, piscine, amphibian, and insect species.

Preferably, the compound is administered utilising a route selected from the group comprising: oral route, injection route, subcutaneous route, intramuscular route, intravenous route, intraperitoneal, intraosseous, intrathecal route, intraventricular, sublingual route, buccal routes, rectal route, vaginal route, ocular route, otic route, nasal route, inhalation route, nebulization route, cutaneous route and transdermal route.

Preferably, the subject is a botanical subject.

Preferably, the subject is selected from the group comprising: tree, timber, herb, vegetable, fruit, berry, bush, grass, seed, seedling, potted plant or vine.

Preferably, the compound is administered to the subject by enteral or parenteral routes at a dose range selected from the group consisting of: 0.1 mg/kg to 250 mg/kg; and 5 mg/kg to 50 mg/kg subject weight.

Preferably, the compound is administered to the subject utilising a dosing regimen selected from the group consisting of: at a frequency to alleviate the signs or symptoms of the infection, twice hourly, once every six hours, once every 12 hours, once daily, twice weekly, once weekly, once every two weeks, once a month, every two months, once every six months, once yearly.

Preferably, the compound is administered to the subject together with a further antifungal agent or fungicide, an insecticide or an antibacterial agent.

In a further aspect of the invention, there is an antifungal pharmaceutical composition comprising a therapeutically effective amount of the compound, or a therapeutically acceptable salt thereof, and optionally a pharmaceutically acceptable excipient or carrier. Preferably, the composition is a dosage form.

The present invention further provides an antifungal pharmaceutical composition comprising a therapeutically effective amount of the compound robenidine (NCL812) or a therapeutically acceptable salt thereof and EDTA or a therapeutically acceptable salt thereof, and optionally a pharmaceutically acceptable excipient or carrier. Preferably, the composition is a dosage form. In one preferred embodiment, the composition further comprises tetracaine or a therapeutically effective salt thereof.

Preferably, the composition is a tablet, capsule, wafer, suppository, liquid, cream, ointment, paste, powder, gel, solution, wettable powder, shampoo, spray, patch, suspension, bath or dip.

Preferably, the composition comprises a further antifungal agent or fungicide, an insecticide or an antibacterial agent.

In a further aspect of the invention, there is an antifungal veterinary composition comprising a therapeutically effective amount of the compound, or a therapeutically acceptable salt thereof, and optionally a veterinary acceptable excipient or carrier. Preferably, the composition is a dosage form.

The present invention further provides an antifungal veterinary composition comprising a therapeutically effective amount of the compound robenidine (NCL812) or a therapeutically acceptable salt thereof and EDTA or a therapeutically acceptable salt thereof, and optionally a pharmaceutically acceptable excipient or carrier. Preferably, the composition is a dosage form. Preferably, the composition is a tablet, capsule, wafer, suppository, liquid, cream, ointment, paste, powder, gel, solution, wettable powder, shampoo, spray, patch, suspension, bath or dip. In one preferred embodiment, the composition further comprises tetracaine or a therapeutically effective salt thereof.

Preferably, the composition comprises a further antifungal agent or fungicide, an insecticide or an antibacterial agent.

In a further aspect of the invention, there is an antifungal botanical composition comprising a therapeutically effective amount of the compound, or a therapeutically acceptable salt thereof, and optionally a botanically acceptable excipient or carrier. Preferably, the composition is a dosage form.

Preferably, the composition is a liquid, cream, ointment, powder, gel, solution, spray, suspension, suspension concentrate, emulsifiable concentrate, flowable concentrate, dry flowable, wettable powder, granule, water dispersible granule, seed treatment or dip.

Preferably, the composition comprises a further antifungal agent or fungicide, an insecticide or an antibacterial agent.

In a further aspect of the invention, there is a use of a compound, or a therapeutically acceptable salt thereof, in the manufacture of a medicament for the treatment of a fungal colonisation or infection in a subject.

The present invention further provides use of the compound robenidine (NCL812) or a therapeutically acceptable salt thereof and EDTA or a therapeutically acceptable salt thereof, in the manufacture of a medicament for the treatment of a fungal colonisation or infection in a subject. In one preferred embodiment, the medicament further comprises tetracaine or a therapeutically effective salt thereof.

Preferably, the use comprises administering a therapeutically effective amount of the compound, or a therapeutically acceptable salt thereof, to the subject.

Preferably, the compound is administered to the subject selected from the group consisting of: 0.1 mg/kg to 250 mg/kg; and 5 mg/kg to 50 mg/kg subject weight.

In a further aspect of the invention, there is a medical device when used in a method of treating or preventing a fungal colonisation or infection in the subject, wherein the medical device comprises the pharmaceutical composition.

In a further aspect of the invention, there is a veterinary device when used in a method of treating or preventing a fungal colonisation or infection in the subject, wherein the veterinary device comprises the veterinary composition.

In a further aspect of the invention, there is a botanical device when used in a method of treating or preventing a fungal colonisation or infection in the subject, wherein the botanical device comprises the botanical composition.

In a further aspect of the invention, there is a method of killing fungi, the method including the step of contacting the fungi with a compound, or a therapeutically acceptable salt thereof.

In a further aspect of the invention, there is a use of a compound, or a therapeutically acceptable salt thereof, to kill or inhibit the growth or reproduction of fungi, said use comprising the step of contacting the fungi with the compound, or a therapeutically acceptable salt thereof.

In a further aspect of the invention, there is a compound, or a therapeutically acceptable salt thereof, wherein the compound is NCL276, NCL277, NCL278, NCL279, NCL280, NCL281, NCL282 or NCL283. Preferably the compound is not NCL279.

In a further aspect of the invention, there is a method of improving or increasing the antifungal activity of a composition comprising NCL812 (robenidine) or a therapeutically effective salt thereof, said method comprising adding to the composition an effective amount of EDTA or a therapeutically effective salt thereof, and optionally a pharmaceutically acceptable excipient or carrier. Preferably, there is a synergistic interaction between NCL812 or its therapeutically effective salt thereof; and EDTA or its therapeutically effective salt thereof. In one preferred embodiment, the composition further comprises tetracaine or a therapeutically effective salt thereof.

In a further aspect of the invention, there is use of EDTA or its therapeutically effective salt thereof to improve or increase the antifungal activity of a composition comprising NCL812 (robenidine) or a therapeutically effective salt thereof. In one preferred embodiment, the composition further comprises tetracaine or a therapeutically effective salt thereof.

Terms used herein will have their customary meanings in the art unless specified.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 1 shows a table of compounds NCL276 to NCL283, together with their chemical name and structure. The structures of compounds NCL001-NCL275 can be found in PCT/AU2015/000527.

FIG. 2 shows a table of compounds NCL001 to NCL283, and NCL812, together with their chemical name and their classification into the following groups: G—Guanidine, GM—Guanidine monomer, P—Pyrimidine, and O—Other.

DESCRIPTION OF EMBODIMENTS

General

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional microbiological techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The pharmaceutical for veterinary compositions of the invention may be administered in a variety of unit dosages depending on the method of administration, target site, physiological state of the patient, and other medicaments administered. For example, unit dosage form suitable for oral administration include solid dosage forms such as powder, tablets, pills, and capsules, and liquid dosage forms, such as elixirs, syrups, solutions and suspensions. The active ingredients may also be administered parenterally in sterile liquid dosage forms. Gelatin capsules may contain the active ingredient and inactive ingredients such as powder carriers, glucose, lactose, sucrose, mannitol, starch, cellulose or cellulose derivatives, magnesium stearate, stearic acid, sodium saccharin, talcum, magnesium carbonate, and the like.

The phrase "pharmaceutically acceptable carrier" as used herein can include: surfactants and polymers including, but not limited to polyethylene glycol (PEG), polyvinylpyrrolidone (PVP), polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate; binding agents such as various celluloses and cross-linked polyvinylpyrrolidone, microcrystalline cellulose; and or; filling agents such as lactose monohydrate, lactose anhydrous, microcrystalline cellulose and various starches; and or lubricating agents such as agents that act on the flowability of the powder to be compressed, including colloidal silicon dioxide, talc, stearic acid, magnesium stearate, calcium stearate, silica gel; and or sweeteners such as any natural or artificial sweetener including sucrose, xylitol, sodium saccharin, cyclamate, aspartame, and accsulfame K; and or flavouring agents; and or preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride; and or buffers; and or Diluents such as pharmaceutically acceptable inert fillers, such as microcrystalline cellulose, lactose, dibasic calcium phosphate, saccharides, and/or mixtures of any of the foregoing; and or wetting agents such as corn starch, potato starch, maize starch, and modified starches, croscarmellose sodium, crosspovidone, sodium starch glycolate, and mixtures thereof; and or disintegrants; and or effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or other pharmaceutically acceptable excipients.

In a highly preferred form, the invention is a pharmaceutical or veterinal composition, comprising either:

TABLE 2

| Constituent | Aqueous formulation | Non-aqueous formulation |
|---|---|---|
| Compound of Invention | 0.1-10 mg/g | 0.1-10 mg/g |
| EDTA Disodium | 1-100 mg/g | 1-100 mg/g |
| Tetracaine | 1-100 mg/g | 1-100 mg/g |
| Hydroxy Ethyl Cellulose | 0.1-5 w/w | — |
| Water | Up to 100% w/w | — |
| Aerosil R972 Pharma | — | 1-20% w/w |
| Miglyol 812 | — | Up to 100% w/w |

In an even more highly preferred form, the invention is a pharmaceutical or veterinal composition, comprising either:

TABLE 3

| Constituent | Aqueous formulation | Non-aqueous formulation |
|---|---|---|
| Compound of Invention | 1 mg/g | 1 mg/g |
| EDTA Disodium | 40 mg/g | 40 mg/g |
| Tetracaine | 40 mg/g | 40 mg/g |
| Hydroxy Ethyl Cellulose | 3% w/w | — |
| Water | Up to 100% w/w | — |
| Aerosil R972 Pharma | — | 13% w/w |
| Miglyol 812 | — | Up to 100% w/w |

or

TABLE 4

| Constituent | Aqueous formulation | Non-aqueous formulation |
|---|---|---|
| Compound of Invention | 1 mg/g | 1 mg/g |
| EDTA Disodium | 40 mg/g | 40 mg/g |
| Tetracaine | 40 mg/g | 40 mg/g |
| Hydroxy Ethyl Cellulose | 2.5% w/w | — |
| Water | Up to 100% w/w | — |
| Aerosil R972 Pharma | — | 4.5% w/w |
| Miglyol 812 | — | Up to 100% w/w |

The phrase "therapeutically effective amount" as used herein refers to an amount sufficient to inhibit fungal growth associated with a fungal infection or colonisation. That is, reference to the administration of the therapeutically effective amount of compound according to the methods or compositions of the invention refers to a therapeutic effect in which substantial fungicidal or fungistatic activity causes a substantial inhibition of fungal infection. The term "therapeutically effective amount" as used herein, refers to a sufficient amount of the composition to provide the desired biological, therapeutic, and/or prophylactic result. The desired results include elimination of fungal infection or colonisation or reduction and/or alleviation of the signs, symptoms, or causes of a disease, or any other desired alteration of a biological system. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the composition used and the route of administration employed. Effective amounts are routinely optimized taking into consideration pharmacokinetic and pharmacodynamic characteristics as well as various factors of a particular patient, such as age, weight, gender, etc and the area affected by disease or disease causing fungi.

The compounds of the invention present within the compositions (pharmaceutical, veterinary, botanical) of the invention are present at a concentration of between about 0.1% and about 99.0% by weight. Preferably, the concentration of pharmaceutically acceptable materials within the compositions will be about 5% to about 80% by weight, while concentrations of 10% to about 50% by weight are highly preferred. Desirably, the concentration will be in the range of about 10 to 15% by weight, 15 to 20% by weight, 20 to 25% by weight, 25 to 30% by weight, 30 to 35% by weight, 35 to 40% by weight, 40 to 45% by weight, 45 to 50% by weight, 50 to 55% by weight, 55 to 60% by weight, 60 to 65% by weight, 65 to 70% by weight, 70 to 75% by weight or 75 to 80% by weight for the composition.

As referred to herein, the terms "treatment" or "treating" refers to the full or partial removal of the symptoms and signs of the condition. For example, in the treatment of a fungal infection or colonisation, the treatment completely or partially removes the signs of the infection. Preferably in the treatment of infection, the treatment reduces or eliminates the infecting fungal pathogen leading to microbial cure.

As referred to herein, the term "fungal" refers to members of a large domain of organisms in the fungi class. Many fungal species and diseases which are targets for this invention as discussed below.

Fungal Species and Diseases

Fungal Diseases of Humans

Candidosis

There are more than 150 species of *Candida*, but only a small number are regarded as frequent pathogens for humans. The pathogens include *C. albicans, C. guilliermondii, C. krusei, C. parapsilosis, C. tropicalis, C. pseudotropicalis, C. lusitaniae, C. dubliniensis*, and *C. glabrata* (formerly classified as *Torulopsis glabrata*) to which can be added *Candida inconspicua, C. orthopsilosis* and *C. metapsilosis, Candida africana* within the *C. albicans* complex, *C. nivariensis* and *C. bracarensis* within the *C. glabrata* complex, *C. metapsilosis* and *C. orthopsilosis* within the *C. parapsilosis* complex, and *C. duobushaemulonii* and *C. haemulonii* var. *vulnera* in the *C. haemulonii* complex. Of extreme and recent importance is the emergence of the species of *Candida auris* as a multi-drug resistant pathogen.

Aspergillosis

Invasive aspergillosis is a major cause of morbidity and mortality in the immunosuppressed human and animal population and infection is caused by a number of species within the genus *Aspergillus* that are responsible for a diversity of invasive and semiinvasive conditions. The most common species causing invasive infection is *Aspergillus fumigatus*, with other important potentially pathogenic species implicated including *A. flavus; Aspergillus terreus*; and *Aspergillus niger*. Less frequently reported pathogenic species include *A. alabamensis, A. alliaceus* (teleomorph *Petromyces alliaceus*), *A. avenaceus, A. caesiellus, A. candidus, A. carneus, A. clavatus, A. calidoustus, A. flavipes, A. glaucus, A. granulosus, A. insuetus, A. keveii, A. lentulus, A. nidulans* (*Emericella nidulans*), *A. novofumigatus, A. ochraceus, A. puniceus, A. pseudodeflectus, A. quadrilineatus, A. restrictus, A. sydowii, A. tamarii, A. tanneri, A. thermomutatus* (teleomorph *Neosartorya pseudofischeri*), *A. tubingensis, A. udagawae* (*Neosartorya udagawae*), *A. versicolor, A. viridinutans, A. vitus* (teleomorph *Eurotium amstelodami*), and *A. wentii*.

Mucormycosis

Mucormycosis is an aggressive, angioinvasive fungal infection that afflicts immunocompromised patients with severe co-morbidities, such as uncontrolled diabetes mellitus. Skin and soft tissue infections in immunocompetent patient hosts may be encountered following severe soft tissue trauma. Agents of mucormycosis are ubiquitous fungi in the environment that are commonly found in decaying organic substrates, including bread, fruits, vegetable matter, soil, compost piles, and animal excreta. The most common agents of mucormycosis include *Rhizopus rhizopodoformis; Rhizopus arrhizus* (*Rhizopus oryzae*); *Rhizopus microsporus; Rhizomucor pusillus; Rhizopus stolonifer; Cunninghamella bertholletiae; Apophysomyces elegans; Saksenaea vasiformis; Lichtheimia* (*Absidia*) *corymbifera; Mucor circinelloides; Mucor velutinosus; Syncephalastrum racemosum*; and *Actinomucor*.

Entomophthoramycosis

Entomophthoramycosis typically presents as an indolent subcutaneous infection localized to the sinuses, head and face (conidiobolomycosis), or trunk and arms (basidiobolomycosis) and is usually acquired by inhalation or follows minor trauma, though gastrointestinal basidiobolomycosis has been reported in Arizona and the Near East and is likely acquired by ingestion. The most common agents isolated from cases of entomophthoramycosis include *Conidiobolus coronatus; Conidiobolus incongruous*; and *Basidiobolus ranarum*

Sporotrichosis

*Sporothrix schenckii* sensu lato comprises a group of closely related species of dimorphic fungi (including *S. luriei, S. brasiliensis, S. mexicana, S. pallida*, and *S. globosa*) that cause sporotrichosis. Acquisition of infection is associated with exposure to soil, plants, plant products (hay, straw, sphagnum moss), and a variety of animals (especially cats) in addition to humans can be affected.

Chromoblastomycosis

Chromoblastomycosis (chromomycosis) is a chronic, localized fungal infection of the skin and subcutaneous tissue that produces raised scaly lesions, usually of the lower extremities. Infection is caused by one of several dark-walled (dematiaceous) fungi found in the soil and in association with cacti, thorny plants, and other live or decaying vegetation. The most commonly isolated fungal species is *Fonsecaea pedrosoi* with other *Fonsecaea* species (*F. monophora* and *F. nubica*) and *Cladophialophora carrionii* also common aetiologic agents. *Phialophora verrucosa* and *Rhinocladiella aquaspersa* are less commonly reported.

Mycetoma

Mycetoma is a chronic progressive granulomatous infection of the skin and subcutaneous tissue most often affecting the lower extremities, typically a single foot. The agents of mycetoma are fungi and aerobic filamentous bacteria that have been found on plants and in the soil. Eumycotic or true fungal disease is caused by a variety of fungal organisms that can be divided into those that form dark grains (*Madurella* spp., *Biatriospora* spp., *Trematosphaeria* spp., *Pseudochaetosphaeroma* spp., *Roussoella* spp., *Rhytidhysteron* spp., *Curvularia* spp., *Exophiala* spp., *Falciformispora* spp., *Medicopsis* spp., *Phaeoacremonium* spp., *Phialophora verrucosa*) and those that form pale or white grains (*Scedosporium apiospermum* complex, *Aspergillus* spp., *Diaporthe phaseolorum, Fusarium* spp., *Neotestudina rosatii, Pleurostomophora ochracea*).

Cryptococcosis

The clinical presentation of cryptococcosis can vary from asymptomatic colonization of the respiratory airways to dissemination of infection into any part of the human body. *Cryptococcus* enters the host primarily through the lungs but has a special predilection for invading the central nervous system (CNS) of the susceptible host. Pulmonary infections are common and may have multiple clinical presentations while cryptococcal meningitis represents the primary life-threatening infection for this fungal pathogen. There are 19 cryptococcal species with two major pathogenic species, *Cryptococcus neoformans* and *Cryptococcus gattii*. The taxonomy of this genus continues to evolve—*C. neoformans* var. *grubii* (serotype A) currently having five genotypes (VNI, VNII, VNBI, VNBII, and the hybrid VNIII); *C. neoformans* var. neoformans a single serotype (serotype D or genotype VNIV); with five other cryptic species described (*Cryptococcus gattii, Cryptococcus bacillisporus, Cryptococcus deuterogattii, Cryptococcus tetragattii*, and *Cryptococcus decagattii* (serotypes B/C or VGI-VGV)).

Histoplasmosis

Histoplasmosis, caused by infection with *Histoplasma capsulatum*, is the most frequent cause of fungal respiratory infection and has a broad spectrum of clinical manifestations ranging from a self-limited, acute, influenza-like illness to a progressive disseminated infection that is life-threatening. The fungus is typically found in the midwestern and south eastern United States and in Central and South America with the fungus found in decaying bird guano (starlings and blackbirds) and bat guano. Patients with acquired immunodeficiency syndrome (AIDS) or who are receiving immunosuppressive drugs are predisposed to disseminated infection.

Blastomycosis

Blastomycosis is caused by *Blastomyces* species which include *B. dermatitidis, B. gilchristii, B. percursus, B. helicus, B. parvus*, and *B. silverae*. Infection is primarily acquired through the inhalation of infectious conidia and hyphal fragments following the disruption of soil. Once inside the lungs, the infectious particles convert into pathogenic yeast, which causes pneumonia and can disseminate to other organs.

Coccidioidomycosis

Coccidioidomycosis, also known as San Joaquin Valley fever or Valley fever, results from infection with *Coccidioides immitis* and *Coccidioides posadasii* that cause a systemic fungal infection commonly presenting as community-acquired pneumonia that lasts weeks to months whether treated with antifungal agents or not. Progressive pneumonia or haematogenous dissemination to other organs is a serious complication that requires treatment. Patients with diabetes are more likely to suffer pulmonary complications and the risk of dissemination is much more frequent in patients with impaired cellular immunity.

Dermatophytosis (Ringworm) and Other Superficial Mycoses

The superficial fungal infections include some of the most common infectious conditions, such as ringworm, tinea corporis, and pityriasis versicolor, and rare disorders such as tinea nigra. The four main genera of dermatophyte fungi pathogenic in humans and animals include *Trichophyton, Microsporum, Nannizzia*, and *Epidermophyton*. Other common fungi causing superficial mycosis include the yeasts such as *Candida* or *Malassezia* spp.

Paracoccidioidomycosis

Paracoccidioidomycosis is a Latin American endemic and systemic fungal disease characterized by two main clinical forms, either an acute/subacute serious disease observed in children, adolescents, and immunocompromised individuals, or a chronic disease characterised by pulmonary infiltrates seen in adults 30 years of age or older. Paracoccidioidomycosis is caused by species in the genus *Paracoccidioides*, encompassing five distinct phylogenetic species that include *P. brasiliensis, P. americana, P. restrepiensis*, and *P. venezueliensis* (formerly designated as S1, PS2, PS3, and PS4, respectively). To this list can be added *P. lutzii*, a new species recently described.

Uncommon Fungi and Related Species

*Scedosporium apiospermum* (*Pseudallescheria boydii*) Species Complex

*Scedosporium apiospermum, Scedosporium boydii* (formerly *Pseudallescheria boydii*), and *Scedosporium aurantiacum* are the most common species infecting humans.

*Lomentospora* (*Scedosporium*) *prolificans*

Disseminated infection and bone and joint infections caused by *Lomentospora* (formerly *Scedosporium*) *prolificans* which can also cause localised onychomycosis and infections of the eye and wounds.

Dark-Walled Fungi (*Bipolaris, Exophiala, Exserohilum, Phialophora, Ochroconis, Curvularia*, Others)

Infection is often termed "phaeohyphomycosis" and typically presents as localized skin and soft tissue infections, infections of the central nervous system, or allergic sinusitis associated with infection with *Alternaria, Bipolaris, Cladophialophora, Curvularia, Exophiala, Exserohilum, Ochroconis*, and *Wangiella.*

*Fusarium* spp.

Causes disseminated infection in immunocompromised patients as well as being a common cause of keratitis and other eye infections in contact lens wearers and following trauma. The most common species infecting humans include *Fusarium solani, Fusarium oxysporum*, or *Fusarium fujikuroi.*

*Trichosporon* spp.

Typically an infection of the immunocompromised and may be associated with central venous catheter caused by *Trichosporon asahii.*

*Malassezia furfur*

*Malassezia furfur* is a cause of catheter-related bloodstream infection and pityriasis versicolor.

Other Uncommon Yeasts

Other less common yeasts such as *Magnusiomyces capitatus* (formerly called *Saprochaete capitata* and *Blastoschizomyces capitatus*), *Pichia anomala, Rhodotorula* spp., and *Saccharomyces cerevisiae* may also cause catheter-related bloodstream infection.

*Talaromyces* (*penicillium*) *marneffei*

*Talaromyces* (*penicillium*) *marneffei* is a cause of acute disseminated infection of persons infected with human immunodeficiency virus in Southeast Asia.

*Lacazia loboi*

*Lacazia loboi* is a cause of chronic nodular or keloidal skin infection, commonly of the ears or face.

Agents of adiaspiromycosis (*Emmonsia* spp.)

Adiaspiromycosis is principally a pulmonary disease that ranges from asymptomatic to rapidly progressing respiratory failure and occasionally death and is associated with infection with *Emmonsia* spp., usually *Emmonsia crescens.*

*Emergomyces africanus*

*Emergomyces africanus* is a cause of disseminated infection most commonly afflicting severely immunocompromised persons.

*Prototheca* spp.

Disease is typically due to *Prototheca wickerhamii* or *Prototheca zopfii* presenting as localized skin or subcutaneous infection caused.

*Pythium* spp.

*Pythium* species can cause vascular infections in persons with iron overload, such as thalassemia, or ocular infections following trauma. Skin and subcutaneous infection and disseminated infection possible.

*Rhinosporidium seeberi*

*Rhinosporidium seeberi* infection can cause localized polypoidal lesions, chiefly of the nose, upper airway, and conjunctiva.

Pneumocystosis

Pneumocystosis or *Pneumocystis* pneumonia (PCP) remains a leading cause of opportunistic infection, morbidity, and mortality estimated to affect more than 400,000 persons with more than 52,000 deaths worldwide each year. The most common causative agent is *Pneumocystis jirovecii*, with two other species less commonly involved, *Pneumocystis carinii* and *P. murina.*

Fungal Diseases of Animals

Cutaneous Fungal Infections: Dermatophytosis

The dermatophytoses of veterinary importance consist of fungi of the genera *Microsporum, Trichophyton*, and *Epidermophyton.* These organisms cause superficial cutaneous infections of the stratum corneum, hair shaft, and/or claw. Although there are approximately 30 species of dermatophytes, relatively few infect animals, the most common being *Microsporum canis, Microsporum persicolor, Trichophyton* spp., *Trichophyton erinacei*, or the geophilic species *Microsporum gypseum.*

Cutaneous Fungal Infections: *Malassezia* Dermatitis

*Malassezia* spp. (previously *Pityrosporum* spp.) are lipophilic yeasts that are most often isolated from the skin and mucosal sites of clinically healthy mammals and birds. The genus is divided into two groups based on their lipid dependency in culture media. *Malassezia pachydermatis* is unique within the genus in that it can be cultivated on routine mycologic media without lipid supplementation. Lipid-dependent *Malassezia* species include *Malassezia furfur, Malassezia sympodialis, Malassezia globosa, Malassezia obtusa, Malassezia restricta, Malassezia slooffiae, Malassezia dermatis, Malassezia japonica, Malassezia yamatoensis, Malassezia nana, Malassezia caprae*, and *Malassezia equina.*

Blastomycosis

Blastomycosis is a systemic mycotic infection caused by the dimorphic fungus *Blastomyces dermatitidis.*

Histoplasmosis

The aetiologic agent of American histoplasmosis is the soilborne, dimorphic fungus *Histoplasma capsulatum.*

Cryptococcosis

As with humans, cryptococcosis is an important fungal infection of animals and the most common systemic mycosis of cats. The most commonly isolated causative agents are *Cryptococcus neoformans* and *Cryptococcus gattii.*

Coccidioidomycosis and Paracoccidioidomycosis

Coccidioidiomycosis is a disease caused by *Coccidioides immitis* (an organism distributed in the San Joaquin Valley of California) or *Coccidioides posadasii* (found in all other endemic areas). Paracoccidioidomycosis is a systemic fungal disease of people and, less commonly, of animals in Central and South America caused by the dimorphic fungus *Paracoccidioides brasiliensis*. The disease in animals is characterized by granulomatous pulmonary and disseminated lesions.

Sporotrichosis

Sporotrichosis is a mycotic disease caused by the thermal dimorphic fungus *Sporothrix schenckii*. In addition to humans, it has been reported in chimpanzees, cats, dogs, pigs, mice, rats, hamsters, mules, horses, donkeys, cattle, goats, fox, armadillos, dolphins, camels, and birds.

Aspergillosis and Penicilliosis

*Aspergillus* and *Penicillium* species are saprophytic fungi, ubiquitous in the environment, that generally cause either sino-nasal or pulmonary and disseminated infections in dogs and cats.

Candidiasis

*Candida albicans* is the most common *Candida* species isolated from animals. Cutaneous infections of dogs are associated with infection with *C. albicans, C. guilliermondii, C. parapsilosis* while *C. albicans* is the most common isolate in cats with skin infection. The *Candida* species most commonly isolated from urinary tract infections in dogs include *C. albicans, C. glabrata, C. krusei, C. parapsilosis, C. rugosa, C. tropicalis*; while in cats isolates are predominantly *C. albicans, C. glabrata, C. guilliermondii, C. krusei, C. parapsillosis, C. tropicalis*. Gastrointestinal overgrowth can be associated with *C. albicans* or *C. famata* in dogs, while in both dogs and cats, systemic disease is principally associated with *C. albicans.*

Rhodotorulosis

*Rhodotorula* spp. have been reported as causing either granulomatous epididymitis or fungal cystitis in dogs.

Trichosporonosis

Isolates from domestic animals have included *Trichosporon pullulans, Trichosporon asahii, Trichosporon domesticum, Trichosporon loubieri*, and unspecified *Trichosporon* spp. have caused infections in cats. *T. cutaneum* has been isolated from a dog with skin disease.

Miscellaneous Fungal Infections

Pythiosis: *Pythium insidiosum*

Lagenidiosis: *Lagenidium* spp.

Zygomycosis/Mucormycosis: *Mucor, Rhizopus, Rhizomucor, Absidia*

Entomophthoromycosis: *Conidiobolus, Basidiobolus.*

Adiaspiromycosis: *Emmonsia* c *parva*

Hyalohyphomycosis: *Acremonium, Chrysosporium, Colletotrichum, Fusarium, Geomyces, Geotrichum, Geosmithia, Paecilomyces, Pseudallescheria, Metarhizium, Monocillium indicum, Schizophyllum commune.*

Phaeohyphomycosis: *Alternaria, Bipolaris, Cladophialophora, Curvularia Exophiala, Fonsecaea, Macrophomina, Microsphaeropsis arundinis, Moniliella, Ochroconis, Phialemonium, Phialophora, Phoma, Pseudomicrodochium, Scolecobasidium, Stemphyllium, Ulocladium*

Eumycotic mycetoma (white grain): *Acremonium, Pseudallescheria*

Eumycotic mycetoma (black grain): *Cladophialophora bantiana, Curvularia, Madurella, Phaeococcomyces, Staphylotrichum coccosporum.*

Pneumocystosis

*Pneumocystis carinii* causes opportunistic pneumonia of animals.

Rhinosporidiosis

Rhinosporidiosis is a chronic granulomatous disease caused by *Rhinosporidium seeberi* that induces tumour-like growths of epithelial tissues in domestic animals, birds, and people.

Fungal Pathogens of Plants

Ascomycetes

*Colletotrichum* spp. (sexual stage: *Glomerella*); *Erysiphe graminis* (*Blumeria graminis*); *Gaeumannomyces graminis; Magnaporthe* spp. (incl *oryzae*); *Mycosphaerella* spp. (incl *fijiensis, graminicola*); *Podosphaera leucotricha; Pyrenophora teres; Pyricularia oryzae; Rhynchosporium secalis; Sclerotinia* spp.; *Sphaerotheca fuliginea; Thielaviopsis* spp.; *Uncinula necator; Venturia inaequalis; Verticillium* spp.

Basidiomycetes

*Armillaria* spp.; *Austropuccinia psidii* (formerly *Puccinia psidii*, initially identified as *Uredo rangelii*); *Melampsora* spp. (incl *lini*); *Phakopsora* spp, (incl *pachyrhizi*); *Puccinia* spp.; *Rhizoctonia* spp. (incl *solani*); *Tilletia* spp.; *Uromyces* spp.; *Ustilago* spp. (incl *maydis*).

Deuteromycetes

*Alternaria* spp. (incl *solani*); *Botrytis* spp. (incl *cinerea*); *Cercospora* spp.; *Fusarium* spp. (incl *graminearum, oxysporum*); *Helminthosporium* spp.; *Pseudocercosporella herpotrichoides; Septoria* spp (incl *nodorum, tritici*).

Oomycetes

*Phytophthora infestans; Plasmopara viticola; Pseudoperonospora cubensis; Pythium* spp.

Fungal Pathogens of Bees

Ascomycetes

*Ascosphaera apis* (cause of chalkbrood).

*Aspergillus* spp. (incl *A. fumigatus, A. flavus*, and *A. niger*, the cause stonebrood).

Fungal Pathogens of Fish

*Saprolegnia* species (the cause of Saprolegniasis, a fungal disease of fish and fish eggs, often first observed as fluffy tufts of cotton-like material, coloured white to shades of grey and brown, on the skin, fins, gills, or eyes of fish or on fish eggs)

*Branchiomyces sanguinis* (the cause of gill rot in carp)

*Branchiomyces demigrans* (the cause of gill rot in pike and tench)

*Icthyophonus hoferi* (the cause of *Icthyophonus* disease, also known as swinging disease).

Pathogenic Fungi of Bats

*Pseudogymnoascus destructans* (formerly known as *Geomyces destructans*), causes white-nose syndrome (WNS), a fatal disease that has devastated bat populations.

Pathogenic Fungi of Amphibians

*Batrachochytrium dendrobatidis* and *Batrachochytrium salamandrivorans* (nonhyphal zoosporic fungus species that are the cause of chytridiomycosis, an infectious disease in amphibians linked to dramatic population declines and extinctions of amphibian species).

In one example, the method is used in combination with a second (or third or more) antifungal or fungicide compound. Such examples of antifungal or fungicidal compounds are discussed below.

Antifungal or Fungicidal Agents to be Used in Combination

Antifungal Agents Used in Humans and Animals

In the two decades between 2000 and 2020 there were only 9 new antifungal drugs approved for use in humans in the US by the FDA, 3 (luliconozole in 2013, efinaconazole in 2014 and tavaborole in 2014) for topical treatment of onychomycosis or tinea, and 6 for systemic use, including 3 echinocandins (caspofungin in 2001, micafungin in 2005 and anidulafungin in 2006) and 3 azoles (voriconazole in 2002, Posaconazole in 2006 and isavuconazonium, the prodrug of isavuconazole, in 2015). Notably, only one new class of antifungal agent (the echinocandins) has been approved in the 21st Century.

There are 48 antifungal agents approved for use in humans and animals, belonging to 15 chemical and mode of action classes. Only four classes are routinely used for the treatment of systemic fungal diseases: polyenes, echinocandins, azoles and pyrimidines.

The compositions of the present invention may comprise, in addition to the compound, a second antifungal agent chosen from the list comprising:

- POLYENES: Amphotericin B Deoxycholate, Liposomal Amphotericin B, Amphotericin B Lipid Complex (ABLC), Nystatin, Natamycin;
- ECHINOCANDINS: Caspofungin, Micafungin, Anidulafungin;
- ALLYLAMINES AND BENZYLAMINE DERIVATIVES: Terbinafine, Butenafine, Naftifine,
- SYSTEMIC AZOLES: Ketoconazole, Fluconazole, Itraconazole, Miconazole, Voriconazole, Posaconazole, Isavuconazole (and its prodrug isavuconazonium), Albaconazole, Ravuconazole;
- TOPICAL AZOLES: Bifonazole, Butoconazole, Clotrimazole, Croconazole, Eberconazole, Econazole, Efinaconazole, Enilconazole, Fenticonazole, Flutrimazole, Isoconazole, Lanoconazole, Neticonazole, Oxiconazole, Sertaconazole, Sulconazole, Terconazole, Tioconazole;
- THIOCARBOMATES: Tolnaftate
- HYDROXYPYRIDONES: Ciclopirox, Rilopirox;
- MORPHOLINES: Amorolfine;
- PYRIMIDINE: Flucytosine (5-Fluorocytosine, 5-FC);
- TUBULIN INHIBITOR: Griseofulvin;
- HALOPHENOLS: Haloprogin;
- QUINOLINES: Iodoquinol, Clioquinol;
- ZINC PYRITHIONE;
- POTASSIUM IODIDE;
- BENZOXABOROLES: Tavaborole.

Fungicides Used in Agriculture

There are 440 distinct fungicides approved for agricultural, botanical or environmental use belonging to 74 chemical classes.

The compositions of the present invention may comprise, in addition to the compound, a second antifungal agent chosen from the list comprising:

- ALIPHATIC NITROGEN FUNGICIDES; butylamine; cymoxanil; dodicin; dodine; guazatine; iminoctadine;
- AMIDE FUNGICIDES (see also antibiotic, carbamate, conazole, imidazole, methoxyiminoacetamide strobilurin, pyridine, pyrazolecarboxamide, thiophene, thiazole, urea fungicides); carpropamid; chloraniformethan; cyflufenamid; diclocymet; dimoxystrobin (methoxyiminoacetamide strobilurin); fenoxanil; flumetover; mandipropamid; triforine; acylamino acid fungicides; benalaxyl (benalaxyl-M) (anilide); furalaxyl (furanilide); metalaxyl (metalaxyl-M) (anilide); valifenalate; anilide fungicides; fenhexamid; metsulfovax; ofurace; pyracarbolid; pyraziflumid; tiadinil; vangard; benzanilide fungicides; benodanil; flutolanil; mebenil; mepronil; salicylanilide; tecloftalam; furanilide fungicides; fenfuram; furcarbanil; methfuroxam; sulfonanilide fungicides; flusulfamide; benzamide fungicides; benzohydroxamic acid; fluopimomide; tioxymid; trichlamide; zarilamid; zoxamide; furamide fungicides; cyclafuramid; furmecyclox; phenylsulfamide fungicides; dichlofluanid; tolylfluanid; picolinamide fungicides; florylpicoxamid;
- ANTIBIOTIC FUNGICIDES; aureofungin; blasticidin-S; cycloheximide; fenpicoxamid (picolinamide); griseofulvin; kasugamycin; moroxydine; natamycin; ningnanmycin; polyoxins; polyoxorim; streptomycin; validamycin; strobilurin fungicides; fluoxastrobin; mandestrobin (amide); pyribencarb (carbamate, pyridine); methoxyacrylate strobilurin fungicides; azoxystrobin; bifujunzhi; coumoxystrobin; enoxastrobin; flufenoxystrobin; jiaxiangjunzhi; picoxystrobin; pyraoxystrobin (phenylpyrazole); methoxycarbanilate strobilurin fungicides; pyraclostrobin (carbanilate, phenylpyrazole); pyrametostrobin (carbanilate, phenylpyrazole); triclopyricarb (carbanilate, pyridine); methoxyiminoacetamide strobilurin fungicides (see also amides); fenaminstrobin (amide); metominostrobin (amide); orysastrobin (amide); methoxyiminoacetate strobilurin fungicides; kresoxim-methyl; trifloxystrobin;
- AROMATIC FUNGICIDES; biphenyl; chlorodinitronaphthalenes; chloroneb; chlorothalonil; cresol; dicloran; fenjuntong; hexachlorobenzene; pentachlorophenol; quintozene; sodium pentachlorophenate; tecnazene (TCNB); thiocyanatodinitrobenzenes; trichlorotrinitrobenzenes;
- ARSENICAL FUNGICIDES; Asomate (dithiocarbamate); Urbacide (dithiocarbamate);
- ARYL PHENYL KETONE FUNGICIDES; metrafenone; pyriofenone;
- BENZIMIDAZOLE FUNGICIDES; Albendazole (benzimidazolylcarbamate); benomyl (benzimidazolylcarbamate); carbendazim (benzimidazolylcarbamate); chlorfenazole; cypendazole (benzimidazolylcarbamate); debacarb (benzimidazolylcarbamate); fuberidazole; mecarbinzid (benzimidazolylcarbamate); rabenzazole (pyrazole); thiabendazole (thiazole);
- BENZIMIDAZOLE PRECURSOR FUNGICIDES; Furophanate (carbamate); Thiophanate (carbamate); thiophanate-methyl (carbamate);

BENZOTHIAZOLE FUNGICIDES; benthiazole; chlobenthiazone; dichlobentiazox; probenazole;

BOTANICAL FUNGICIDES; allicin; berberine (quaternary ammonium); carvacrol; carvone; osthol; sanguinarine (quaternary ammonium); santonin;

BRIDGED DIPHENYL FUNGICIDES (see also pyridine fungicides); bithionol; dichlorophen; diphenylamine; hexachlorophene;

CARBAMATE FUNGICIDES (see also antibiotic, benzimidazole, benzimidazole precursor, pyridine fungicides); Benthiavalicarb (valinamide, benzothiazole); iodocarb; iprovalicarb(valinamide); propamocarb; tolprocarb; carbanilate fungicides; diethofencarb;

CONAZOLE FUNGICIDES; conazole fungicides (imidazoles); climbazole; clotrimazole; imazalil; oxpoconazole; prochloraz; triflumizole; conazole fungicides (triazoles); azaconazole; bromuconazole; cyproconazole; diclobutrazol; difenoconazole; diniconazole (diniconazole-M); epoxiconazole; etaconazole; fenbuconazole; fluquinconazole; flusilazole; flutriafol; furconazole (furconazole-cis); hexaconazole; huanjunzuo; imibenconazole; ipconazole; ipfentrifluconazole; mefentrifluconazole; metconazole; myclobutanil; penconazole; propiconazole; prothioconazole; quinconazole; simeconazole; tebuconazole; tetraconazole; triadimefon; triadimenol; triticonazole; uniconazole (uniconazole-P);

COPPER FUNGICIDES (see also dithiocarbamate fungicides); acypetacs-copper; basic copper carbonate; basic copper sulfate; Bordeaux mixture; Burgundy mixture; Cheshunt mixture; copper acetate; copper hydroxide; copper naphthenate; copper oleate; copper oxychloride; copper silicate; copper sulfate; copper zinc chromate; cuprobam; cuprous oxide; mancopper (polymeric dithiocarbamate); oxine-copper; saisentong (thiadiazole); thiodiazole-copper (thiadiazole);

CYANOACRYLATE FUNGICIDES; benzamacril; phenamacril;

DICARBOXIMIDE FUNGICIDES (see also imidazole, oxazole fungicides); famoxadone (oxazole); fluoroimide (pyrrole); dichlorophenyl dicarboximide fungicides; procymidone; phthalimide fungicides (see also organophosphorus fungicides); captafol; captan; folpet; thiochlorfenphim;

DINITROPHENOL FUNGICIDES; binapacryl; dinobuton; dinocap (dinocap-4, dinocap-6, meptyldinocap); dinocton; dinopenton; dinosulfon; dinoterbon; DNOC (4,6-dinitro-o-cresol);

DITHIOCARBAMATE FUNGICIDES (see also arsenical, morpholine, zinc fungicides); amobam; azithiram; cufraneb (copper); cuprobam (copper); disulfiram; ferbam; metam; nabam; tecoram; thiram; cyclic dithiocarbamate fungicides; dazomet; etem; milneb; polymeric dithiocarbamate fungicides (see also copper, zinc fungicides); maneb; polycarbamate (zinc);

DITHIOLANE FUNGICIDES; isoprothiolane; saijunmao (fumigant);

FUMIGANT FUNGICIDES (see also DITHIOLANE FUNGICIDES); carbon disulfide; cyanogen; dimethyl disulfide; methyl bromide; methyl iodide; sodium tetrathiocarbonate; hydrazide fungicides; benquinox;

IMIDAZOLE FUNGICIDES (see also conazoles, triazoles); Cyazofamid (sulfonamide fungicide); fenamidone; fenapanil; glyodin; iprodione (dichlorophenyl dicarboximide); isovaledione (dichlorophenyl dicarboximide); pefurazoate (amide); triazoxide;

INORGANIC FUNGICIDES (see also copper fungicides, inorganic mercury fungicides), potassium azide; potassium thiocyanate; sodium azide; sulfur;

MERCURY FUNGICIDES; inorganic mercury fungicides; mercuric chloride; mercuric oxide; mercurous chloride; organomercury fungicides; (3-ethoxypropyl) mercury bromide; ethylmercury acetate; ethylmercury bromide; ethylmercury chloride; ethylmercury 2,3-dihydroxypropyl mercaptide; ethylmercury phosphate; N-(ethylmercury)-p-toluenesulfonanilide; hydrargaphen; 2-methoxyethylmercury chloride; methylmercury benzoate; methylmercury dicyandiamide; methylmercury pentachlorophenoxide; 8-phenylmercurioxyquinoline; phenylmercuriurea; phenylmercury acetate; phenylmercury chloride; phenylmercury derivative of pyrocatechol; phenylmercury nitrate; phenylmercury salicylate; thiomersal; tolylmercury acetate;

MORPHOLINE FUNGICIDES; aldimorph; benzamorf; carbamorph (dithiocarbamate); dimethomorph; dodemorph; fenpropimorph; flumorph; pyrimorph; tridemorph;

ORGANOPHOSPHORUS FUNGICIDES; ampropylfos; ditalimfos (phthalimide); EBP (S-benzyl O,O-diethyl phosphorothioate); edifenphos; fosetyl (including esters and salts); hexylthiofos; inezin; iprobenfos (IBP); izopamfos; kejunlin; phosdiphen; pyrazophos; tolclofos-methyl; triamiphos;

ORGANOTIN FUNGICIDES; decafentin; fentin (acetate, chloride, hydroxide); tributyltin oxide;

OXATHIIN FUNGICIDES; Carboxin (anilide); Oxycarboxin (anilide);

OXAZOLE FUNGICIDES (see also anilide, DICARBOXIMIDE, pyrazole, thiazole FUNGICIDES); Chlozolinate (dichlorophenyl dicarboximide); dichlozoline (dichlorophenyl dicarboximide); drazoxolon; fluoxapiprolin (thiazole, pyrazole); hymexazol (hymexazole, hydroxyisoxazole); metazoxolon; myclozolin (dichlorophenyl dicarboximide); oxadixyl (anilide); oxathiapiprolin (pyrazole); pyrisoxazole (pyridine); vinclozolin (dichlorophenyl dicarboximide);

POLYSULFIDE FUNGICIDES; barium polysulfide; calcium polysulfide; potassium polysulfide; sodium polysulfide;

PYRAZOLE FUNGICIDES (see also benzimidazole, OXAZOLE, tetrazole fungicides); phenylpyrazole fungicides; fenpyrazamine; pyrazolecarboxamide fungicides; benzovindiflupyr; bixafen (anilide); flubeneteram (anilide); fluindapyr; fluxapyroxad (anilide); furametpyr; inpyrfluxam; isoflucypram; isopyrazam; penflufen (anilide); penthiopyrad; pydiflumetofen; pyrapropoyne; sedaxane (anilide); tolfenpyrad;

PYRIDAZINE FUNGICIDES; pyridachlometyl;

PYRIDINE FUNGICIDES (see also antibiotic, oxazole fungicides); aminopyrifen; boscalid (anilide); buthiobate; dipyrithione; fluazinam; fluopicolide (benzamide); fluopyram (benzamide); parinol (bridged diphenyl); pyridinitril; pyrifenox; pyroxychlor; pyroxyfur;

PYRIMIDINE FUNGICIDES; bupirimate; diflumetorim; dimethirimol; ethirimol; fenarimol; ferimzone; nuarimol; triarimol; anilinopyrimidine fungicides; cyprodinil; mepanipyrim; pyrimethanil;

PYRROLE FUNGICIDES (see also DICARBOXIMIDE fungicides); dimetachlone; fenpiclonil; fludioxonil;

QUINOLINE FUNGICIDES; ethoxyquin; halacrinate; 8-hydroxyquinoline sulfate; ipflufenoquin; quinacetol; quinofumelin; quinoxyfen; tebufloquin;

QUINONE FUNGICIDES; chloranil; dichlone; dithianon;

QUINOXALINE FUNGICIDES; Chinomethionat (quinomethionate, oxythioquinox); chlorquinox; thioquinox;

TETRAZOLE FUNGICIDES (see also carbamate, phenylpyrazole, pyridine fungicides); metyltetraprole (phenylpyrazole); picarbutrazox (carbamate, pyridine);

THIADIAZOLE FUNGICIDES (see also copper, zinc fungicides); etridiazole;

THIAZOLE FUNGICIDES (see also, benzimidazole, BENZOTHIAZOLE, OXAZOLE, pyrazole FUNGICIDES); Ethaboxam (thiophene); Isotianil (anilide); metsulfovax; octhilinone; thifluzamide (anilide);

THIAZOLIDINE FUNGICIDES; flutianil; thiadifluor;

THIOCARBAMATE FUNGICIDES; methasulfocarb; prothiocarb;

THIOPHENE FUNGICIDES (see also amide, THIAZOLE FUNGICIDES); Isofetamid (amide); Silthiofam (amide); TRIAZINE FUNGICIDES; anilazine;

TRIAZOLE FUNGICIDES (see also conazole fungicides); Amisulbrom (sulfonamide fungicide); bitertanol; fluotrimazole; triazbutil;

TRIAZOLOPYRIMIDINE FUNGICIDES; ametoctradin;

UREA FUNGICIDES; Bentaluron (benzothiazole); pencycuron; quinazamid (amide);

ZINC FUNGICIDES (see also copper and dithiocarbamate, polymeric dithiocarbamate fungicides); acypetacs-zinc; mancozeb (polymeric dithiocarbamate); metiram (polymeric dithiocarbamate); polyoxorim-zinc; propineb (polymeric dithiocarbamate); zinc naphthenate; zinc thiazole (thiadiazole); zinc trichlorophenate; zineb (polymeric dithiocarbamate); ziram (dithiocarbamate);

OTHER FUNGICIDES; acibenzolar (benzo-thiadiazole—BTH); acibenzolar-S-methyl (benzo-thiadiazole—BTH); acypetacs; allyl alcohol; benzalkonium chloride; bethoxazin; bromothalonil; chitosan; chloropicrin; DBCP ((RS)-1,2-dibromo-3-chloropropane); dehydroacetic acid; diclomezine; diethyl pyrocarbonate; dipymetitrone; ethylicin; fenaminosulf; fenitropan; fenpropidin; formaldehyde; furfural; hexachlorobutadiene; laminarin (polysaccharide); methyl isothiocyanate; naftifine (allylamine); nitrostyrene; nitrothal-isopropyl; OCH (perchlorocyclohex-2-en-1-one); pentachlorophenyl laurate; 2-phenylphenol; Phthalide (fthalide); piperalin; propamidine; proquinazid; pyroquilon; sodium o-phenylphenoxide; spiroxamine; sultropen; terbinafine (allylamine); thicyofen; tricyclazole.

Fungicide Combination Products

For agricultural fungicides combination treatment is well established. To delay the onset of antifungal resistance, to expand the breadth of the antifungal spectrum or to decrease the dose or increase effectiveness combinations of one or more antifungal agents can be prepared.

The compositions of the present invention may comprise, in addition to the compound, a combination of fungicides in commercially available products chosen from the list comprising:

amisulbrom+copper (Cu) present as tribasic copper sulphate; azoxystrobin+cyproconazole; azoxystrobin+difenoconazole; azoxystrobin+flutriafol; azoxystrobin+oxathiapiprolin; azoxystrobin+propiconazole; benzovindiflupyr+propiconazole; bixafen+prothioconazole; boscalid+kresoxim-methyl; boscalid+pyraclostrobin; captan+metalaxyl; chlorothalonil+carbendazim; chlorothalonil+fludioxonil+propiconazole; chlorothalonil+iprodione+thiophanate-methyl+tebuconazole; copper present as copper oxychloride+metalaxyl; copper present as copper oxychloride+sulphur; cyproconazole+propiconazole; dimethomorph+ametoctradin; dimethomorph+azoxystrobin; epoxiconazole+azoxystrobin; epoxiconazole+azoxystrobin+tebuconazole; epoxiconazole+pyraclostrobin; epoxiconazole+pyraclostrobin+fluxapyroxad; fluazinam+azoxystrobin; fludioxonil+azoxystrobin; fludioxonil+cyprodinil; fludioxonil+metalaxyl-m+azoxystrobin; fludioxonil+metalaxyl-m+azoxystrobin+sedaxane; fludioxonil+propiconazole; fludioxonil+sedaxane; fluopyram+tebuconazole; fluopyram+trifloxystrobin; imazalil present as imazalil sulphate+pyrimethanil; imidacloprid+tebuconazole; imidacloprid+triadimenol; iprodione+trifloxystrobin; mancozeb+azoxystrobin; mancozeb+copper (cu) present as cupric hydroxide; mancozeb+metalaxyl; mancozeb+sulfur (S) as wettable sulfur; mandipropamid+mancozeb; metalaxyl+ipconazole; metalaxyl+penflufen+prothioconazole; metalaxyl-M+azoxystrobin; metalaxyl-M+difenoconazole; metalaxyl-M+sedaxane+difenoconazole; metiram+pyraclostrobin; penflufen+trifloxystrobin; propamocarb hydrochloride+fluopicolide; propiconazole+tebuconazole; propineb+oxadixyl; prothioconazole+tebuconazole; pyraclostrobin+fluxapyroxad; pyraclostrobin+triticonazole; sulphur+tebuconazole; thiram+carboxin; thiram+thiabendazole; trifloxystrobin+tebuconazole; azoxystrobin+tebuconazole.

Agricultural fungicides can also include another agent that has activity against other pests of targets plants. For examples a fungicide can be prepared in combination with an insecticide as illustrated by the following examples:

tebuconazole (fungicide)+imidacloprid (insecticide); triadimenol (fungicide)+imidacloprid (insecticide); metalaxyl-M (fungicide)+sedaxane (fungicide)+difenoconazole (fungicide)+thiamethoxam (insecticide).

Pharmaceutically and veterinary acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically and veterinary acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The pharmaceutically or veterinary acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such acceptable salts are the iodide, acetate, phenyl acetate, trifluoroacetate, acrylate, ascorbate, benzoate, chlorobenzoate, dinitrobenzoate, hydroxybenzoate, methoxybεnzoate, methylbenzoate, o-acetoxybenzoate, naphthalene-2-benzoate, bromide, isobutyrate, phenylbutyrate, γ-hydroxybutyrate, β-hydroxybutyrate, butyne-I,4-dioate, hexyne-I,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, merhanesulfonate, naphthalene-l-sulfonate, naphthalene-2-sulfonate, p-toluenesulfonate, xylenesulfonate, tartarate, and the like.

The pharmaceutical or veterinary compositions of the invention may be formulated in conventional manner, together with other pharmaceutically acceptable excipients if desired, into forms suitable for oral, parenteral, or topical administration. The modes of administration may include parenteral, for example, intramuscular, subcutaneous and intravenous administration, oral administration, topical administration and direct administration to sites of infection such as intraocular, intraaural, intrauterine, intranasal, intramammary, intraperitoneal and intralesional.

The pharmaceutical or veterinary compositions of the invention may be formulated for oral administration. Traditional inactive ingredients may be added to provide desirable colour, taste, stability, buffering capacity, dispersion, or other known desirable features. Examples include red iron oxide, silica gel, sodium laurel sulphate, titanium dioxide, edible white ink, and the like. Conventional diluents may be used to make compressed tablets. Both tablets and capsules may be manufactured as sustained-release compositions for the continual release of medication over a period of time. Compressed tablets may be in the form of sugar coated or film coated tablets, or enteric-coated tablets for selective disintegration in the gastrointestinal tract. Liquid dosage forms for oral administration may contain colouring and/or flavouring to increase patient compliance. As an example, the oral formulation comprising the compound may be a tablet comprising anyone, or a combination of, the following excipients: calcium hydrogen phosphate dehydrate, microcrystalline cellulose, lactose, hydroxypropyl methyl cellulose, and talc.

The compositions described herein may be in the form of a liquid formulation. Examples of preferred liquid compositions include solutions, emulsions, injection solutions, solutions contained in capsules. The liquid formulation may comprise a solution that includes a therapeutic agent dissolved in a solvent. Generally, any solvent that has the desired effect may be used in which the therapeutic agent dissolves and which can be administered to a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

The composition described herein may be in the form of a liquid suspension. The liquid suspensions may be prepared according to standard procedures known in the art. Examples of liquid suspensions include micro-emulsions, the formation of complexing compounds, and stabilising suspensions. The liquid suspension may be in undiluted or concentrated form. Liquid suspensions for oral use may contain suitable preservatives, antioxidants, and other excipients known in the art functioning as one or more of dispersion agents, suspending agents, thickening agents, emulsifying agents, wetting agents, solubilising agents, stabilising agents, flavouring and sweetening agents, colouring agents, and the like. The liquid suspension may contain glycerol and water.

The composition described herein may be in the form of an oral paste. The oral paste may be prepared according to standard procedures known in the art.

The composition is described herein may be in the form of a liquid formulation for injection, such as intra-muscular injection, and prepared using methods known in the art. For example, the liquid formulation may contain polyvinylpyrrolidone K30 and water.

The composition is described herein may be in the form of topical preparations. The topical preparation may be in the form of a lotion or a cream, prepared using methods known in the art. For example, a lotion may be formulated with an aqueous or oily base and may include one or more excipients known in the art, functioning as viscosity enhancers, emulsifying agents, fragrances or perfumes, preservative agents, chelating agents, pH modifiers, antioxidants, and the like. For example, the topical formulation comprising the compound may be a gel comprising anyone, or a combination of, the following excipients: PEG 4000, PEG 200, glycerol, propylene glycol. The compounds of the invention may further be formulated into a solid dispersion using SoluPlus (BASF, www.soluplys.com) and formulated with anyone, or a combination of, the following excipients: PEG 4000, PEG 200, glycerol, propylene glycol.

For aerosol administration, the composition is of the invention they be provided in finely divided form together with a non-toxic surfactant and a propellant. The surfactant is preferably soluble in the propellant. Such surfactants may include esters or partial esters of fatty acids.

The compositions of the invention may alternatively be formulated using nanotechnology drug delivery techniques such as those known in the art. Nanotechnology-based drug delivery systems have the advantage of improving bioavailability, patient compliance and reducing side effects.

The formulation of the composition of the invention includes the preparation of nanoparticles in the form of nanosuspensions or nanoemulsions, based on compound solubility. Nanosuspensions are dispersions of nanosized drug particles prepared by bottom-up or top-down technology and stabilised with suitable excipients. This approach may be applied to robenidene which has poor aqueous and lipid solubility in order to enhance saturation solubility and improve dissolution characteristics. An example of this technique is set out in Sharma and Garg (2010) (Pure drug and polymer-based nanotechnologies for the improved solubility, stability, bioavailability, and targeting of anti-HIV drugs. *Advanced Drug Delivery Reviews,* 62: p. 491-502). Saturation solubility will be understood to be a compound-specific constant that depends on temperature, properties of the dissolution medium, and particle size (<1-2 μm).

The composition of the invention may be provided in the form of a nanosuspension. For nanosuspensions, the increase in the surface area may lead to an increase in saturation solubility. Nanosuspensions are colloidal drug delivery systems, consisting of particles below 1 μm. Compositions of the invention may be in the form of nanosuspensions including nanocrystalline suspensions, solid lipid nanoparticles (SLNs), polymeric nanoparticles, nanocapsules, polymeric micelles and dendrimers. Nanosuspensions may be prepared using a top-down approach where larger particles may be reduced to nanometre dimensions by a variety of techniques known in the art including wet-milling and high-pressure homogenisation. Alternatively, nanosuspensions may be prepared using a bottom-up technique where controlled precipitation of particles may be carried out from solution.

The composition of the invention may be provided in the form of a nanoemulsion. Nanoemulsions are typically clear oil-in-water or water-in-oil biphasic systems, with a droplet size in the range of 100-500 nm, and with compounds of interest present in the hydrophobic phase. The preparation of nanoemulsions may improve the solubility of compounds described herein, leading to better bioavailability. Nanosized suspensions may include agents for electrostatic or steric stabilisation such as polymers and surfactants. Compositions in the form of SLNs may comprise biodegradable lipids such as triglycerides, steroids, waxes and emulsifiers such as soybean lecithin, egg lecithin, and poloxamers. The preparation of a SLN preparation may involve dissolving/dispersing drug in melted lipid followed by hot or cold homogenisation. If hot homogenisation is used, the melted lipidic phase may be dispersed in an aqueous phase and an emulsion prepared. This may be solidified by cooling to achieve SLNs. If cold homogenisation is used, the lipidic phase may be solidified in liquid nitrogen and ground to micron size. The resulting powder may be subjected to high-pressure homogenisation in an aqueous surfactant solution.

The compound as described herein may be dissolved in oils/liquid lipids and stabilised into an emulsion formulation. Nanoemulsions may be prepared using high- and low-energy droplet reduction techniques. High-energy methods may include high-pressure homogenisation, ultrasonication and microfluidisation. If the low-energy method is used, solvent diffusion and phase inversion will generate a spontaneous nanoemulsion. Lipids used in nanoemulsions may be selected from the group comprising triglycerides, soybean oil, safflower oil, and sesame oil. Other components such as emulsifiers, antioxidants, pH modifiers and preservatives may also be added.

The composition may be in the form of a controlled-release formulation may include a degradable or non-degradable polymer, hydrogel, organogel, or other physical construct that modifies the release of the polyether ionophore. It is understood that such formulations may include additional inactive ingredients that are added to provide desirable colour, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol.

The formulations of the invention may have the advantage of increased solubility and/or stability of the compound, particularly for those formulations prepared using nanotechnology techniques. Such increased stability and/or stability of the compound may improve bioavailability and enhance drug exposure for oral and/or parenteral dosage forms.

Throughout this specification, unless the context requires otherwise, the word "comprise" or variations such as "comprises" or "comprising", will be understood to imply the inclusion of a stated integer or group of integers but not the exclusion of any other integer or group of integers.

The invention will now be further described by way of the following examples.

EXAMPLES

Example 1—MIC Values (μg/ml) of NCL812 and 195 for *Malassezia pachydermatis*

Introduction

The antifungal activity of robenidine (NCL 812) and NCL195 were assessed for antifungal activity against 13 canine isolates of *Malassezia pachydermatis.*

Materials and Method

There is no recommended Clinical & Laboratory Standards Institute (CLSI) standard for *M. pachydermatis*. In the literature there are a number of papers which have developed Minimum Inhibitory Concentration (MIC) methodology for *Malassezia* species isolated from both humans and animals (ie both lipophilic and non-lipophilic species). In all papers, the methodology has been altered from the original CLSI protocols in order to overcome four main problem areas involved in testing this yeast.

1) Finding a suitable growth medium for *Malassezia*, especially the lipophilic species. This growth medium is often supplemented with a dispersing agent (mild detergent) to overcome the problem of cellular clumping which occurs due to the butyrous nature of this yeast.

2) Increasing the inoculum size to counteract the slower growth rate of *Malassezia* compared to that of *Candida* species.

3) Increasing the incubation time to up to 72 hours, again to counteract the slower growth rate of *Malassezia* compared to that of *Candida* species.

4) Altering the definition of the MIC end point. Many authors refer to the MIC breakpoint as the level of 50% inhibition of growth, whilst others use a 90% or 100% inhibition level. When testing the azole group of antifungal agents, there is also the well known trailing end point problem with MIC determination. Trailing occurs when the turbidity continually decreases as the drug concentration increases but the suspension fails to become optically clear (partial inhibition of growth over an extended range of antifungal concentrations).

The following method was originally developed by Eichenberg et al. (2003) (mSAB broth microdilution method). The mSAB method was devised to follow as closely as possible the CLSI guidelines whilst still allowing for the distinct biochemical and growth requirements of *M. pachydermatis*. Sabouraud dextrose broth with 1% Tween 80 was chosen as the assay medium as it allowed for excellent growth of the organism. Higher inoculum concentrations (1-4×$10^6$ CFU/ml) and increased time of incubation (48 to 72 hours) were used to enable sufficient growth of the test strains.

Results

TABLE 5

| # | Malassezia isolate | MIC µg/ml NCL812 | MIC µg/ml NCL195 |
|---|---|---|---|
| 1 | M1-017 | 2 | 1 |
| 2 | M-018 | 2 | 1 |
| 3 | M-020 | 2 | 1 |
| 4 | M-036 | 1, 2 | 1 |
| 5 | M-037 | 2 | 1 |
| 6 | M-038 | 1 | 1 |
| 7 | M-040 | 2 | 0.5/1 |
| 8 | M-052 | 1 | 1 |
| 9 | M-055 | 1 | 1 |
| 10 | M-060 | 1 | 1 |
| 11 | M-066 | 1, 2 | 1 |
| 12 | M-067 | 1 | 0.5/1 |
| 13 | M-069 | 2 | 1 |

Conclusion

Both NCL812 and NCL195 were highly active against all 13 isolates of *Malassezia pachydermatis*.

References

Eichenberg M. L., Appelt C. E., Berg V., Muschner A. C., Nobre M. O., Matta D., Alves S. H. & Ferreiro L. 2003 Susceptibility of *Malassezia pachydermatis* to Azole Antifungal Agents Evaluated by a New Broth. Acta Scientiae Veterinariae. 31: 75-80.

Example 2—Individual MIC Value of EDTA, NCL812 Alone and in Combination for 10 Canine *Malassezia pachydermatis* Isolates Introduction The antifungal activity of robenidine (NCL 812) with and without the presence of EDTA was assessed against 13 isolates of *Malassezia pachydermatis*.

Materials and Methods

There is no recommended CLSI standard for *M. pachydermatis*. In the literature there are a number of papers which have developed MIC methodology for *Malassezia* species isolated from both humans and animals (ie both lipophilic and non-lipophilic species). In all papers the methodology has been altered from the original CLSI protocols in order to overcome four main problem areas involved in testing this yeast.

1) Finding a suitable growth medium for *Malassezia*, especially the lipophilic species. This growth medium is often supplemented with a dispersing agent (mild detergent) to overcome the problem of cellular clumping which occurs due to the butyrous nature of this yeast.

2) Increasing the inoculum size to counteract the slower growth rate of *Malassezia* compared to that of *Candida* species.

3) Increasing the incubation time to up to 72 hours, again to counteract the slower growth rate of *Malassezia* compared to that of *Candida* species.

4) Altering the definition of the MIC end point. Many authors refer to the MIC breakpoint as the level of 50% inhibition of growth, whilst others use a 90% or 100% inhibition level.

The method followed was originally developed by Eichenberg et al. (2003) (mSAB broth microdilution method). The mSAB method was devised to follow as closely as possible the CLSI guidelines whilst still allowing for the distinct biochemical and growth requirements of *M. pachydermatis*. Sabouraud dextrose broth with 1% Tween 80 was chosen as the assay medium as it allowed for excellent growth of the organism. Higher inoculum concentrations (1-4×$10^6$ CFU/ml) and increased time of incubation (48 to 72 hours) were used to enable sufficient growth of the test strains.

A modified two-dimensional microdilution checkerboard assay was used to evaluate the potential synergistic activity between NCL compounds and EDTA (Chan et al. 2019). Briefly, 150 µl of SDB+1% TW80 was added to each well of a 96-well microtiter plate, which was used as the checkerboard challenge plate. Next, a two-fold serial dilution of NCL 812 (robenidine) working solution was performed along the abscissa (column 3 to 12 only) (1/2 to 1/1024 dilution ratio). In another 96-well plate, EDTA was two-fold serially diluted in SDB+1% TW80 from 1/8 to 1/256 dilution concentration for *Malassezia* yeast. Then, 150 µl of each Epiotic SIS concentration was dispensed along the ordinate (row H to C) in the checkerboard challenge plate. Each plate was set up to test a single yeast isolate. 50 µl of yeast suspension (prepared at 1:100 dilution of 0.2-0.3 OD 600 nm) was added to each well of the plate to achieve a final inoculum concentration of 4-5×$10^3$ CFU/ml. Following incubation at 35±2° C. for 24-48 hours, minimal inhibitory concentration (MIC) values when tested alone and in combination were assessed both visually and spectrophotometrically ($OD_{600\ nm}$). Experiments were performed in duplicate and repeated twice.

(c) Fractional inhibitory concentration index (FICI) was determined as follows:

$$FICI = \frac{A}{MIC_A} + \frac{B}{MIC_B}$$

A and B are the MICs of NCL812 and EDTA, respectively, in the combination;

$MIC_A$ and $MIC_B$ are the MICs of NCL812 and EDTA alone, respectively;

The FICI values were interpreted as follows (Hamoud et al., 2015).

TABEL 6

| Synergy | FICI ≤ 0.5 |
|---|---|
| Addition/Partial Synergy | 0.5 < FICI ≤ 1.0 |
| Indifference | 1.0 < FICI < 4.0 |
| Antagonism | FICI ≥ 4.0 |

Results

Fractional inhibitory concentration index (FICI) was calculated and is shown in the Table below.

TABLE 7

| | | MIC μg/ml | | | | |
|---|---|---|---|---|---|---|
| | | Compound alone | | Combination | | |
| # | ISOLATE | EDTA | NCL812 | EDTA | NCL812 | FICI |
| 1 | *Candida albicans* | 95 | 4 | 47.5 | 1 | 0.75 |
| 2 | ML44 | 95 | 1 | 47.5 | 0.5 | 1 |
| 3 | ML18 | 95 | 1 | 47.5 | 0.5 | 1 |
| 4 | ML69 | 95 | 2 | 47.5 | 1 | 1 |
| 5 | ML42 | 48 | 2 | 23.75 | 1 | 1 |
| 6 | ML43 | 95 | 4 | 47.5 | 2 | 1 |
| 7 | ML41 | 48 | 2 | 23.75 | 0.5 | 0.75 |
| 8 | ML19 | 48 | 2 | 23.75 | 1 | 1 |
| 9 | ML21 | 48 | 2 | 23.75 | 1 | 1 |
| 10 | ML20 | 95 | 1 | 47.5 | 0.5 | 1 |
| 11 | ML36 | 95 | 2 | 47.5 | 1 | 1 |

Conclusion

Synergy was observed with each of the 11 isolates exposed to the combination of NCL812 and EDTA.

References

Chan W Y, Hickey E E, Khazandi M, Page S W, Trott D J, Hill P B. In vitro antimicrobial activity of monensin against common clinical isolates associated with canine otitis externa. Comp Immunol Microbiol Infect Dis. 2018 57:34-38

Eichenberg M. L., Appelt C. E., Berg V., Muschner A. C., Nobre M. O., Matta D., Alves S. H. & Ferreiro L. 2003 Susceptibility of *Malassezia pachydermatis* to Azole Antifungal Agents Evaluated by a New Broth. Acta Scientiae Veterinariae. 31: 75-80

Hamoud R, Reichling J, Wink M. Synergistic antibacterial activity of the combination of the alkaloid sanguinarine with EDTA and the antibiotic streptomycin against multidrug resistant bacteria. *J Pharm Pharmacol* 2015; 67:264-273

Example 3—Antifungal Susceptibility of Robenidine (NCL812) and Analogs NCL062, NCL195, NCL219, NCL259, NCL265 Against *Candida albicans* and *Candida parapsilosis*

Introduction

The antifungal susceptibility of robenidine (NCL812) and analogs NCL062, NCL195, NCL219, NCL259, NCL265 against two *Candida albicans* isolates and one *Candida parapsilosis* isolate was investigated.

Materials and Methods

Antifungal minimum inhibitory concentration (MIC) testing was undertaken as recommended by the CLSI. Briefly, antifungal susceptibility tests were performed for amphotericin B, robenidine (NCL812) and 5 robenidine analogs (NCL062, NCL195, NCL219, NCL259, NCL265) by standard broth microdilution method (CLSI) in RPMI 1640. Various concentrations (ranging from high to low) of the selected compounds were prepared in RPMI 1640 medium by double dilution in 96-well microtitre plates. Each well contained an inoculum of approximately $2\times10^3$ cells/mL. The wells without addition of drugs served as negative (no inoculum) and positive (inoculum only) growth controls. Microtitre plates were incubated at 35° C. for 24-48 hours. Growth was visually assessed as well as spectrophotometrically determining by measuring optical density at 600 nm at 24 and 48 hours, using a microplate reader (Multiskan-EX; Thermo Elect. Corp., USA) with the lowest concentration which recorded no growth identified as the MIC. Antifungal MICs were determined for each isolate in duplicate; if the values obtained were different, the MIC test was repeated a third time. Antifungal susceptibility tests were performed for amphotericin B and NCL analogs by standard broth microdilution method (CLSI). Briefly, various concentrations (ranging from high to low) of the selected compounds were prepared in RPMI 1640 medium by double dilution in the 96-well plates. Each well contained an inoculum of approximately $2\times10^3$ cells/mL. The wells without addition of drugs served as a negative control. Micro plates were incubated at 35° C. for 48 hour and read spectrophotometrically at 600 nm, using a microplate reader (Multiskan-EX; Thermo Elect. Corp., USA).

Results

The antifungal susceptibility results of robenidine (NCL812) and analogs NCL062, NCL195, NCL219, NCL259, NCL265 against two *Candida albicans* isolates and one *Candida parapsilosis* isolate are presented in the following table.

TABLE 8

| | MIC μg/ml | | | | | |
|---|---|---|---|---|---|---|
| | *Candida albicans* | | *Candida albicans* ATCC 90028 | | *Candida parapsilosis* ATCC 22019 | |
| COMPOUND | $1^{st}$ | $2^{nd}$ | $1^{st}$ | 2nd | 1st | 2nd |
| Amphotericin B | 0.5 | 1 | 0.25 | 0.5 | 0.5 | 0.5 |
| NCL812 | 0.5 | 1 | 0.25 | 0.5 | 0.5 | 0.5 |
| NCL062 | 0.5 | 1 | 1 | 1 | 0.5 | 1 |
| NCL195 | 2 | 2 | 2 | 2 | 1 | 2 |
| NCL219 | >32 | >32 | >32 | >32 | >32 | >32 |
| NCL259 | 4 | 4 | 4 | 8 | 4 | 4 |
| NCL265 | 2 | 4 | 2 | 2 | 2 | 2 |

Conclusion

Robenidine and 4 analogs were highly active (MIC 0.5-8 μg/ml) against two *Candida albicans* and one *Candida parapsilosis* isolates.

Reference

Clinical and Laboratory Standards Institute (CLSI). *Reference method for broth dilution antifungal susceptibility testing of yeasts.* $4^{th}$ ed. CLSI standard M27. ISBN 1-56238-827-4. Clinical and Laboratory Standards Institute. Wayne Pennsylvania, USA.

Example 4—the MIC Values (μg/Ml) of NCL Analogs for Two *Candida albicans* and Two *Cryptococcus neoformans*. Each MIC Test was Performed in Duplicate Introduction The antifungal activity of robenidine (NCL 812) and 27 analogs (NCL004, NCL020, NCL023, NCL024, NCL062, NCL094, NCL097, NCL110, NCL113, NCL114, NCL115, NCL135, NCL139, NCL180, NCL181, NCL195, NCL219, NCL220, NCL228, NCL247, NCL250, NCL259, NCL260, NCL263, NCL265, NCL269, NCL274) was assessed by determining the minimum inhibitory concentration of each compound against two isolates of *Candida albicans* and two isolates of *Cryptococcus neoformans* using the known antifungal compound, amphotericin B as a control agent.

Materials and Method

Antifungal minimum inhibitory concentration (MIC) testing was undertaken as recommended by the CLSI. Briefly, antifungal susceptibility tests were performed for amphotericin B, robenidine (NCL812) and robenidine (NCL) analogs (NCL004, NCL020, NCL023, NCL024, NCL062, NCL094, NCL097, NCL110, NCL113, NCL114, NCL115, NCL135, NCL139, NCL180, NCL181, NCL195, NCL219, NCL220, NCL228, NCL247, NCL250, NCL259, NCL260, NCL263, NCL265, NCL269, NCL274) by standard broth microdilution method (CLSI) in RPMI 1640. Various concentrations (ranging from high to low) of the selected compounds were prepared in RPMI 1640 medium by double dilution in 96-well microtitre plates. Each well contained an inoculum of approximately $2\times10^3$ cells/mL. The wells without addition of drugs served as negative (no inoculum) and positive (inoculum only) growth controls. Microtitre plates were incubated at 35° C. for 24-48 hours. Growth was visually assessed as well as spectrophotometrically determining by measuring optical density at 600 nm at 24 and 48 hours, using a microplate reader (Multiskan-EX; Thermo Elect. Corp., USA) with the lowest concentration which recorded no growth identified as the MIC. Antifungal MICs were determined for each isolate in duplicate; if the values obtained were different, the MIC test was repeated a third time.

Results

TABLE 9

| | | MIC (μg/ml) at 24-48 hours | | | |
|---|---|---|---|---|---|
| | | *Candida albicans* | | *Cryptococcus neoformans* | |
| # | COMPOUND | ATCC 90028 | SA3 | SA1 | SA2 |
| 1 | Amphotericin B | 0.5 | 2 | 0.3 | 0.3 |
| 2 | NCL812 | 2 | 2 | 2 | 2 |
| 3 | NCL023 | 32 | 32 | 16 | 16 |
| 4 | NCL062 | 1 | 1 | 1 | 1 |
| 5 | NCL097 | 32 | 8 | 16 | 16 |
| 6 | NCL113 | >32 | >32 | 4 | 4 |
| 7 | NCL115 | >32 | >32 | 8 | 8 |
| 8 | NCL219 | 32 | 16 | 2 | 2 |
| 9 | NCL220 | 32 | 32 | 2 | 4 |
| 10 | NCL195 | 2 | 2 | 2 | 2 |
| 11 | NCL259 | 16 | 16 | 2 | 2 |
| 12 | NCL265 | 8 | 8 | 1 | 1 |
| 13 | NCL004 | >32 | >32 | >32 | >32 |
| 14 | NCL020 | >32 | >32 | >32 | >32 |
| 15 | NCL024 | >32 | >32 | >32 | 32 |
| 16 | NCL094 | >32 | >32 | >32 | >32 |
| 17 | NCL110 | >32 | >32 | >32 | >32 |
| 18 | NCL114 | >32 | >32 | >32 | >32 |
| 19 | NCL135 | >32 | >32 | >32 | >32 |
| 20 | NCL139 | >32 | >32 | >32 | >32 |
| 21 | NCL180 | >32 | >32 | >32 | >32 |
| 22 | NCL181 | >32 | >32 | >32 | >32 |
| 23 | NCL228 | >32 | >32 | >32 | >32 |
| 24 | NCL247 | >32 | >32 | >32 | >32 |
| 25 | NCL250 | >32 | >32 | >32 | >32 |

TABLE 9-continued

| | | MIC (μg/ml) at 24-48 hours | | | |
|---|---|---|---|---|---|
| | | *Candida albicans* | | *Cryptococcus neoformans* | |
| # | COMPOUND | ATCC 90028 | SA3 | SA1 | SA2 |
| 26 | NCL260 | >32 | >32 | >32 | >32 |
| 27 | NCL263 | >32 | >32 | >32 | >32 |
| 28 | NCL269 | >32 | >32 | >32 | >32 |
| 29 | NCL274 | >32 | >32 | >32 | >32 |

Conclusion

Robenidine and analogs NCL023, NCL062, NCL097, NCL113, NCL115, NCL219, NCL220, NCL195, NCL259 and NCL265 were highly active against the two isolates of *Cryptococcus neoformans*, with MICs of 1-16 μg/mL. Against the two isolates of *Candida albicans* robenidine and 8 analogs (NCL023, NCL062, NCL097, NCL219, NCL220, NCL195, NCL259 and NCL265) displayed high antifungal activity.

Reference

Clinical and Laboratory Standards Institute (CLSI). *Reference method for broth dilution antifungal susceptibility testing of yeasts*. $4^{th}$ ed. CLSI standard M27. ISBN 1-56238-827-4. Clinical Laboratory Standards Institute. Wayne Pennsylvania, USA.

Example 5

Introduction

The antifungal activity of robenidine (NCL 812) and 10 analogs (NCL23, NCL24, NCL97, NCL113, NCL115, NCL195, NCL219, NCL220, NCL259, NCL265) was assessed by determining the minimum inhibitory concentration of each compound against a series of isolates of *Candida albicans* and *Cryptococcus neoformans* using the known antifungal compound, amphotericin B as a control agent.

Materials and Method

Antifungal minimum inhibitory concentration (MIC) testing was undertaken as recommended by the CLSI. Briefly, antifungal susceptibility tests were performed for amphotericin B, robenidine (NCL812) and robenidine analogs (NCL23, NCL24, NCL97, NCL113, NCL115, NCL195, NCL219, NCL220, NCL259, NCL265) by standard broth microdilution method (CLSI) in RPMI 1640. Various concentrations (ranging from high to low) of the selected compounds were prepared in RPMI 1640 medium by double dilution in 96-well microtitre plates. Each well contained an inoculum of approximately $2\times10^3$ cells/mL. The wells without addition of drugs served as negative (no inoculum) and positive (inoculum only) growth controls. Microtitre plates were incubated at 35° C. for 24-48 hours. Growth was visually assessed as well as spectrophotometrically determining by measuring optical density at 600 nm, using a microplate reader (Multiskan-EX; Thermo Elect. Corp., USA) at 24 and 48 hours with the lowest concentration which recorded no growth identified as the MIC. Antifungal MICs were determined for each isolate in duplicate; if the values obtained were different, the MIC test was repeated a third time.

Results

TABLE 10

The MIC values (μg/mL) of NCL analogs for two *Candida albicans* and two *Cryptococcus neoformans* isolates (1.1-1.4); and 10 clinical *Candida albicans* isolates (1-10). Each MIC test was performed in duplicate and repeated a third time if results were disparate.

| | Organism | MIC values of following NCL analogs and amphotericin B μg/mL | | | | | | | | | | | |
|---|---|---|---|---|---|---|---|---|---|---|---|---|---|
| | | NCL 812 | NCL 23 | NCL 24 | NCL 97 | NCL 113 | NCL 115 | NCL 195 | NCL 219 | NCL 220 | NCL 259 | NCL 265 | Amp B |
| 1.1 | *Candida albicans* ATCC 90028 | 2 | 32 | >32 | 32 | >32 | >32 | 2 | 32 | 32 | 16 | 8 | 0.5 |
| 1.2 | *C. albicans* SA3 | 2 | 32 | >32 | 8 | >32 | >32 | 2 | 16 | 32 | 16 | 8 | 2 |
| 1.3 | *Cryptococcus neoformans* SA1 | 2 | 16 | >32 | 16 | 4 | 8 | 2 | 2 | 2 | 2 | 1 | 0.25 |
| 1.4 | *Cryptococcus neoformans* SA2 | 2 | 16 | 32 | 16 | 4 | 8 | 2 | 2 | 4 | 2 | 1 | 0.25 |
| | CLINICAL ISOLATES OF *CANDIDA ALBICANS* | | | | | | | | | | | | |
| 1 | *C. albicans* 16-90050810 | 2 | >16 | >16 | 8 | 16 | >16 | 4 | >16 | >16 | >16 | 16 | 0.125 |
| 2 | *C. albicans* 16-46177400 | 4 | >16 | >16 | 8 | 16 | >16 | 4 | >16 | >16 | >16 | 16 | 0.25 |
| 3 | *C. albicans* 16-90054237 | 2 | 16 | 4 | 4 | 8 | >16 | 4 | >16 | 8 | 32 | 16 | 0.125 |
| 4 | *C. albicans* 18-144-00196 | 0.5 | 16 | 16 | 8-16 | 8 | >16 | 4 | >16 | 8 | >16 | >16 | 0.25 |
| 5 | *C. albicans* 15-45171061 | 1 | 16 | 16 | 4 | 8 | >16 | 8 | 8 | >16 | 8 | 8 | 0.125 |
| 6 | *C. albicans* 15-91329871 | 2 | 16 | >16 | 8 | 8 | >16 | 8 | >16 | 8 | >16 | 16 | 0.125 |
| 7 | *C. albicans* 18-148-08188 Azole Resistant (Fluconazole MIC 8 μg/mL) | 1 | 16 | >16 | 8 | 8 | >16 | >16 | >16 | 4 | >16 | 16 | 0.5 |
| 8 | *C. albicans* 14-90045999 Azole Resistant (Fluconazole MIC 64 μg/mL) | 2 | >16 | 4 | 8 | 8-16 | 8 | >16 | 4 | >16 | >16 | 16 | 0.25 |
| 9 | *C. albicans* 16-24136919 Azole Resistant (Fluconazole MIC 256 μg/mL) | 2 | 8 | 8 | 4-8 | 8 | >16 | 4 | >16 | 4 | 8 | 4 | 0.5 |
| 10 | *C. albicans* 12-93301752 Azole Resistant (Fluconazole MIC 32 μg/mL) | 2 | 16 | 8 | 8 | 8 | >16 | 4 | >16 | 4 | 16 | 2 | 0.5 |

Conclusion

Robenidine and 10 analogs (NCL023, NCL024, NCL097, NCL113, NCL115, NCL195, NCL219, NCL220, NCL259, NCL265) were all highly active against one or more isolates of *Cryptococcus neoformans* and *Candida albicans*. Robenidine and NCL097 were active against all tested isolates of *Cryptococcus neoformans* and *Candida albicans*

Reference

Clinical and Laboratory Standards Institute (CLSI). *Reference method for broth dilution antifungal susceptibility testing of yeasts.* $4^{th}$ ed. CLSI standard M27. ISBN 1-56238-827-4. Clinical Laboratory Standards Institute. Wayne Pennsylvania, USA.

Example 6

Introduction

The antifungal activity of robenidine (NCL 812) and 10 analogs (NCL023, NCL024, NCL097, NCL113, NCL115, NCL195, NCL219, NCL220, NCL259, NCL265) was assessed by determining the minimum inhibitory concentration of each compound against a series of isolates of *Candida albicans* and *Cryptococcus neoformans* using the known antifungal compound, amphotericin B as a control agent.

Materials and Method

Antifungal minimum inhibitory concentration (MIC) testing was undertaken as recommended by the CLSI (1). Briefly, antifungal susceptibility tests were performed for amphotericin B, robenidine (NCL812) and 10 robenidine analogs (NCL023, NCL024, NCL097, NCL113, NCL115, NCL195, NCL219, NCL220, NCL259, NCL265) by standard broth microdilution method (CLSI) in RPMI 1640. Various concentrations (ranging from high to low) of the selected compounds were prepared in RPMI 1640 medium by double dilution in 96-well microtitre plates. Each well contained an inoculum of approximately $2\times10^3$ cells/mL. The wells without addition of drugs served as negative (no inoculum) and positive (inoculum only) growth controls. Microtitre plates were incubated at 35° C. for 24-48 hours. Growth was visually assessed as well as spectrophotometrically determining by measuring optical density at 600 nm at 24 and 48 hours, using a microplate reader (Multiskan-EX; Thermo Elect. Corp., USA) with the lowest concentration which recorded no growth identified as the MIC. Antifungal MICs were determined for each isolate in duplicate; if the values obtained were different, the MIC test was repeated a third time.

Results

TABLE 11

The MIC values (μg/ml) of NCL analogs for two *Candida albicans* and two *Cryptococcus neoformans* isolates (1.1-1.4); and 10 clinical *C. neoformans* & *C. gattii* isolates (1-10)
Each MIC test was performed in duplicate and repeated a third time if results were disparate

| | | MIC values of following NCL analogs and amphotericin B μg/ml | | | | | | | | | | | |
|---|---|---|---|---|---|---|---|---|---|---|---|---|---|
| | Organism | NCL 812 | NCL 23 | NCL 24 | NCL 97 | NCL 113 | NCL 115 | NCL 195 | NCL 219 | NCL 220 | NCL 259 | NCL 265 | Amp B |
| 1.1 | *Candida albicans* ATCC 90028 | 2 | 32 | >32 | 32 | >32 | >32 | 2 | 32 | 32 | 16 | 8 | 0.5 |
| 1.2 | *C. albicans* SA3 | 2 | 32 | >32 | 8 | >32 | >32 | 2 | 16 | 32 | 16 | 8 | 2 |
| 1.3 | *Cryptococcus neoformans* SA1 | 2 | 16 | >32 | 16 | 4 | 8 | 2 | 2 | 2 | 2 | 1 | 0.3 |
| 1.4 | *Cryptococcus neoformans* SA2 | 2 | 16 | 32 | 16 | 4 | 8 | 2 | 2 | 4 | 2 | 1 | 0.3 |
| | HUMAN CLINICAL ISOLATES OF CRYPTOCOCCUS SPP | | | | | | | | | | | | |
| 1 | *C. neoformans* var *grubii* 17-93996964 | | 8 | 32 | 32 | 4 | >32 | 2 | >32 | 32 | 8 | 8 | 1 |
| 2 | *C. gatti* 17-90232099 | | 8 | 32 | 32 | 4 | >32 | 2 | >32 | 4 | 8 | 8 | 1 |
| 3 | *C. neoformans* serotype A/D hybrid | 16 | 8 | 32 | 16/32 | 4 | >32 | 2 | >32 | 32 | 8 | 8 | 0.5 |
| 4 | *C. gattii* 17-90028217 | 16 | 16 | 32 | 32 | 4-8 | >32 | 2 | >32 | 4 | 8, 16 | 4 | 0.5 |
| 5 | *C. neoformans* var *grubii* 16-90050434 | 32 | 8 | 32 | 16-32 | 4 | >32 | 2 | >32 | 32 | 8 | 4 | 1 |
| 6 | *C. neoformans* var *grubii* 17-93996464 | 16 | 8 | 32 | 32 | 4 | >32 | 2 | >32 | 32 | 8, 16 | 8 | 1 |
| 7 | *C. neoformans* var *grubii* 17-90028233 | 32 | 8 | 16 | 32 | 4 | >32 | 2 | >32 | >32 | 8 | 8 | 2 |
| 8 | *C. gattii* 17-90028211 | 16 | 16 | 8 | 16 | 4 | >32 | 2 | >32 | 32 | 8 | 8, 16 | 1 |
| 9 | *C. gattii* 17-90028242 | | 8 | 32 | 32 | 2-4 | >32 | 2 | >32 | 32 | 8 | 8 | 1 |
| 10 | *C. gattii* 16-90050373 | 16 | 8 | 16 | 16 | 2-4 | >32 | 2 | >32 | >32 | 8 | 8 | 1 |

Conclusion

Robenidine and all 10 analogs were highly active against one or more isolates of *Candida albicans* and *Cryptococcus neoformans*. Robenidine and NCL195 were active against all isolates with NCL195 displaying the most potent activity.

Reference

Clinical and Laboratory Standards Institute (CLSI). Reference method for broth dilution antifungal susceptibility testing of yeasts. 4th ed. CLSI standard M27. ISBN 1-56238-827-4. Clinical Laboratory Standards Institute. Wayne Pennsylvania, USA.

Example 7—Ex Vivo Antimicrobial Activity of Two Otic Formulations Containing Adjuvanted Robenidine Against *Malassezia pachydermatis*, a Yeast Commonly Associated with Canine Otitis Externa Background Otitis externa (OE) is one of the most commonly diagnosed infectious dermatological diseases in dogs. It can be caused by a number of pathogens, including bacteria such as *Pseudomonas aeruginosa, Staphylococcus pseudintermedius, Proteus mirabilis* and β-haemolytic *Streptococcus* spp., and the yeast, *Malassezia pachydermatis* (Chan et al 2019; Sim et al 2019).

The condition is usually treated topically with a combination of antibacterial drugs (such as those belonging to the fluoroquinolone, aminoglycoside and polymyxin classes) and antifungal drugs (such as those belonging to the azole, allylamine and polyene classes)(Sim et al 2019; von Silva-Tarouca et al 2019; Khazandi et al 2019). However, frequent use of antimicrobials has contributed to the development of antimicrobial resistance (AMR), which is increasingly becoming an issue in both human and veterinary medicine and has prompted the need for diligent antimicrobial stewardship (Chan et al 2019; Korbelik et al 2019). Many pathogens associated with canine OE are multidrug-resistant (MDR), including *P. aeruginosa, Staphylococcus* spp. and *Proteus* spp., and more recently *Malassezia*, making treatment increasingly difficult (Chan et al 2019; Sim et al 2019; Khazandi et al 2019).

AMR in companion animal pathogens is a potential public health concern. Transmission of antimicrobial-resistant bacteria and fungi can occur between animals and humans through direct or indirect contact, particularly in household and veterinary settings (Bourely et al 2019; Sim et al 2019). Transmission of MDR *P. aeruginosa, Escherichia coli* and methicillin-resistant *S. pseudintermedius* (MRSP) between dogs and humans has been documented in previous studies (Sim et al 2019; Khazandi et al 2019). Many antimicrobials used in veterinary medicine are within the same classes as drugs used to treat humans, therefore having the potential to increase AMR in humans (Sim et al 2019). Public health risks indicate the need to safeguard important drugs for both human and veterinary medicine, and to find novel treatments for animal diseases.

Repurposing of existing drugs not currently used in human medicine with known safety profiles as new antimicrobial classes is an approach to minimise the likelihood of cross-resistance development (Khazandi et al 2019). Robenidine has been used globally as an oral anticoccidial agent since the 1970s in rabbits and poultry (Khazandi et al 2019; Ogunniyi et al 2017). Recently, robenidine has been reported to exhibit antimicrobial activity against a number of Gram-positive bacteria, and as being effective against Gram-negative bacteria when combined with various adjuvants, suggesting that it may be a potential lead for further pharmaceutical development into products effective against MDR pathogens (Khazandi et al 2019; Abraham et al 2016). Most surprisingly, robenidine has been found to have antifungal activity against a range of organisms including various species of *Candida, Cryptococcus* and *Malassezia*, a finding not previously reported Adjuvants can be used to broaden the spectrum of activity of antimicrobials. Ethylenediaminetetraacetic acid (EDTA) is one such agent that has this effect (Finnegan and Percival 2015; Sim et al 2019). It is a bacteriostatic component of many topical human medications such as eyedrops, ear cleaners and ointments, and is also used intravenously or intramuscularly to treat lead poisoning (Finnegan and Percival 2015; Khazandi et al 2019). EDTA permeabilises the outer membrane of Gram-negative bacteria and has antibiofilm activity, including prevention of biofilm formation (Finnegan and Percival 2015; Sim et al 2019).

The aim of this study was to determine the antimicrobial activity of robenidine formulated in combination with adjuvants A (EDTA) and B (tetracaine) in either aqueous or non-aqueous bases against common canine OE pathogens using a novel ex vivo approach.

Materials and Methods

Animals

Ear swab samples were obtained from clinically affected dogs presenting at participating veterinary clinics in the outer northern suburbs of Adelaide. Two swab samples were obtained per infected ear and swab tips were immersed and stored in transport media to allow for survival of bacteria until ready for use in the laboratory.

Swab samples were kept at 4° C. using cold packs during transportation from veterinary clinics to the University of Adelaide Veterinary Diagnostic Laboratory (VDL). At the VDL, swabs were refrigerated at and subjected to testing within 3 days of submission.

TABLE 12

Investigational Veterinary Products (IVP)
2019 EX VIVO STUDY

| Constituent | Aqueous formulation | Non-aqueous formulation |
|---|---|---|
| NCL812 | 1 mg/g | 1 mg/g |
| EDTA Disodium | 40 mg/g | 40 mg/g |
| Tetracaine | 40 mg/g | 40 mg/g |
| Hydroxy Ethyl Cellulose | 3% w/w | — |
| Water | Up to 100% w/w | — |
| Aerosil R972 Pharma | — | 13% w/w |
| Miglyol 812 | — | Up to 100% w/w |

VDL Analysis

Gram staining, culturing of bacteria using agar plates and antibiotic sensitivity tests were performed at the VDL. One ear swab per pair was used for Gram staining and culturing, and bacteria and yeast were identified once grown. As well as the pathogen morphology result from the Gram stain, the presence of epithelial cells and polymorphonuclear cells in the sample was also noted. Before and after use, swabs were refrigerated at 4° C.

Time-Kill Kinetic Assays

Pure *Staphylococcus aureus* (ATCC strain 29213) and *P. aeruginosa* (ATCC strain 27853) cultures were tested in the ex vivo model as a necessary validation step prior to testing the diagnostic ear swabs. Pure bacterial cultures were grown from glycerol stocks on Sheep Blood agar (SBA) incubated at 37° C. for 12 hours and assessed for purity. Either heavy or light culture inocula of each bacterial species were prepared and added to vials containing either of the two robenidine products to be tested. Heavy cultures were obtained by running a swab over a line of heavy pure bacterial growth, covering the swab tip to produce a McFarland turbidity standard of at least 4.0 (equivalent to >$10^9$ CFU/mL). The swab was added to a vial containing PBS, following addition of the test product. Light cultures were obtained by adding a small number of bacterial colonies to a vial containing PBS, resulting in an absorbance reading of approximately 0.100 A (equivalent to a McFarland turbidity standard of 0.5 and $10^8$ CFU/mL). 2 mL of this solution was added to vials containing the test product. Test products were added to two separate vials, either with one containing the investigational formulation (1 g or 0.1 g) and the other the blank vehicle (1 g or 0.1 g), or with one containing 1 g Baytril Otic or 0.5 McFarland turbidity standard Baytril Otic (10 drops) and the other containing no product.

Vials were vortexed and immediately inoculated onto SBA within 5 minutes using 10 μL plastic inoculation loops and spread for single colonies. All plates, Baytril Otic and Baytril Otic blank vials were incubated at 37° C. The investigational formulations and blank vehicle vials were incubated at 37° C. and 300 RPM using an orbital mixer to facilitate adequate mixing of the oil-based formulation and PBS. Vials were removed from incubation at 4 and 8 h after the initial inoculation to allow solutions to again be inoculated onto agar plates. All plates and vials were returned to their respective incubators after inoculation.

Ear swabs were added to 5 mL sample collection vials containing 2 mL PBS and the product to be tested. Ear swabs in each pair were placed into two separate vials, either with one containing the investigational formulation (1 g or 0.1 g) and the other the blank vehicle (1 g or 0.1 g), or with one containing ten drops of Baytril Otic and the other containing no product. The ear swab used for Gram staining and culturing at the VDL was used for the blank vials while the unused swab was used for the investigational formulation and Baytril Otic vials.

Vials were vortexed and immediately inoculated onto Sheep Blood, MacConkey No. 3 and *Malassezia* selective agar plates using 10 μL plastic inoculation loops and spread for single colonies. 18 μL of glycerol was added to *Malassezia* selective agar plates prior to inoculation to allow for growth of *Malassezia* spp. MacConkey No. 3 plates were used when ear swabs contained *Pseudomonas* spp. or *Proteus* spp., *Malassezia* selective plates were used for ear swabs containing *Malassezia* spp. and Sheep Blood plates were used for all ear swabs and pure cultures.

Vials and plates were incubated as per the pure bacterial culture method, and inoculation again occurred at 4 and 8 h after the initial inoculation.

Analysis of Growth

Plates were removed from incubation and viewed the following morning, 13-15 hours after the final plating. The degree of bacterial or fungal growth was assessed according to the method outlined by Litster et al. (2007), where growth was recorded as being very light (1-9 colonies, equivalent to 100-1000 CFU/mL), light (10-100 colonies, equivalent to 1000-10,000 CFU/mL), moderate (approximately 100 colonies or growth on the first set of streak lines, equivalent to 10,000 CFU/mL) or heavy (>100 colonies or growth on the second and final sets of streak lines, equivalent to ≥100,000 CFU/mL).

Results

Bacteria

The two investigational formulations killed or significantly decreased the growth of the pure bacterial cultures of *S. aureus* and *P. aeruginosa*. The light culture (1 g; 0.5 McFarland standard) of *S. aureus* was killed at 8 h compared with continuous heavy growth in the control plates. The heavy (1 g) and heavy (0.1 g) cultures showed very light and light growth at 8 h, respectively, in comparison to heavy and moderate growth in the control plates. The light (1 g), heavy (1 g) and heavy (0.1 g) cultures of *P. aeruginosa* were killed at 4, 4 and 8 h respectively, in comparison to heavy growth in the control plates.

The investigational formulation and Baytril Otic exhibited similar effectiveness at killing pure bacterial cultures of *S. aureus* and *P. aeruginosa.* 1 g of each investigational formulation was comparable to ten drops of Baytril Otic, using the recommended doses of these products. Each formulation killed the light (1 g/10 drops) and heavy (1 g) cultures of *P. aeruginosa* at 4 h, and each killed the light (1 g/10 drops) culture of *S. aureus* at 8 h. The heavy (1 g) culture of *S. aureus* was killed at 8 h by Baytril Otic.

*Malassezia* spp.

*Malassezia* spp. from swabs 19-01877, 19-01881, 19-01978 and from swabs 19-01868, 19-01881, 19-01899 were killed at 4 h when exposed to the non-aqueous or aqueous investigational formulation respectively, compared with varying levels of growth in the control plates. The swabs contained varying numbers of *Malassezia* yeast from moderate to high and all growth was killed at 4 h by the investigational formulations.

The robenidine otic formulations were effective at killing and/or inhibiting the growth of all pathogens obtained from diagnostic ear swabs. They were found to be effective at an inoculation of both 1 g and 0.1 g, killing all pathogens over 8 h in all tested ear swabs when 1 g was used. The 0.1 g dose resulted in killing of pathogens at 4 h in most cases and light growth at 8 h in others. Not unexpectedly, the 0.1 g dose appeared to kill pathogens at a slower rate in comparison to the 1 g dose, but was nevertheless still effective at killing the tested bacteria in comparison to the control plates.

The investigational formulations were effective at killing both Gram-positive and Gram-negative organisms associated with canine OE, as well as *Malassezia* yeast. This study is the first to report the effects of a formulation containing robenidine against *Malassezia* spp. The investigational formulations were very effective at killing *Malassezia* yeast with all tested pathogens being killed at 4 h in comparison to varying levels of growth in the control plates. This is significant as antifungal resistance is becoming an increasing issue in veterinary and human medicine (Kano et al 2020; Bhanderi et al 2009).

Conclusion

Robenidine in aqueous and non-aqueous vehicles, displayed rapid anti-*Malassezia* activity when assessed against isolates from cases of canine otitis externa.

References

Abraham, R. J., Stevens, A. J., Young, K. A., Russell, C., Qvist, A., Khazandi, M., Wong, H. S., Abraham, S., Ogunniyi, A. D., Page, S. W. and O'Handley, R., 2016. Robenidine analogs as gram-positive antibacterial agents. *Journal of medicinal chemistry,* 59(5), pp. 2126-2138.

Bhanderi, B. B., Yadav, M. M. and Roy, A., 2009. Antifungal drug resistance-concerns for veterinarians. *Veterinary World,* 2(5), pp. 204.

Bourély, C., Cazeau, G., Jarrige, N., Leblond, A., Madec, J. Y., Haenni, M. and Gay, E., 2019. Antimicrobial resistance patterns of bacteria isolated from dogs with otitis. *Epidemiology & Infection,* 147.

Chan, W. Y., Khazandi, M., Hickey, E. E., Page, S. W., Trott, D. J. and Hill, P. B., 2019. In vitro antimicrobial activity of seven adjuvants against common pathogens associated with canine otitis externa. *Veterinary dermatology,* 30(2), pp. 133-e38.

Finnegan, S. and Percival, S. L., 2015. EDTA: an antimicrobial and antibiofilm agent for use in wound care. *Advances in wound care,* 4(7), pp. 415-421.

Kano, R., Aramaki, C., Murayama, N., Mori, Y., Yamagishi, K., Yokoi, S. and Kamata, H., 2020. High multi-azole-resistant *Malassezia pachydermatis* clinical isolates from canine *Malassezia* dermatitis. *Medical Mycology,* 58(2): 197-200

Khazandi, M., Pi, H., Chan, W. Y., Ogunniyi, A. D., Sim, J. X. F., Venter, H., Garg, S., Page, S. W., Hill, P. B., McCluskey, A. and Trott, D. J., 2019. In vitro Antimicrobial Activity of Robenidine, Ethylenediaminetetraacetic Acid and Polymyxin B Nonapeptide Against Important Human and Veterinary Pathogens. *Frontiers in microbiology,* 10, pp. 837.

Korbelik, J., Singh, A., Rousseau, J. and Weese, J. S., 2019. Characterization of the otic bacterial microbiota in dogs with otitis externa compared to healthy individuals. *Veterinary dermatology,* 30(3), pp. 228-e70.

Litster, A., Moss, S. M., Honnery, M., Rees, B. and Trott, D. J., 2007. Prevalence of bacterial species in cats with clinical signs of lower urinary tract disease: recognition of *Staphylococcus felis* as a possible feline urinary tract pathogen. *Veterinary microbiology,* 121(1-2), pp. 182-188.

Sim, J. X. F., Khazandi, M., Pi, H., Venter, H., Trott, D. J. and Deo, P., 2019. Antimicrobial effects of cinnamon essential oil and cinnamaldehyde combined with EDTA against canine otitis externa pathogens. *Journal of applied microbiology,* 127(1), pp. 99-108.

von Silva-Tarouca, M. S., Wolf, G. and Mueller, R. S., 2019. Determination of minimum inhibitory concentrations for silver sulfadiazine and other topical antimicrobial agents against strains of *Pseudomonas aeruginosa* isolated from canine otitis externa. *Veterinary dermatology,* 30(2), pp. 145-e42.

Example 8—Investigation of the Safety and Efficacy of Two Novel Canine Otic Products Introduction Following the successful outcome of the ex vivo study described in Example 7, a study in dogs with otitis externa was designed to assess the safety and microbiological efficacy of the topical application of two novel products formulated as aqueous or non-aqueous combinations of robenidine, EDTA and tetracaine.

Methods

Test Animals

Dogs selected from a colony of beagles and fox hounds with a natural incidence of otitis externa.

TABLE 13

Investigational Veterinary Products (IVP) 2020 IN VIVO STUDY

| Constituent | Aqueous formulation | Non-aqueous formulation |
|---|---|---|
| NCL812 | 1 mg/g | 1 mg/g |

TABLE 13-continued

| Investigational Veterinary Products (IVP) 2020 IN VIVO STUDY | | |
|---|---|---|
| Constituent | Aqueous formulation | Non-aqueous formulation |
| EDTA Disodium | 40 mg/g | 40 mg/g |
| Tetracaine | 40 mg/g | 40 mg/g |
| Hydroxy Ethyl Cellulose | 2.5% w/w | — |
| Water | Up to 100% w/w | — |
| Aerosil R972 Pharma | — | 4.5% w/w |
| Miglyol 812 | — | Up to 100% w/w |

On each occasion, 1 mL of the IVP was administered by gentle manual expulsion from a volume calibrated syringe into the external ear canal of the recipient dog.

Procedure 20 dogs (mixed breed, age and gender) were selected from the test site colony for routine ear treatment using a reference product (Otoflush). Each ear canal was examined and rated (using the 0-3 scale Ear Scoring System described by Nuttall and Bensignor (2014)) and the health of the ear canal was recorded immediately before treatment and at 7-8 hrs, 24 and 48 hrs following treatment.

Assessment of safety and efficacy of 2 IVP otic product formulations was then undertaken. Administration into the external ear canal was followed by observation of response to treatment, taking swabs for microbiological investigation before treatment, and at 24 h, 14 and 28 days following administration.

Initially one dog was selected for treatment with each IVP. The product was administered into 1 ear canal. The ear canal was examined and rated as above and the health of the ear canal immediately before treatment, and at 7-8 hrs, 24 and 48 hrs following treatment was recorded.

Following the successful treatment of a single dog, a further 5 dogs were selected for treatment with each IVP which was administered into one ear canal of each dog. The ear canal was examined and rated as above and the health of the ear canal immediately before treatment, and at 7-8 hrs, 24 and 48 hrs following treatment was recorded.

Following the successful treatment of 6 dogs, a further 10 dogs were selected for treatment with each IVP which was administered into both ear canals of each dog. The ear canal was examined and rated as above and the health of the ear canal immediately before treatment, and at 7-8 hrs, 24 and 48 hrs following treatment was recorded.

Swabs for microbiological assessment were taken immediately before each treatment and at 24 hrs, 14 and 28 days.

Results

No treatment related adverse effects or behavioural reactions were observed in any of the treated dogs. *Malassezia* present prior to treatment was significantly reduced or eliminated at each post treatment assessment.

Conclusion

Each of the IVPs was found to be safe and effective when administered directly into the external ear canal of dogs.

Reference

Nuttall, T. and E. Bensignor (2014). "A pilot study to develop an objective clinical score for canine otitis externa." *Vet Dermatol* 25(6): 530-537, e591-532.

Example 9—The Antifungal Activity of Robenidine and a Library of Analogs

Introduction

This study was undertaken to determine the activity of robenidine and a series of analogs against the fungal species *Candida albicans.*

Method

The antifungal activity of 201 NCL analogs against *Candida albicans* ATCC14053 in vitro was investigated. A broth micro-dilution method was used, according to CLSI guidelines as described. NCL analogs were dissolved in DMSO and originally screened at a single concentration of 16 μg/mL. Analogs inhibiting growth of *C. albicans* at 16 μg/mL were further screened to determine the minimum inhibitory concentration (MIC-determined as the first concentration which inhibited growth) (test range 0.25-64 μg/mL. *C. albicans* was grown on sabouraud dextrose agar and prepared to a suspension equivalent to a 0.5 McFarland standard in PBS before a 1:200 dilution in RPMI (without sodium bicarbonate, with MOPS and glucose (2%)) into the final assay. A total volume of 200 μl per well was used with a final DMSO concentration of 1%. Assays were incubated at 37° C. for 20-24 hrs and run in duplicate.

Results

The following table summarises the results of the screening of the NCL library at 16 μg/mL and the minimum inhibitory concentration (MIC) of each analog that was identified in the screen as active at the screening discriminating concentration.

TABLE 14

| Agent | Screen at 16 μg/mL | MIC μg/mL | Agent | Screen at 16 μg/mL | MIC μg/mL |
|---|---|---|---|---|---|
| NCL812 | No growth | 0.5 | NCL162 | Growth | NA |
| NCL001 | Growth | NA | NCL163 | Growth | NA |
| NCL002 | Growth | NA | NCL166 | Growth | NA |
| NCL004 | Growth | NA | NCL167 | Growth | NA |
| NCL006 | Growth | NA | NCL170 | Growth | NA |
| NCL007 | Growth | NA | NCL171 | No growth | 2, 4 |
| NCL010 | Growth | NA | NCL172 | Growth | NA |
| NCL011 | Growth | NA | NCL175 | Growth | NA |
| NCL012 | Growth | NA | NCL177 | Growth | NA |
| NCL013 | Growth | NA | NCL178 | Growth | NA |
| NCL015 | Growth | NA | NCL179 | Growth | NA |
| NCL016 | Growth | NA | NCL180 | Growth | NA |
| NCL017 | Growth | NA | NCL181 | Growth | NA |
| NCL018 | Growth | NA | NCL184 | Growth | NA |
| NCL019 | Growth | NA | NCL185 | Growth | NA |
| NCL020 | Growth | NA | NCL187 | Growth | NA |
| NCL021 | No growth | 0.5, 1 | NCL188 | Growth | NA |
| NCL022 | Growth | NA | NCL189 | Growth | NA |
| NCL023 | No growth | 8, 16 | NCL190 | Growth | NA |

TABLE 14-continued

| Agent | Screen at 16 μg/mL | MIC μg/mL | Agent | Screen at 16 μg/mL | MIC μg/mL |
|---|---|---|---|---|---|
| NCL024 | Growth | NA | NCL192 | Growth | NA |
| NCL026 | Growth | NA | NCL193 | Growth | NA |
| NCL027 | No growth | 8, 16 | NCL195 | No growth | 1, 2 |
| NCL028 | Growth | NA | NCL196 | Growth | NA |
| NCL029 | Growth | NA | NCL197 | Growth | NA |
| NCL030 | Growth | NA | NCL198 | Growth | NA |
| NCL031 | Growth | NA | NCL199 | Growth | NA |
| NCL033 | Growth | NA | NCL201 | Growth | NA |
| NCL036 | Growth | NA | NCL202 | Growth | NA |
| NCL037 | Growth | NA | NCL203 | Growth | NA |
| NCL038 | No growth | 2, 4 | NCL204 | Growth | NA |
| NCL039 | No growth | 4, 8 | NCL205 | Growth | NA |
| NCL040 | No growth | 8, 16 | NCL206 | Growth | NA |
| NCL041 | Growth | NA | NCL207 | Growth | NA |
| NCL042 | Growth | NA | NCL208 | Growth | NA |
| NCL043 | Growth | NA | NCL211 | Growth | NA |
| NCL044 | Growth | NA | NCL212 | Growth | NA |
| NCL045 | Growth | NA | NCL213 | Growth | NA |
| NCL046 | Growth | NA | NCL214 | Growth | NA |
| NCL052 | Growth | NA | NCL215 | Growth | NA |
| NCL053 | Growth | NA | NCL216 | Growth | >64 |
| NCL054 | No growth | 4, 8 | NCL217 | No growth | 4 |
| NCL061 | Growth | NA | NCL218 | Growth | NA |
| NCL062 | Growth | NA | NCL219 | Growth | >64 |
| NCL093 | Growth | NA | NCL220 | Growth | >64 |
| NCL094 | Growth | NA | NCL221 | Growth | NA |
| NCL095 | Growth | NA | NCL222 | Growth | NA |
| NCL096 | Growth | NA | NCL223 | Growth | NA |
| NCL097 | No growth | 0.5 | NCL224 | Growth | NA |
| NCL098 | Growth | NA | NCL225 | Growth | NA |
| NCL099 | Growth | NA | NCL226 | Growth | NA |
| NCL100 | Growth | NA | NCL227 | Growth | >64 |
| NCL101 | No growth | 16, >64 | NCL228 | No growth | 0.5, 1 |
| NCL102 | Growth | NA | NCL229 | Growth | NA |
| NCL104 | Growth | NA | NCL230 | Growth | NA |
| NCL105 | No growth | 2, 4 | NCL231 | Growth | NA |
| NCL106 | Growth | NA | NCL232 | Growth | NA |
| NCL107 | No growth | 2, 4 | NCL233 | Growth | NA |
| NCL108 | Growth | NA | NCL234 | Growth | NA |
| NCL109 | Growth | NA | NCL235 | Growth | NA |
| NCL110 | Growth | NA | NCL236 | Growth | NA |
| NCL112 | Growth | NA | NCL237 | Growth | NA |
| NCL113 | No growth | 4, 8 | NCL238 | Growth | NA |
| NCL114 | Growth | NA | NCL239 | Growth | NA |
| NCL115 | Growth | NA | NCL241 | Growth | NA |
| NCL116 | Growth | NA | NCL242 | Growth | NA |
| NCL117 | Growth | NA | NCL243 | No growth | 16, 32 |
| NCL118 | Growth | NA | NCL244 | Growth | >64 |
| NCL119 | Growth | NA | NCL245 | Growth | NA |
| NCL120 | Growth | NA | NCL246 | Growth | NA |
| NCL121 | No growth | 4, 8 | NCL247 | No growth | 2, 4 |
| NCL122 | Growth | NA | NCL248 | Growth | NA |
| NCL123 | No growth | 1 | NCL249 | Growth | NA |
| NCL124 | Growth | NA | NCL250 | Growth | NA |
| NCL125 | Growth | NA | NCL252 | Growth | NA |
| NCL126 | No growth | 4 | NCL253 | Growth | NA |
| NCL127 | Growth | NA | NCL254 | No growth | 8 |
| NCL129 | Growth | NA | NCL255 | Growth | NA |
| NCL130 | Growth | NA | NCL256 | Growth | NA |
| NCL131 | Growth | NA | NCL258 | Growth | NA |
| NCL132 | Growth | NA | NCL259 | No growth | 8, 16 |
| NCL133 | Growth | NA | NCL260 | Growth | NA |
| NCL134 | No growth | <1 | NCL261 | Growth | NA |
| NCL135 | Growth | NA | NCL262 | Growth | NA |
| NCL136 | Growth | NA | NCL263 | Growth | NA |
| NCL137 | Growth | NA | NCL264 | Growth | NA |
| NCL138 | Growth | NA | NCL265 | No growth | 2 |
| NCL139 | No growth | <0.5 | NCL266 | No growth | 4 |
| NCL140 | No growth | 1, 2 | NCL267 | Growth | NA |
| NCL141 | Growth | NA | NCL268 | No growth | 4 |
| NCL143 | Growth | NA | NCL269 | Growth | NA |
| NCL144 | Growth | NA | NCL270 | Growth | NA |
| NCL145 | Growth | NA | NCL271 | No growth | 1 |
| NCL146 | No growth | 4, 8 | NCL272 | Growth | NA |
| NCL147 | Growth | NA | NCL273 | Growth | NA |
| NCL148 | Growth | NA | NCL274 | No growth | 2 |
| NCL149 | Growth | NA | NCL275 | Growth | NA |

TABLE 14-continued

| Agent | Screen at 16 μg/mL | MIC μg/mL | Agent | Screen at 16 μg/mL | MIC μg/mL |
|---|---|---|---|---|---|
| NCL150 | No growth | 1 | NCL276 | Growth | NA |
| NCL151 | Growth | NA | NCL277 | Growth | NA |
| NCL152 | Growth | NA | NCL278 | Growth | NA |
| NCL153 | Growth | NA | NCL279 | Growth | NA |
| NCL154 | Growth | NA | NCL280 | Growth | NA |
| NCL155 | Growth | NA | NCL281 | Growth | NA |
| NCL156 | Growth | NA | NCL282 | No growth | ≤0.25, 0.5 |
| NCL160 | No growth | 1, 2 | NCL283 | Growth | NA |

NA Not applicable

Conclusion

The screening concentration (16 μg/mL) was very low and selected in order to identify the most active agents in the NCL library. Robenidine and 35 analogs were identified as having high activity against *Candida albicans* at the low discriminating concentration. Amongst these highly active agents were compounds with an MIC less than 0.25 μg/mL (the lowest concentration tested).

References

Abraham, R. J., Stevens, A. J., Young, K. A., Russell, C., Qvist, A., Khazandi, M., Wong, H. S., Abraham, S., Ogunniyi, A. D., Page, S. W. and O'Handley, R., 2016. Robenidine analogs as gram-positive antibacterial agents. *Journal of medicinal chemistry,* 59(5), pp. 2126-2138.

Bhanderi, B. B., Yadav, M. M. and Roy, A., 2009. Antifungal drug resistance-concerns for veterinarians. *Veterinary World,* 2(5), pp. 204.

Bourély, C., Cazeau, G., Jarrige, N., Leblond, A., Madec, J. Y., Haenni, M. and Gay, E., 2019. Antimicrobial resistance patterns of bacteria isolated from dogs with otitis. *Epidemiology & Infection,* 147

Caused by Specific Point Mutations in the Squalene Epoxidase Gene." Antimicrob Agents Chemother 61(7).

Chan, W. Y., Khazandi, M., Hickey, E. E., Page, S. W., Trott, D. J. and Hill, P. B., 2019. In vitro antimicrobial activity of seven adjuvants against common pathogens associated with canine otitis externa. *Veterinary dermatology,* 30(2), pp. 133-e38.

Chan W Y, Hickey E E, Khazandi M, Page S W, Trott D J, Hill P B. In vitro antimicrobial activity of monensin against common clinical isolates associated with canine otitis externa. Comp Immunol Microbiol Infect Dis. 2018 57:34-38.

Clinical and Laboratory Standards Institute (CLSI). *Reference method for broth dilution antifungal susceptibility testing of yeasts.* $4^{th}$ ed. CLSI standard M27. ISBN 1-56238-827-4. Clinical Laboratory Standards Institute. Wayne Pennsylvania, USA.

Digby, S. S., M. Hald, M. C. Arendrup, S. V. Hjort and K. Kofoed (2017). "Darier Disease Complicated by Terbinafine-resistant *Trichophyton* rubrum: A Case Report." Acta Derm Venereol 97(1): 139-140.

Ebert, A., M. Monod, K. Salamin, A. Burmester, S. Uhrlass, C. Wiegand, U. C. Hipler, C. Kruger, D. Koch, F. Wittig, S. B. Verma, A. Singal, S. Gupta, R. Vasani, A. Saraswat, R. Madhu, S. Panda, A. Das, M. M. Kura, A. Kumar, S. Poojary, S. Schirm, Y. Graser, U. Paasch and P. Nenoff (2020). "Alarming India wide phenomenon of antifungal resistance in dermatophytes: A multicentre study." Online. Mycoses. 2020 Apr. 16

Eichenberg M. L., Appelt C. E., Berg V., Muschner A. C., Nobre M. O., Matta D., Alves S. H. & Ferreiro L. 2003 Susceptibility of *Malassezia pachydermatis* to Azole Antifungal Agents Evaluated by a New Broth. Acta Scientiae Veterinariae. 31: 75-80.

Finnegan, S. and Percival, S. L., 2015. EDTA: an antimicrobial and antibiofilm agent for use in wound care. *Advances in wound care,* 4(7), pp. 415-421.

Hamoud R, Reichling J, Wink M. Synergistic antibacterial activity of the combination of the alkaloid sanguinarine with EDTA and the antibiotic streptomycin against multidrug resistant bacteria. *J Pharm Pharmacol* 2015; 67:264-273.

Hiruma, J., H. Kitagawa, H. Noguchi, R. Kano, M. Hiruma, H. Kamata and K. Harada (2019). "Terbinafine-resistant strain of *Trichophyton* interdigitale strain isolated from a tinea pedis patient." J Dermatol 46(4): 351-353.

Kano, R., Aramaki, C., Murayama, N., Mori, Y., Yamagishi, K., Yokoi, S. and Kamata, H., 2020. High multi-azole-resistant *Malassezia pachydermatis* clinical isolates from canine *Malassezia* dermatitis. *Medical Mycology,* 58(2): 197-200.

Khazandi, M., Pi, H., Chan, W. Y., Ogunniyi, A. D., Sim, J. X. F., Venter, H., Garg, S., Page, S. W., Hill, P. B., McCluskey, A. and Trott, D. J., 2019. In vitro Antimicrobial Activity of Robenidine, Ethylenediaminetetraacetic Acid and Polymyxin B Nonapeptide Against Important Human and Veterinary Pathogens. *Frontiers in microbiology,* 10, pp. 837.

Korbelik, J., Singh, A., Rousseau, J. and Weese, J. S., 2019. Characterization of the otic bacterial microbiota in dogs with otitis externa compared to healthy individuals. *Veterinary dermatology,* 30(3), pp. 228-e70.

Litster, A., Moss, S. M., Honnery, M., Rees, B. and Trott, D. J., 2007. Prevalence of bacterial species in cats with clinical signs of lower urinary tract disease: recognition of *Staphylococcus felis* as a possible feline urinary tract pathogen. *Veterinary microbiology,* 121(1-2), pp. 182-188.

Monod, M. (2019a). "Antifungal resistance in dermatophytes: Emerging problem and challenge for the medical community." J Mycol Med 29(4): 283-284.

Monod, M., M. Feuermann, K. Salamin, M. Fratti, M. Makino, M. M. Alshahni, K. Makimura and T. Yamada (2019b). "*Trichophyton* rubrum Azole Resistance Mediated by a New ABC Transporter, TruMDR3." Antimicrob Agents Chemother 63(11).

Nenoff, P., S. B. Verma, R. Vasani, A. Burmester, U. C. Hipler, F. Wittig, C. Kruger, K. Nenoff, C. Wiegand, A. Saraswat, R. Madhu, S. Panda, A. Das, M. Kura, A. Jain, D. Koch, Y. Graser and S. Uhrlass (2019). "The current Indian epidemic of superficial dermatophytosis due to *Trichophyton* mentagrophytes-A molecular study." Mycoses 62(4): 336-356.

Osborne, C. S., I. Leitner, B. Favre and N. S. Ryder (2005). "Amino acid substitution in *Trichophyton* rubrum squalene epoxidase associated with resistance to terbinafine." Antimicrob Agents Chemother 49(7): 2840-2844.

Osborne, C. S., I. Leitner, B. Hofbauer, C. A. Fielding, B. Favre and N. S. Ryder (2006). "Biological, biochemical, and molecular characterization of a new clinical *Trichophyton* rubrum isolate resistant to terbinafine." Antimicrob Agents Chemother 50(6): 2234-2236.

Saunte, D. M. L., R. K. Hare, K. M. Jorgensen, R. Jorgensen, M. Deleuran, C. O. Zachariae, S. F. Thomsen, L. Bjornskov-Halkier, K. Kofoed and M. C. Arendrup (2019). "Emerging Terbinafine Resistance in *Trichophyton*: Clinical Characteristics, Squalene Epoxidase Gene Mutations, and a Reliable EUCAST Method for Detection." Antimicrob Agents Chemother 63(10).

Schosler, L., L. K. Andersen, M. C. Arendrup and M. Sommerlund (2018). "Recurrent terbinafine resistant *Trichophyton* rubrum infection in a child with congenital ichthyosis." Pediatr Dermatol 35(2): 259-260.

Sim, J. X. F., Khazandi, M., Pi, H., Venter, H., Trott, D. J. and Deo, P., 2019. Antimicrobial effects of cinnamon essential oil and cinnamaldehyde combined with EDTA against canine otitis externa pathogens. *Journal of applied microbiology,* 127(1), pp. 99-108.

von Silva-Tarouca, M. S., Wolf, G. and Mueller, R. S., 2019. Determination of minimum inhibitory concentrations for silver sulfadiazine and other topical antimicrobial agents against strains of *Pseudomonas aeruginosa* isolated from canine otitis externa. *Veterinary dermatology,* 30(2), pp. 145-e42.

Yamada, T., M. Maeda, M. M. Alshahni, R. Tanaka, T. Yaguchi, O. Bontems, K. Salamin, M. Fratti and M. Monod (2017). "Terbinafine Resistance of *Trichophyton* Clinical Isolates" *Anitmicrob Agents Chemother, June* 27, 61(7), 115-117.

The invention claimed is:

1. A method of treating a fungal colonisation or infection caused by a fungal agent in a subject, the method comprising the step of: administering to a subject in need thereof a therapeutically effective amount of a compound of Formula VIII, a stereoisomer, tautomer, pharmaceutically acceptable salt, or prodrug thereof:

Formula VIII

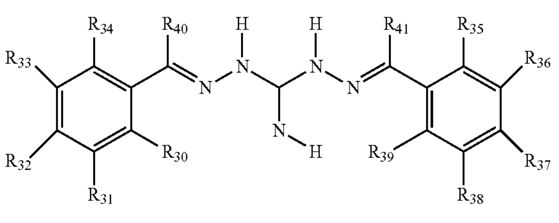

wherein $R_{30}$, $R_{34}$, $R_{35}$, and $R_{39}$ are H;

wherein $R_{31}$ and $R_{38}$ are H or OH;

wherein $R_{32}$ is OH, Cl, Br, F, or $R_{32}$ and $R_{33}$ are bonded together to form a quinoline-6;

wherein $R_{37}$ is OH, Cl, Br, F, or $R_{37}$ and $R_{36}$ are bonded together to form a quinoline-6;

wherein $R_{33}$ and $R_{36}$ are H, OH, or F; and wherein $R_{40}$ and $R_{41}$ are H or methyl.

2. The method according to claim 1, wherein the compound is selected from: NCL021; NCL062; NCL097; NCL123; NCL812.

3. The method according to claim 1, wherein the fungal agent is *Absidia* spp.; *Acremonium* spp.; *Actinomucor* spp.; *Albugo candida; Alternaria alternata; Alternaria brassicae; Alternaria brassicicola; Alternaria helianthi; Alternaria solani; Alternaria* spp.; *Apophysomyces elegans; Armillaria* spp.; *Ascochyta pisi; Ascosphaera apis; Aspergillus* spp.; *Aspergillus alabamensis; Aspergillus algerae; Aspergillus alliaceus* (teleomorph *Petromyces alliaceus*); *Aspergillus avenaceus; Aspergillus caesiellus; Aspergillus calidoustus; Aspergillus candidus; Aspergillus carneus; Aspergillus clavatus; Aspergillus connori; Aspergillus flavipes; Aspergillus flavus; Aspergillus fumigatus; Aspergillus glaucus; Aspergillus granulosus; Aspergillus insuetus; Aspergillus keveii; Aspergillus lentulus; Aspergillus nidulans* (*Emericella nidulans*); *Aspergillus niger; Aspergillus novofumigatus; Aspergillus ochraceus; Aspergillus pseudodeflectus; Aspergillus puniceus; Aspergillus quadrilineatus; Aspergillus restrictus; Aspergillus sydowii; Aspergillus tamarii; Aspergillus tanneri; Aspergillus terreus; Aspergillus thermomutatus* (teleomorph *Neosartorya pseudofischeri*); *Aspergillus tubingensis; Aspergillus udagawae* (*Neosartorya udagawae*); *Aspergillus versicolor; Aspergillus vesicularum; Aspergillus viridinutans; Aspergillus vitus* (teleomorph *Eurotium amstelodami*); *Aspergillus wentii, Austropuccinia psidii* (formerly *Puccinia psidii*, initially identified as *Uredo rangelii*); *Basidiobolus* spp.; *Batrachochytrium dendrobatidis; Batrachochytrium salamandrivorans; Biatriospora* spp.; *Bipolaris* spp.; *Bipolaris maydis; Bipolaris zeicola; Blastomyces dermatitidis; Blastomyces gilchristii; Blastomyces helicus; Blastomyces parvus; Blastomyces percursus; Blastomyces silverae; Blumeria graminis; Blumeriella jaapii; Botryosphaeria obtusa; Botrytis* spp.; *Botrytis allii; Botrytis cinerea; Botrytis elliptica; Botrytis squamosa; Branchiomyces demigrans; Branchiomyces sanguinis; Bremia lactucae; Candida africana; Candida albicans; Candida auris; Candida bracarensis; Candida dubliniensis; Candida duobushaemulonii; Candida famata; Candida glabrata* (formerly classified as *Torulopsis glabrata*); *Candida guilliermondii; Candida haemulonii* var. *vulnera; Candida inconspicua; Candida krusei; Candida lusitaniae; Candida metapsilosis; Candida metapsilosis; Candida nivariensis; Candida orthopsilosis; Candida orthopsilosis; Candida pseudotropicalis; Candida rugosa; Candida tropicalis; Cercospora* spp.; *Cercospora beticola; Cercospora kikuchii; Cercospora sojina; Chrysosporium* spp.; *Cladophialophora* spp.; *Cladophialophora bantiana; Cladophialophora carrionii; Coccidioides immitis; Coccidioides posadasii; Cochliobolus carbonum; Cochliobolus miyabeanus; Colletotrichum* spp. (sexual stage: *Glomerella*); *Colletotrichum acutatum; Colletotrichum gloeosporoides; Conidiobolus* spp.; *Conidiobolus coronatus; Conidiobolus incongruous; Corynespora cassiicola; Cronartium ribicola; Cryptococcus bacillisporus; Cryptococcus decagattii; Cryptococcus deuterogattii; Cryptococcus gattii; Cryptococcus neoformans; Cryptococcus neoformans* var. *grubii* (serotype A); *Cryptococcus neoformans* var. *neoformans; Cryptococcus tetragattii; Cunninghamella bertholletiae; Curvularia* spp.; *Diaporthe helianthi; Diaporthe phaseolorum; Diplocarpon mespili; Drepanopeziza ribis; Dydimella bryoniae; Elsinoe* spp.; *Emergomyces africanus; Emmonsia* spp.; *Emmonsia parva; Epidermophyton* spp.; *Erysiphe cruciferarum; Erysiphe graminis* (*Blumeria graminis*); *Erysiphe heraclei; Erysiphe necator**; Eutypa lata; Exophiala* spp.; *Exserohilum* spp.; *Falciformispora* spp.; *Fonsecaea* spp.; *Fonsecaea monophora; Fonsecaea nubica, Fonsecaea pedrosoi; Fusarium* spp.; *Fusarium fujikuroi; Fusarium graminearum; Fusarium oxysporum; Fusarium oxysporum; Fusarium solani; Gaeumannomyces graminis; Geomyces* spp.; *Geosmithia* spp.; *Geotrichum* spp.; *Gibberella fujikuori; Gloeodes pomigena; Glomerella cingulata* (anamorph: *Gloeosporium fructigenum*); *Gnomonia erythrostoma; Gnomonia leptostyla; Guignardia bidwellii; Gymnosporangium sabinae; Helminthosporium* spp.; *Helminthosporium solani; Hemileia vastatrix; Histoplasma capsulatum; Hypomyces rosellus* (*Dactylium dendroides*); *Icthyophonus hoferi; Kabatiella zeae; Lacazia loboi; Lagenidium* spp.; *Leptosphaeria biglobosa; Leptosphaeria maculans; Leptothyrium pomi; Leveillula taurica; Lichtheimia* (*Absidia*) *corymbifera; Lomentospora* (formerly *Scedosporium*) *prolificans; Macrophomina* spp.; *Madurella* spp.; *Magnaporthe* spp.; *Magnaporthe oryzae; Magnusiomyces capitatus* (formerly called *Saprochaete capitata* and *Blastoschizomyces capitatus*); *Malassezia* spp. (previously *Pityrosporum* spp.); *Malassezia caprae; Malassezia dermatis; Malassezia equina; Malassezia furfur; Malassezia globosa; Malassezia japonica, Malassezia nana, Malassezia obtusa; Malassezia pachydermatis; Malassezia restricta, Malassezia slooffiae; Malassezia sympodialis; Malassezia yamatoensis; Medicopsis* spp.; *Melampsora* spp.; *Melampsora lini; Metarhizium* spp.; *Microsphaeropsis arundinis; Microsporum* spp.; *Microsporum canis; Microsporum gypseum; Microsporum persicolor; Moniliella* spp.; *Monilinia* spp.; *Monocillium indicum; Monographella nivale; Mucor* spp.; *Mucor circinelloides; Mucor velutinosus; Mycosphaerella* spp.; *Mycosphaerella brassicicola; Mycosphaerella fijiensis; Mycosphaerella graminicola; Mycosphaerella graminicola* (*Zymoseptoria tritici*); *Mycosphaerella musicola; Mycosphaerella nawae; Mycosphaerella pinodes; Mycovellosiella nattrassii; Nannizzia* spp.; *Nectria galligena; Neofabraea malicorticis* (anamorph: *Gloeosporium malicorticis*); *Neofabraea perennans* (anamorph: *Gloeosporium perennans*); *Neofabraea vagabunda* (anamorph: *Gloeosporium* album); *Neotestudina rosatii; Ochroconis* spp.; *Oculimacula* spp.; *Oidium neolycopersici; Paecilomyces* spp. (incl *Paecilomyces farinosis*); *Paracoccidioides americana; Paracoccidioides brasiliensis; Paracoccidioides lutzii; Paracoccidioides restrepiensis; Paracoccidioides venezueliensis; Parastagonospora nodorum* (*Stagonospora*); *Penicillium* spp.; *Penicillium digitatum; Penicillium expansum; Phaeoacremonium* spp.; *Phaeoacremonium aleophilum; Phaeomoniella chlamydospora; Phakopsora* spp.; *Phakopsora pachyrhizi; Phialemonium* spp.; *Phialophora* spp.; *Phialophora verrucose; Phoma* spp.; *Phoma macdonaldii; Phomopsis viticola; Phytophthora cactorum; Phytophthora fragariae; Phytophthora infestans; Phytophthora rubi; Pichia anomala; Plasmopara viticola; Pleurostomophora ochracea; Pneumocystis carinii; Pneumocystis jirovecii; Pneumocystis murina; Podosphaera leucotricha; Podosphaera xanthii; Prototheca wickerhamii; Prototheca zopfii; Pseudallescheria* spp.; *Pseudocercospora* (*Mycosphaerella*) *fijiensis; Pseudocercosporella herpotrichoides; Pseudochaetosphaeroma* spp.; *Pseudogymnoascus destructans* (formerly known as *Geomyces destructans; Pseudomicrodochium* spp.; *Pseudoperonospora cubensis; Pseudopezicula tracheiphila* (*Pseudopeziza*); *Puccinia* spp.; *Puccinia sorghi; Pyrenophora teres; Pyricularia oryzae; Pythium* spp.; *Pythium insidiosum; Ramularia collocygni; Rhinocladiella aquaspersa; Rhinosporidium seeberi; Rhizoctonia* spp.; *Rhizoctonia solani; Rhizomucor* spp.; *Rhizomucor pusillus; Rhizopus* spp.; *Rhizopus arrhizus* (*Rhizopus oryzae*); *Rhizopus microsporus; Rhizopus rhizopodoformis; Rhizopus stolonifer; Rhodotorula* spp.; *Rhynchosporium commune* (*secalis*); *Rhynchosporium secalis; Rhytidhysteron* spp.; *Roussoella* spp.; *Saccharomyces cerevisiae; Saksenaea vasiformis, Saprolegnia* spp.; *Scedosporium apiospermum; Scedosporium aurantiacum; Scedosporium boydii* (formerly *Pseudallescheria boydii*); *Schizophyllum commune; Sclerotinia* spp.; *Sclerotinia sclerotiorum; Sclerotium* spp.; *Scolecobasidium* spp.; *Septoria* spp.; *Septoria nodorum; Septoria piricola; Septoria tritici; Sphaerotheca fuliginea; Sphaerulina oryzina; Sporothrix brasiliensis; Sporothrix globose; Sporothrix luriei; Sporothrix mexicana; Sporothrix pallida; Sporothrix schenckii; Staphylotrichum coccosporum; Stemphyllium* spp.; *Syncephalastrum racemosum; Talaromyces* (*Penicillium*) *marneffei; Taphrina deformans; Thielaviopsis* spp.; *Tilletia* spp.; *Tranzschelia* spp.; *Trematosphaeria* spp.; *Trichophyton* spp.; *Trichophyton erinacei; Trichosporon* spp.; *Trichosporon asahii; Trichosporon asahii; Trichosporon cutaneum; Trichosporon domesticum; Trichosporon loubieri; Trichosporon pullulans; Ulocladium* spp.; *Uncinula necator; Uromyces* spp.; *Ustilago* spp.; *Ustilago maydis; Venturia inaequalis; Verticillium* spp.; or *Wangiella* spp.

4. The method according to claim 1, wherein the subject is a human, canine, feline, bovine, ovine, caprine, porcine, equine, chiropteran, avian, piscine, amphibian, or insect species.

5. The method according to claim 1, wherein the compound is administered utilizing a route that is an oral route, injection route, subcutaneous route, intramuscular route, intravenous route, intraperitoneal route, intraosseous route, intrathecal route, intraventricular route, sublingual route, buccal routes, rectal route, vaginal route, ocular route, otic route, nasal route, inhalation route, nebulization route, cutaneous route, or transdermal route.

6. The method according to claim 1, wherein the compound is administered to the subject by enteral or parenteral routes at a dose range selected from that is 0.1 mg/kg to 250 mg/kg subject weight or 5 mg/kg to 50 mg/kg subject weight.

7. The method according to claim 1, wherein the subject is a botanical subject.

8. The method of claim 7, wherein the botanical subject is a tree, timber, herb, vegetable, fruit, berry, bush, grass, seed, seedling, potted plant, or vine.

9. The method according to claim 1, wherein the compound is administered to the subject utilizing a dosing regimen at a frequency to alleviate the signs or symptoms of the infection, twice hourly, once every six hours, once every 12 hours, once daily, twice weekly, once weekly, once every two weeks, once a month, every two months, once every six months, or once yearly.

10. The method according to claim 1, wherein the compound is administered to the subject together with a further antifungal agent or fungicide, an insecticide, or an antibacterial agent.

11. The method according to claim 1, wherein the compound is NCL812 (robenidine) or a therapeutically effective salt thereof and the compound is administered to the subject together with EDTA or a therapeutically effective salt thereof.

12. The method according to claim 11, wherein the compound is administered to the subject together with a combination of EDTA or a therapeutically effective salt thereof and tetracaine or a therapeutically effective salt thereof.

13. A method of treating a fungal colonization or infection caused by a fungal plant in a subject, the method comprising the step of: administering to a subject in need thereof a therapeutically effective amount of a compound, or a stereoisomer, tautomer, pharmaceutically acceptable salt, or prodrug thereof, wherein the compound is selected from: NCL021; NCL062; NCL097; NCL123; NCL134; NCL282; and NCL812.

14. A method of reducing the risk of a fungal colonisation or infection caused by a fungal agent in a subject, the method comprising the step of: administering to a subject in need thereof a therapeutically effective amount of a compound of Formula VIII, a stereoisomer, tautomer, pharmaceutically acceptable salt, or prodrug thereof:

Formula VIII

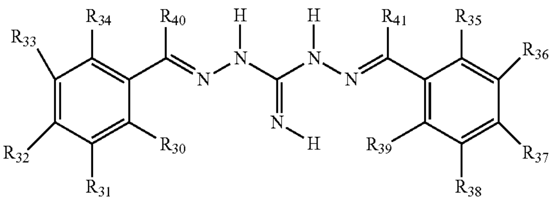

wherein $R_{30}$, $R_{34}$, $R_{35}$, and $R_{39}$ are H;

wherein $R_{31}$ and $R_{38}$ are H or OH;

wherein $R_{32}$ is OH, Cl, Br, F, or $R_{32}$ and $R_{33}$ are bonded together to form a quinoline-6;

wherein $R_{37}$ is OH, Cl, Br, F, or $R_{37}$ and $R_{36}$ are bonded together to form a quinoline-6;

wherein $R_{33}$ and $R_{36}$ are H, OH, or F; and wherein $R_{40}$ and $R_{41}$ are H or methyl.

15. The method according to claim 14, wherein the compound is selected from: NCL021; NCL062; NCL097; NCL123; NCL134; NCL282; NCL812.

16. The method according to claim 14, wherein the fungal agent is *Absidia* spp.; *Acremonium* spp.; *Actinomucor* spp.; *Albugo candida*; *Alternaria alternata; Alternaria brassicae; Alternaria brassicicola; Alternaria helianthi; Alternaria solani; Alternaria* spp.; *Apophysomyces elegans; Armillaria* spp.; *Ascochyta pisi; Ascosphaera apis; Aspergillus* spp.; *Aspergillus alabamensis; Aspergillus algerae; Aspergillus alliaceus* (teleomorph *Petromyces alliaceus*); *Aspergillus avenaceus; Aspergillus caesiellus; Aspergillus calidoustus; Aspergillus candidus; Aspergillus carneus; Aspergillus clavatus; Aspergillus connori; Aspergillus flavipes; Aspergillus flavus; Aspergillus fumigatus; Aspergillus glaucus; Aspergillus granulosus; Aspergillus insuetus; Aspergillus keveii, Aspergillus lentulus; Aspergillus nidulans* (*Emericella nidulans*); *Aspergillus niger, Aspergillus novofumigatus; Aspergillus ochraceus; Aspergillus pseudodeflectus; Aspergillus puniceus; Aspergillus quadrilineatus; Aspergillus restrictus; Aspergillus sydowii; Aspergillus tamarii; Aspergillus tanneri; Aspergillus terreus; Aspergillus thermomutatus* (teleomorph *Neosartorya pseudofischeri*); *Aspergillus tubingensis; Aspergillus udagawae* (*Neosartorya udagawae*); *Aspergillus versicolor; Aspergillus vesicularum; Aspergillus viridinutans; Aspergillus vitus* (teleomorph *Eurotium amstelodami*); *Aspergillus wentii; Austropuccinia psidii* (formerly *Puccinia psidii*, initially identified as *Uredo rangelii*); *Basidiobolus* spp.; *Batrachochytrium dendrobatidis; Batrachochytrium salamandrivorans; Biatriospora* spp.; *Bipolaris* spp.; *Bipolaris maydis; Bipolaris zeicola; Blastomyces dermatitidis; Blastomyces gilchristii; Blastomyces helicus; Blastomyces parvus; Blastomyces percursus; Blastomyces silverae; Blumeria graminis; Blumeriella jaapii; Botryosphaeria obtusa; Botrytis* spp.; *Botrytis allii; Botrytis cinerea; Botrytis elliptica; Botrytis squamosa; Branchiomyces demigrans; Branchiomyces sanguinis; Bremia lactucae; Candida africana, Candida albicans; Candida auris; Candida bracarensis; Candida dubliniensis; Candida duobushaemulonii; Candida famata; Candida glabrata* (formerly classified as *Torulopsis glabrata*); *Candida guilliermondii; Candida haemulonii* var. *vulnera, Candida inconspicua; Candida krusei; Candida lusitaniae; Candida metapsilosis; Candida metapsilosis; Candida nivariensis; Candida orthopsilosis; Candida orthopsilosis; Candida pseudotropicalis; Candida rugosa; Candida tropicalis; Cercospora* spp.; *Cercospora beticola; Cercospora kikuchii; Cercospora sojina; Chrysosporium* spp.; *Cladophialophora* spp.; *Cladophialophora bantiana; Cladophialophora carrionii; Coccidioides immitis; Coccidioides posadasii; Cochliobolus carbonum; Cochliobolus miyabeanus; Colletotrichum* spp. (sexual stage: *Glomerella*); *Colletotrichum acutatum; Colletotrichum gloeosporoides; Conidiobolus* spp.; *Conidiobolus coronatus; Conidiobolus incongruous; Corynespora cassiicola; Cronartium ribicola; Cryptococcus bacillisporus; Cryptococcus decagattii; Cryptococcus deuterogattii; Cryptococcus gattii; Cryptococcus neoformans; Cryptococcus neoformans* var. *grubii* (serotype A); *Cryptococcus neoformans* var. *neoformans; Cryptococcus tetragattii; Cunninghamella bertholletiae; Curvularia* spp.; *Diaporthe helianthi; Diaporthe phaseolorum; Diplocarpon mespili; Drepanopeziza ribis; Dydimella bryoniae; Elsinoe* spp.; *Emergomyces africanus; Emmonsia* spp.; *Emmonsia parva; Epidermophyton* spp.; *Erysiphe cruciferarum; Erysiphe graminis* (*Blumeria graminis*); *Erysiphe heraclei; Erysiphe necator* *; *Eutypa lata; Exophiala* spp.; *Exserohilum* spp.; *Falciformispora* spp.; *Fonsecaea* spp.; *Fonsecaea monophora; Fonsecaea nubica; Fonsecaea pedrosoi, Fusarium* spp.; *Fusarium fujikuroi; Fusarium graminearum; Fusarium oxysporum; Fusarium oxysporum; Fusarium solani; Gaeumannomyces graminis; Geomyces* spp.; *Geosmithia* spp.; *Geotrichum* spp.; *Gibberella fujikuori; Gloeodes pomigena; Glomerella cingulata* (anamorph: *Gloeosporium fructigenum*); *Gnomonia erythrostoma; Gnomonia leptostyla; Guignardia bidwellii; Gymnosporangium sabinae; Helminthosporium* spp.; *Helminthosporium solani; Hemileia vastatrix; Histoplasma capsulatum; Hypomyces rosellus* (*Dactylium dendroides*); *Icthyophonus hoferi; Kabatiella zeae; Lacazia loboi; Lagenidium* spp.; *Leptosphaeria biglobosa; Leptosphaeria maculans; Leptothyrium pomi; Leveillula taurica; Lichtheimia* (Absidia) *corymbifera; Lomentospora* (formerly *Scedosporium*) *prolificans; Macrophomina* spp.; *Madurella* spp.; *Magnaporthe* spp.; *Magnaporthe oryzae; Magnusiomyces capitatus* (formerly called *Saprochaete capitata* and *Blastoschizomyces capitatus*); *Malassezia* spp. (previously *Pityrosporum* spp.); *Malassezia caprae; Malassezia dermatis; Malassezia equina; Malassezia furfur; Malassezia globosa; Malassezia japonica, Malassezia nana, Malassezia obtusa; Malassezia pachydermatis; Malassezia restricta, Malassezia slooffiae; Malassezia sympodialis; Malassezia yamatoensis; Medicopsis* spp.; *Melampsora* spp.; *Melampsora lini; Metarhizium* spp.; *Microsphaeropsis arundinis; Microsporum* spp.; *Microsporum canis; Microsporum gypseum; Microsporum persicolor; Moniliella* spp.; *Monilinia* spp.; *Monocillium indicum; Monographella nivale; Mucor* spp.; *Mucor circinelloides; Mucor velutinosus; Mycosphaerella* spp.; *Mycosphaerella brassicicola; Mycosphaerella fijiensis; Mycosphaerella graminicola; Mycosphaerella graminicola* (*Zymoseptoria tritici*); *Mycosphaerella musicola; Mycosphaerella nawae; Mycosphaerella pinodes; Mycovellosiella nattrassii; Nannizzia* spp.; *Nectria galligena; Neofabraea malicorticis* (anamorph: *Gloeosporium malicorticis*); *Neofabraea perennans* (anamorph: *Gloeospo-*

*rium perennans*); *Neofabraea vagabunda* (anamorph: *Gloeosporium album*); *Neotestudina rosatii; Ochroconis* spp.; *Oculimacula* spp.; *Oidium neolycopersici; Paecilomyces* spp. (incl *Paecilomyces farinosis*); *Paracoccidioides americana; Paracoccidioides brasiliensis; Paracoccidioides lutzii; Paracoccidioides restrepiensis; Paracoccidioides venezueliensis; Parastagonospora nodorum* (*Stagonospora*); *Penicillium* spp.; *Penicillium digitatum; Penicillium expansum; Phaeoacremonium* spp.; *Phaeoacremonium aleophilum; Phaeomoniella chlamydospora; Phakopsora* spp.; *Phakopsora pachyrhizi; Phialemonium* spp.; *Phialophora* spp.; *Phialophora verrucose; Phoma* spp.; *Phoma macdonaldii; Phomopsis viticola; Phytophthora cactorum; Phytophthora fragariae; Phytophthora infestans; Phytophthora rubi; Pichia anomala; Plasmopara viticola; Pleurostomophora ochracea; Pneumocystis carinii; Pneumocystis jirovecii, Pneumocystis murina; Podosphaera leucotricha; Podosphaera xanthii; Prototheca wickerhamii; Prototheca zopfii; Pseudallescheria* spp.; *Pseudocercospora* (*Mycosphaerella*) *fijiensis; Pseudocercosporella herpotrichoides; Pseudochaetosphaeroma* spp.; *Pseudogymnoascus destructans* (formerly known as *Geomyces destructans; Pseudomicrodochium* spp.; *Pseudoperonospora cubensis; Pseudopezicula tracheiphila* (*Pseudopeziza*); *Puccinia* spp.; *Puccinia sorghi; Pyrenophora teres; Pyricularia oryzae; Pythium* spp.; *Pythium insidiosum; Ramularia collocygni; Rhinocladiella aquaspersa; Rhinosporidium seeberi; Rhizoctonia* spp.; *Rhizoctonia solani; Rhizomucor* spp.; *Rhizomucor pusillus; Rhizopus* spp.; *Rhizopus arrhizus* (*Rhizopus oryzae*); *Rhizopus microsporus; Rhizopus rhizopodoformis; Rhizopus stolonifer, Rhodotorula* spp.; *Rhynchosporium commune* (*secalis*); *Rhynchosporium secalis; Rhytidhysteron* spp.; *Roussoella* spp.; *Saccharomyces cerevisiae; Saksenaea vasiformis; Saprolegnia* spp.; *Scedosporium apiospermum; Scedosporium aurantiacum; Scedosporium boydii* (formerly *Pseudallescheria boydii*); *Schizophyllum commune; Sclerotinia* spp.; *Sclerotinia sclerotiorum; Sclerotium* spp.; *Scolecobasidium* spp.; *Septoria* spp.; *Septoria nodorum; Septoria piricola; Septoria tritici; Sphaerotheca fuliginea; Sphaerulina oryzina; Sporothrix brasiliensis; Sporothrix globose; Sporothrix luriei; Sporothrix mexicana; Sporothrix pallida; Sporothrix schenckii; Staphylotrichum coccosporum; Stemphyllium* spp.; *Syncephalastrum racemosum; Talaromyces* (*Penicillium*) *marneffei; Taphrina deformans; Thielaviopsis* spp.; *Tilletia* spp.; *Tranzschelia* spp.; *Trematosphaeria* spp.; *Trichophyton* spp.; *Trichophyton erinacei; Trichosporon* spp.; *Trichosporon asahii; Trichosporon asahii; Trichosporon cutaneum; Trichosporon domesticum; Trichosporon loubieri; Trichosporon pullulans; Ulocladium* spp.; *Uncinula necator; Uromyces* spp.; *Ustilago* spp.; *Ustilago maydis; Venturia inaequalis; Verticillium* spp.; or *Wangiella* spp.

17. The method according to claim 14, wherein the subject is a human, canine, feline, bovine, ovine, caprine, porcine, equine, chiropteran, avian, piscine, amphibian, or insect species.

18. The method according to claim 14, wherein the compound is administered utilizing a route that is an oral route, injection route, subcutaneous route, intramuscular route, intravenous route, intraperitoneal route, intraosseous route, intrathecal route, intraventricular route, sublingual route, buccal routes, rectal route, vaginal route, ocular route, otic route, nasal route, inhalation route, nebulization route, cutaneous route, or transdermal route.

19. The method according to claim 14, wherein the compound is administered to the subject by enteral or parenteral routes at a dose range that is 0.1 mg/kg to 250 mg/kg subject weight or 5 mg/kg to 50 mg/kg subject weight.

20. The method according to claim 14, wherein the subject is a botanical subject.

21. The method of claim 20, wherein the botanical subject is a tree, timber, herb, vegetable, fruit, berry, bush, grass, seed, seedling, potted plant, or vine.

22. The method according to claim 14, wherein the compound is administered to the subject utilizing a dosing regimen at a frequency to alleviate the signs or symptoms of the infection, twice hourly, once every six hours, once every 12 hours, once daily, twice weekly, once weekly, once every two weeks, once a month, every two months, once every six months, or once yearly.

23. The method according to claim 14, wherein the compound is administered to the subject together with a further antifungal agent or fungicide, an insecticide, or an antibacterial agent.

24. The method according to claim 14, wherein the compound is NCL812 (robenidine) or a therapeutically effective salt thereof and the compound is administered to the subject together with EDTA or a therapeutically effective salt thereof.

25. The method according to claim 24, wherein the compound is administered to the subject together with a combination of EDTA or a therapeutically effective salt thereof and tetracaine or a therapeutically effective salt thereof.

26. A method of reducing the risk of a fungal colonization or infection caused by a fungal plant in a subject, the method comprising the step of: administering to a subject in need thereof a therapeutically effective amount of a compound, or a stereoisomer, tautomer, pharmaceutically acceptable salt, or prodrug thereof, wherein the compound is selected from: NCL021; NCL062; NCL097; NCL123; NCL134;

NCL282; and NCL812.

* * * * *